(12) United States Patent
Hochschuler et al.

(10) Patent No.: US 8,308,767 B2
(45) Date of Patent: Nov. 13, 2012

(54) INTERLAMINAR STABILIZATION SYSTEM

(75) Inventors: Stephen Hochschuler, Paradise Valley, AZ (US); Ali Araghi, Scottsdale, AZ (US); Matthew N. Songer, Marquette, MI (US); Thomas S. Kilpela, Marquette, MI (US); Joshua A. Butters, Chandler, AZ (US); Greta Jo Hays, Logan, UT (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 731 days.

(21) Appl. No.: 12/234,557

(22) Filed: Sep. 19, 2008

(65) Prior Publication Data

US 2009/0204150 A1 Aug. 13, 2009

Related U.S. Application Data

(60) Provisional application No. 60/973,659, filed on Sep. 19, 2007.

(51) Int. Cl.
*A61B 17/70* (2006.01)
(52) U.S. Cl. ........ 606/246; 606/248; 606/249; 606/250; 606/278
(58) Field of Classification Search .......... 606/248–253, 606/278
See application file for complete search history.

(56) References Cited

U.S. PATENT DOCUMENTS

| | | | |
|---|---|---|---|
| 3,486,505 A | 12/1969 | Morrison | |
| 4,257,409 A * | 3/1981 | Bacal et al. | 606/252 |
| 4,274,401 A | 6/1981 | Miskew | |
| 4,863,476 A | 9/1989 | Shepperd | |
| 5,000,165 A * | 3/1991 | Watanabe | 606/250 |
| 5,059,193 A | 10/1991 | Kuslich | |
| 5,171,278 A | 12/1992 | Pisharodi | |
| 5,242,445 A * | 9/1993 | Ashman | 606/276 |
| 5,496,318 A | 3/1996 | Howland et al. | |
| 5,620,444 A * | 4/1997 | Assaker | 606/276 |
| 5,667,507 A * | 9/1997 | Corin et al. | 606/250 |
| 5,709,684 A * | 1/1998 | Errico et al. | 606/252 |
| 5,836,948 A | 11/1998 | Zucherman et al. | |
| 5,860,977 A | 1/1999 | Zucherman et al. | |
| 5,876,404 A | 3/1999 | Zucherman et al. | |
| 5,885,284 A * | 3/1999 | Errico et al. | 606/252 |
| 6,039,761 A | 3/2000 | Li et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,077,263 A * | 6/2000 | Ameil et al. | 606/276 |
| 6,090,112 A | 7/2000 | Zucherman et al. | |

(Continued)

FOREIGN PATENT DOCUMENTS

WO WO2005/086776 9/2005
WO WO2006/110578 10/2006

*Primary Examiner* — Alvin Stewart
*Assistant Examiner* — Jerry Cumberledge
(74) *Attorney, Agent, or Firm* — Fitch, Even, Tabin & Flannery, LLP

(57) ABSTRACT

A spinal stabilization system includes vertebral engagement members and an intermediate structure. The vertebral engagement members are configured to be disposed between a first vertebra and a second vertebra. The vertebral engagement members generally include seating surfaces for accommodating at least a portion of a laminar region of adjacent vertebra and are adjustable between an operable and inoperable configuration. The intermediate structure extends between the vertebral engagement members. The structural cooperation of the vertebral engagement members and the intermediate structure is such that the engagement members distract the adjacent vertebrae.

10 Claims, 53 Drawing Sheets

U.S. PATENT DOCUMENTS

| | | | |
|---|---|---|---|
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,193,757 B1 | 2/2001 | Foley et al. | |
| 6,217,578 B1* | 4/2001 | Crozet et al. | 606/252 |
| 6,235,030 B1 | 5/2001 | Zucherman et al. | |
| 6,238,396 B1* | 5/2001 | Lombardo | 606/86 A |
| 6,238,397 B1 | 5/2001 | Zucherman et al. | |
| 6,280,444 B1 | 8/2001 | Zucherman et al. | |
| 6,332,882 B1 | 12/2001 | Zucherman et al. | |
| 6,332,883 B1 | 12/2001 | Zucherman et al. | |
| 6,364,883 B1 | 4/2002 | Santilli | |
| 6,379,355 B1 | 4/2002 | Zucherman et al. | |
| 6,395,031 B1 | 5/2002 | Foley et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,485,491 B1 | 11/2002 | Farris et al. | |
| 6,500,178 B2 | 12/2002 | Zucherman et al. | |
| 6,514,256 B2 | 2/2003 | Zucherman et al. | |
| 6,582,433 B2 | 6/2003 | Yun | |
| 6,592,585 B2* | 7/2003 | Lee et al. | 606/252 |
| 6,626,944 B1 | 9/2003 | Taylor | |
| 6,652,527 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,770,096 B2 | 8/2004 | Bolger et al. | |
| 6,783,546 B2 | 8/2004 | Zucherman et al. | |
| 6,796,983 B1 | 9/2004 | Zucherman et al. | |
| 6,802,845 B2* | 10/2004 | Shirado et al. | 606/324 |
| 6,833,006 B2 | 12/2004 | Foley et al. | |
| 6,902,566 B2 | 6/2005 | Zucherman et al. | |
| 7,029,473 B2 | 4/2006 | Zucherman et al. | |
| 7,048,736 B2 | 5/2006 | Robinson et al. | |
| 7,101,375 B2 | 9/2006 | Zucherman et al. | |
| 7,201,751 B2 | 4/2007 | Zucherman et al. | |
| 2001/0031965 A1 | 10/2001 | Zucherman et al. | |
| 2002/0143331 A1 | 10/2002 | Zucherman et al. | |
| 2003/0065330 A1 | 4/2003 | Zucherman et al. | |
| 2004/0153071 A1 | 8/2004 | Zucherman et al. | |
| 2004/0162617 A1 | 8/2004 | Zucherman et al. | |
| 2004/0167520 A1 | 8/2004 | Zucherman et al. | |
| 2004/0193159 A1 | 9/2004 | Zucherman et al. | |
| 2004/0199255 A1 | 10/2004 | Mathieu et al. | |
| 2004/0220568 A1 | 11/2004 | Zucherman et al. | |
| 2004/0249379 A1 | 12/2004 | Winslow et al. | |
| 2005/0010298 A1 | 1/2005 | Zucherman et al. | |
| 2005/0101955 A1 | 5/2005 | Zucherman et al. | |
| 2005/0143738 A1 | 6/2005 | Zucherman et al. | |
| 2005/0203512 A1 | 9/2005 | Hawkins et al. | |
| 2005/0209603 A1 | 9/2005 | Zucherman et al. | |
| 2005/0228377 A1* | 10/2005 | Chao et al. | 606/61 |
| 2005/0228383 A1 | 10/2005 | Zucherman et al. | |
| 2005/0228384 A1 | 10/2005 | Zucherman et al. | |
| 2005/0240182 A1 | 10/2005 | Zucherman et al. | |
| 2005/0245937 A1 | 11/2005 | Winslow | |
| 2005/0261768 A1 | 11/2005 | Trieu | |
| 2005/0288672 A1 | 12/2005 | Ferree | |
| 2006/0036258 A1 | 2/2006 | Zucherman et al. | |
| 2006/0064165 A1 | 3/2006 | Zucherman et al. | |
| 2006/0064166 A1 | 3/2006 | Zucherman et al. | |
| 2006/0089718 A1 | 4/2006 | Zucherman et al. | |
| 2006/0235521 A1 | 10/2006 | Zucherman et al. | |
| 2006/0241601 A1 | 10/2006 | Trautwein et al. | |
| 2006/0247781 A1 | 11/2006 | Francis | |
| 2006/0259037 A1 | 11/2006 | Hartmann et al. | |
| 2006/0264938 A1 | 11/2006 | Zucherman et al. | |
| 2006/0264939 A1 | 11/2006 | Zucherman et al. | |
| 2006/0265066 A1 | 11/2006 | Zucherman et al. | |
| 2006/0265067 A1 | 11/2006 | Zucherman et al. | |
| 2006/0271049 A1 | 11/2006 | Zucherman et al. | |
| 2006/0271194 A1 | 11/2006 | Zucherman et al. | |
| 2006/0293662 A1 | 12/2006 | Boyer et al. | |
| 2007/0005064 A1 | 1/2007 | Anderson et al. | |
| 2007/0010813 A1 | 1/2007 | Zucherman et al. | |
| 2007/0055246 A1 | 3/2007 | Zucherman et al. | |
| 2007/0073292 A1 | 3/2007 | Kohm et al. | |
| 2007/0073293 A1 | 3/2007 | Martz et al. | |
| 2007/0093823 A1 | 4/2007 | Booth et al. | |
| 2007/0270840 A1* | 11/2007 | Chin et al. | 606/61 |
| 2009/0062918 A1 | 3/2009 | Wang et al. | |

* cited by examiner

INTERLAMINAR STABILIZATION SYSTEM

CROSS-REFERENCE TO RELATED APPLICATIONS

This application claims the benefit of Provisional Application Ser. No. 60/973,659 filed on Sep. 19, 2007, the disclosure of which is hereby incorporated in its entirety by reference.

FIELD OF THE INVENTION

The present invention relates generally to a spinal stabilization system and, more particularly, a spinal stabilization system for distracting and limiting reduction of the intervertebral spacing between adjacent vertebrae.

BACKGROUND OF THE INVENTION

This invention pertains generally to medical implantable devices and particularly to spinal implants. Various devices for internal fixation of bone segments in the human or animal body are known in the art. The most common type of spinal implant system are hook and rod systems and pedicle screw systems which provides a means of gripping a spinal segment. However, both hook and rod and pedicle screw systems have limitations and are not appropriate for all types of spinal disorders.

Conventional hook and rod systems comprise a series of hooks and an elongate rod. Typically, the hooks are positioned against lamina which are not adjacent one another to decompress or compress a section of the spine. Further, the hooks are positioned before being connected to the connecting rod, requiring the surgeon to place each individual hook before attempting to mount the connecting rod onto the hooks.

A conventional pedicle screw system comprises a pedicle screw and a rod receiving device. The pedicle screw includes an externally threaded stem and a head portion. The rod-receiving device couples to the head portion of the pedicle screw and receives a rod (commonly referred to as a distraction rod). Two such systems are inserted into respective vertebrae and adjusted to distract and/or stabilize a spinal column. The pedicle screw does not, by itself, fixate the spinal segment, but instead operates as an anchor point to receive the rod-receiving device, which in turn receives the rod. One goal of such a system is to substantially reduce and/or prevent relative motion between the spinal segments that are being fused.

The implantation of pedicle screw systems are intricate, time consuming, and invasive into the spine of the patient. Typically, a series of pedicle screws must be carefully placed precisely in the narrow pedicle region of the spine. These pedicle screws are then fitted with rod receiving devices which are then in turn fitted with distraction rods. The system of screws and rods creates an intricate system for supporting the spine that takes considerable effort.

The placement of the screws and rods is time consuming because the components must be positioned through trial and error with repeated adjustment of position of the components until final proper positioning of all the components of the entire system is achieved simultaneously. Finally, the implantation of pedicle screw systems is highly invasive because screws must be deeply driven into the pedicle region of the spine within close proximity of the nerves of the spinal cord or spinal nerves branching off of the spinal cord. A more rapid and less invasive implantation system was sought to structurally support the spine especially in spinal stenosis patients where the settling of the spine causes impingement on the nerves yet the intervertebral discs remain largely intact.

SUMMARY OF THE INVENTION

In accordance with one form, a spinal implant assembly for engaging adjacent vertebrae includes a pair of vertebral gripping devices and an elongate guide rod which extends along a rod axis between the vertebral gripping devices. The vertebral gripping devices include a body portion configured to be secured to the guide rod for translation therealong and hooks that are offset from each other relative to the rod axis, with the translatable body portions allowing the offset hooks to be engaged with offset portions of the adjacent vertebrae for distraction thereof.

One advantage of this form is that it allows the spinal implant assembly to have a minimal insertion profile. This is beneficial because the smaller the insertion profile, the less the adjacent vertebrae must be distracted, if at all, for the spinal implant assembly to be inserted therebetween.

According to another form, the offset of the hooks is sized to allow the body portions to be translated toward each other to a compact orientation to minimize space therebetween.

According to another form, the offset hooks extend different distances along the rod axis.

According to another form, the hook portions include a contoured surface configured for engaging a predetermined portion of the vertebrae.

According to another form, the contoured surface includes inner surface portions that are inclined relative to each other.

According to another form, the body portion includes an annular throughbore configured to receive the elongate guide rod.

According to another form, the throughbore is oversized relative to the rod to allow the rod to be shifted laterally within the throughbore.

In accordance with a second form, a spinal implant assembly includes a first body portion, a second body portion, and a rod portion. The first body portion includes a first lateral surfaces, and first front surface and back surfaces extending laterally between the lateral surfaces. The second body portion including second lateral surfaces, and second front and back surfaces extending laterally between the lateral surfaces. The rod portion including a longitudinal rod axis with the bodies configured to be guided for translation along the rod portion from a compact orientation with the back surfaces of the bodies being closely adjacent or engaged with each other and an operable orientation with at least one of the bodies being shifted along the rod away from the other body to be distal therefrom. Further, the first body includes a first seat portion including a recessed groove therein that extends across a portion of one of the first lateral surfaces, the first front surface, and across a portion of the other first lateral surface and configured to extend about an inferior portion of the upper lamina of the adjacent lamina. Additionally, the second body portion includes a second seat portion including a second recessed groove therein that extends across a portion of the rear surface, one of the lateral surfaces, the second front surface, and across a portion of the other lateral surface and configured to extend about a superior portion the upper lamina of the adjacent lamina. The seat portions of the first and second body portions having contoured surface portions that allow the seat portions to self adjust to the contour of the vertebrae when engaged therewith in the operable orientation thereof.

According to another form, the first seat includes surface portions that are inclined relative to the rod axis.

According to another form, the second seat includes surface portions that are inclined relative to the rod axis.

According to another form, the second body portion is translatable along the rod portion.

According to another form, the body portions extend different lengths generally normal to the rod axis.

According to another form, the second seat extends above a lower rod surface of the rod portion.

According to another form, the rod portion is configured to accept a bumper between the first and second body portions.

According to another form, the bumper is resilient.

According to another form, the inoperable orientation is defined by the first rear surface of the first body portion being in contact with the second rear surface of the second body portion.

In accordance with a third form, a spinal implant assembly includes a first hook portion, a second hook portion, and a guide mechanism connecting the first and second hook portions. The guide mechanism includes a one-way locking mechanism to permit shifting of at least one of the first and second hook portions from a compact orientation to an operable orientation and block shifting from the operable orientation to the compact orientation.

According to another form, the one-way locking mechanism is a ratcheting mechanism.

According to another form, the one-way locking mechanism includes cooperating teeth portions each having a camming surface and a stop surface.

According to another form, the guide mechanism is a pivotal guide mechanism.

According to another form, the pivotal guide mechanism includes a pivot pin that pivotably connects the hooks portions together.

According to another form, the guide mechanism is a linear guide mechanism.

In accordance with a fourth form, a spinal implant assembly includes a generally U-shaped body, a pair of vertebral engaging arms and a pivot mechanism. The U-shaped body includes a base portion, side arm portions extending from the base portion, and a stop portion extending between the side arm portions. The pair of vertebral engaging arms are configured to be received between the parallel side arm portions and have inoperable and operable configurations. The a pivot mechanism is configured for pivotably connecting the vertebral engaging arms and the body portion, with the vertebral engaging arms engaged with the stop portion in the operable configuration thereof and pivoted away from the stop portion toward each other in the inoperable configuration.

According to another form, the vertebral engaging arms include engagement ends and intermediate portions, the intermediate portions configured to have a width less than a width of the engagement ends to minimize space between the vertebral engagement arms in the inoperable configuration.

According to another form, one of the vertebral engaging arms includes a narrow proximal end and the other vertebral engaging arm includes a slotted proximal end configured to receive the narrow proximal end therein.

According to another form, the body portion includes a throughbore and locking mechanism for engaging the vertebral engaging arms and blocking movement thereof while in the operable configuration.

According to another form, the throughbore is threaded and the locking mechanism is a threaded set screw.

DETAILED DESCRIPTION OF THE PREFERRED EMBODIMENTS

Figure 1:
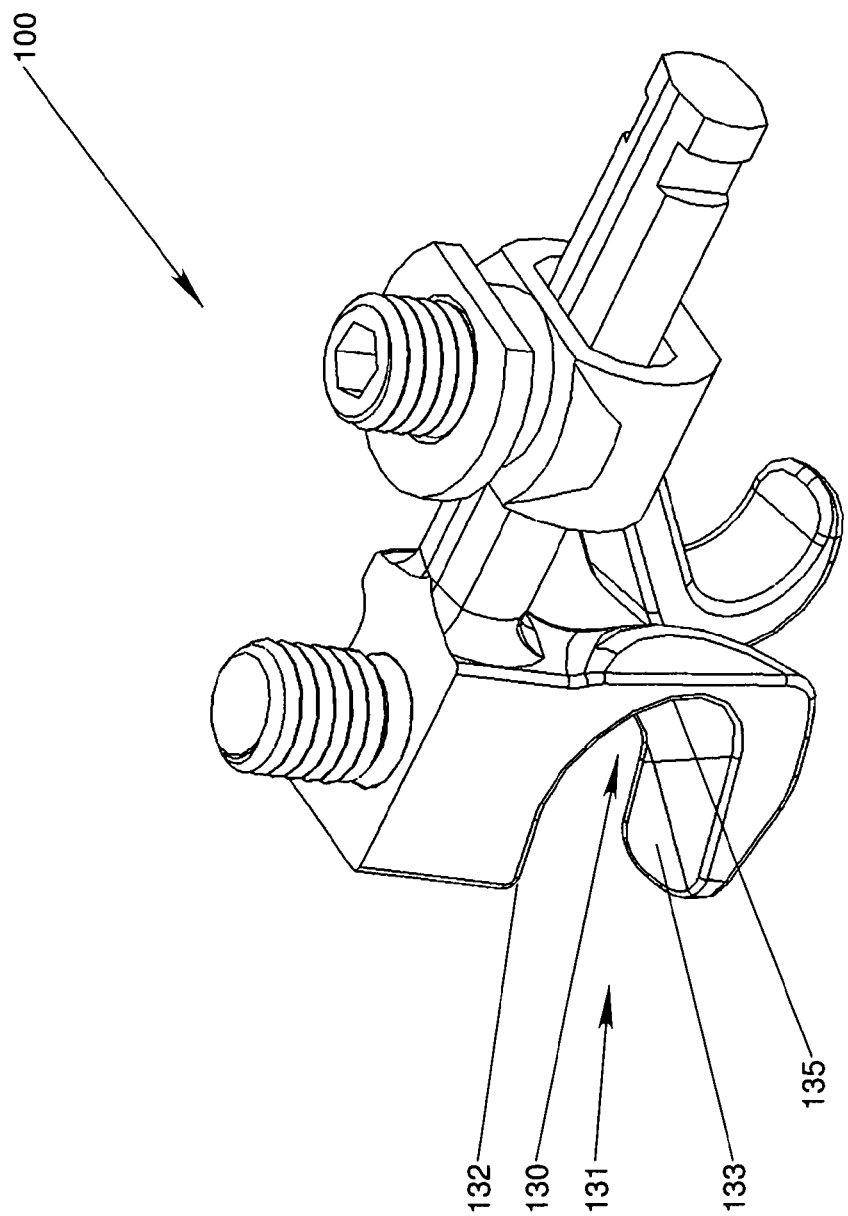
FIG. 1 is a perspective view of a spinal implant assembly according to a first form of the present invention.

Generally, the present invention provides a spinal stabilization system for supporting at least one vertebra of a spine and, more particularly, a laminar region of at least one vertebra. Referring briefly to FIGS. 7A, 7B, 15, 16, a vertebra 1 of a spine generally includes a body 3 and a vertebral arch 5 defining a vertebral foramen 15. The vertebral arch 5 includes a spinous process 7, a pair of transverse processes 9, a laminar region 11, and pedicle regions 13. The spinous process 7 extends generally directly posterior to the body 3 opposite the vertebral foramen 15. The laminar region 11 is disposed directly behind the spinous process 7 and extends between and interconnects the spinous process 7 to the transverse processes 9. The transverse processes 9, therefore, extend generally laterally from the laminar region 11 on each side of the spinous process 7. The pedicle regions 13 are disposed between and interconnect the transverse processes 9 and, therefore, the entire vertebral arch 5 to the body 3. As depicted, the laminar region 11 is a generally arch-shaped wall including a superior edge 11a, an inferior edge 11b, an anterior surface 11c and a posterior surface 11d. A system in accordance with the principles of the present invention provides support on one or both sides of the central longitudinal axis L of the spine by engaging the superior and inferior edges 11a, 11b of the laminar regions 11 of adjacent vertebrae 1, thereby minimizing the possibility of spinal misalignment caused by the system. Multiple variations and examples of the present invention will now be described herein with direct reference to the drawings.

The spinal stabilization device 100, 200, 300, 400, 500 described herein includes a first vertebral gripping portion, a second vertebral gripping portion, and an intermediate portion extending therebetween. The spinal stabilization device 100, 200, 300, 400, 500 is interposed between the laminar regions 11 of adjacent vertebrae 1a, 1b. Specifically, the first vertebral gripping portion engages the inferior edge 11b of the laminar region 11 of the superior vertebra 1a and the second vertebral gripping portion engages a superior edge 11a of a laminar region 11 of the inferior vertebra 1b, while the intermediate portion provides support therebetween. Thus, the spinal stabilization device 100, 200, 300, 400, 500 counteracts any compressive loads applied to the adjacent vertebrae to maintain an appropriate intervertebral spacing therebetween. Specifically, the compressive loads are transferred from one of the superior and inferior vertebra 1a, 1b through the spinal stabilization system 100, 200, 300, 400, 500 to the other of the superior and inferior vertebra 1a, 1b. The semi-rigid construction of the spinal stabilization system 100, 200, 300, 400, 500, which will be described below, therefore acts as a crutch, stilt or resilient spacer between the vertebrae 1a, 1b. Further structural details of the spinal stabilization device 100, 200, 300, 400, 500 will now be described.

FIGS. 1-8 depict a spinal implant 100 according to a first form of the present invention. The spinal implant 100 includes a first vertebral gripping device 110, a second vertebral gripping device 140 and a rod portion 180. The first and second vertebral gripping devices 110, 140 are attached to the rod portion 180, and at least one of the first and second vertebral gripping devices 110, 140 is configured to extend along the longitudinal axis 184 of the rod portion 180.

Figure 2:
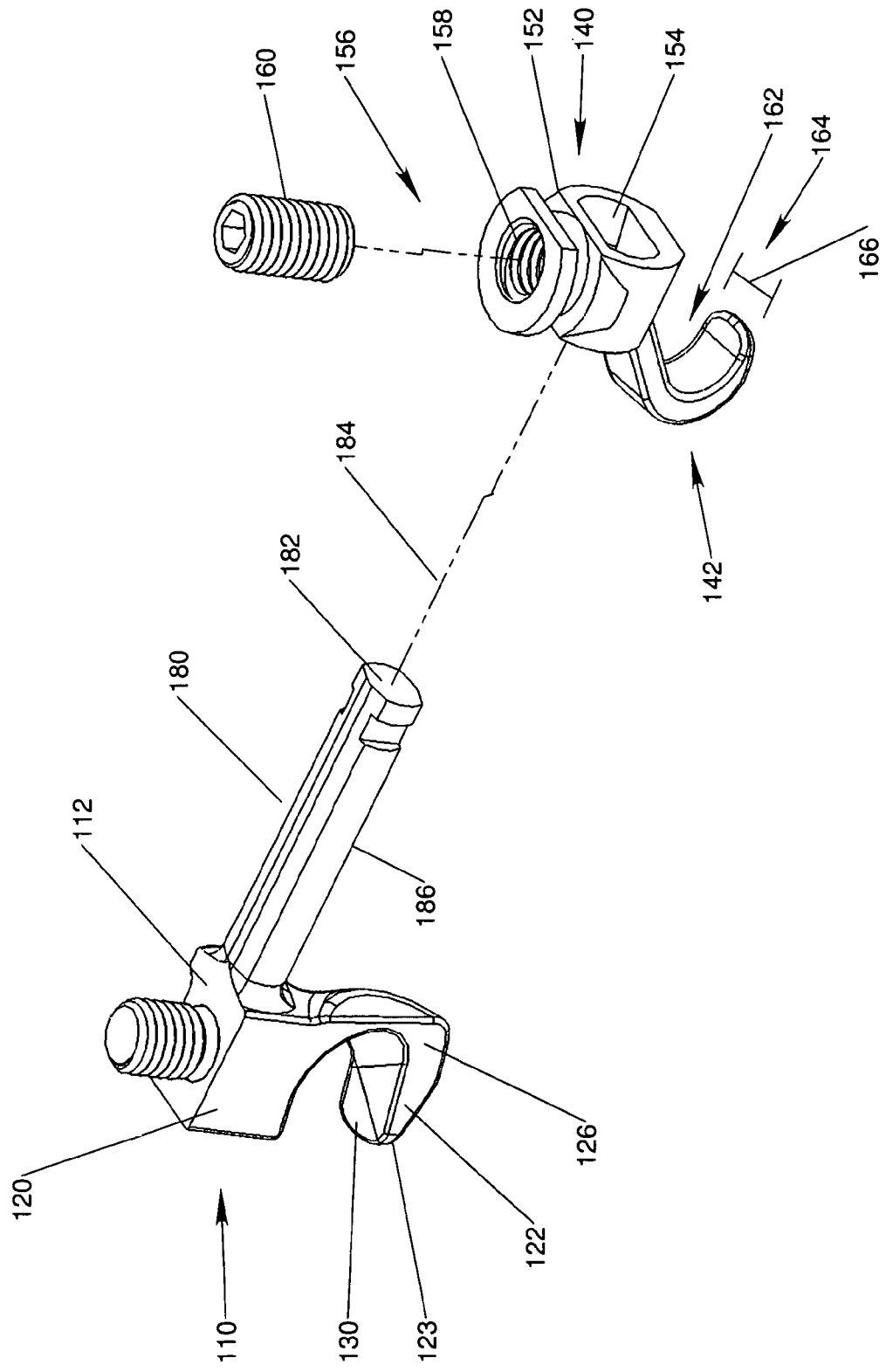
FIG. 2 is an exploded perspective view of the spinal implant assembly of FIG. 1.
Figure 3:
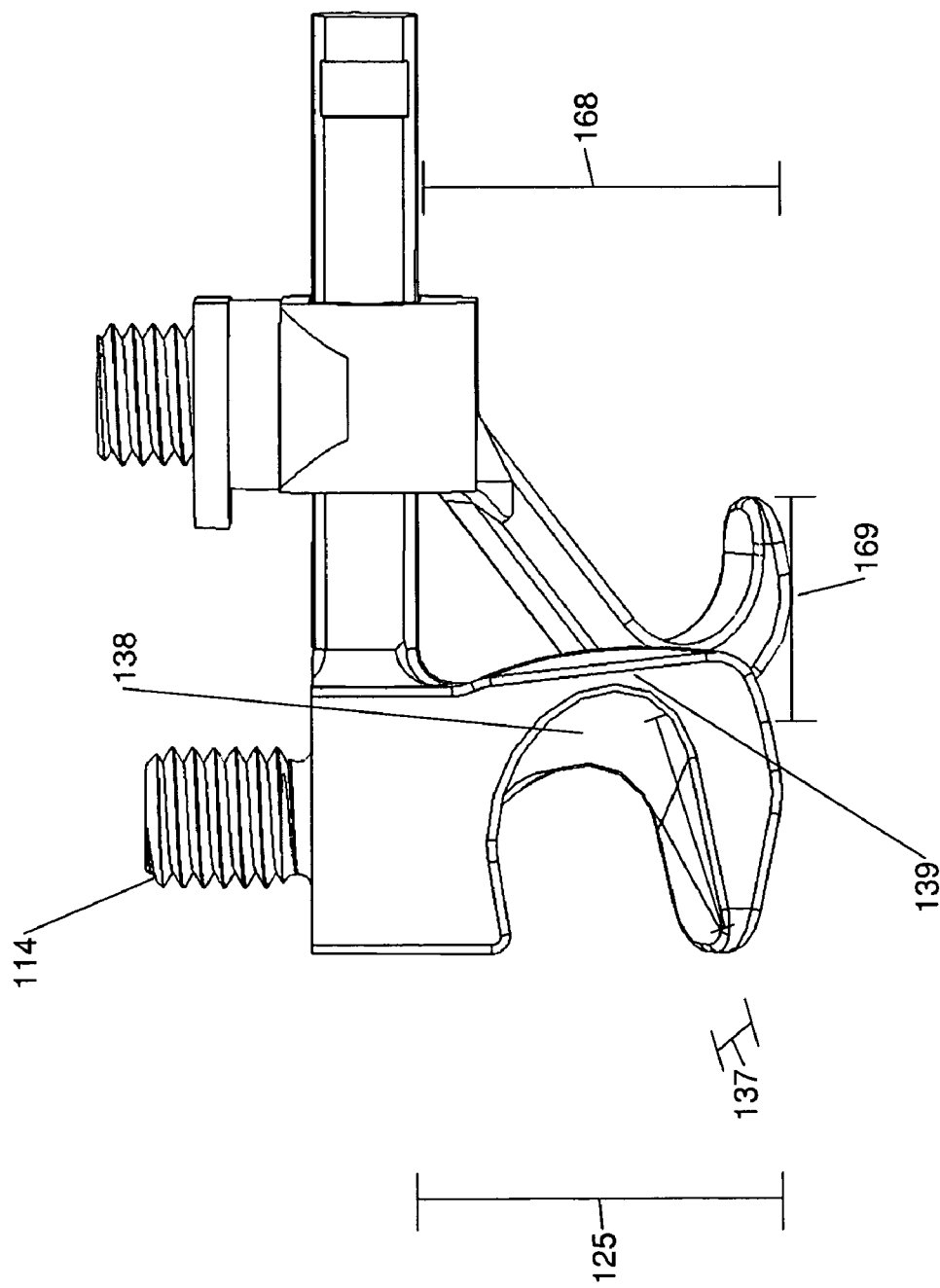
FIG. 3 is a side view of the spinal implant assembly of FIG. 1 showing the vertebral gripping devices along the rod.

As shown in FIGS. 1-3, the first vertebral gripping device 110 includes a first base portion 112 and first hook portion 122 extending from the first base portion 112. In one aspect, the first base portion 112 and first hook portion 122 are integral. In another aspect of the invention, the connection between the first base portion 112 and first hook portion 122 allows for the hook 122 to freely move along one or more axes, such as with a hinge connection, ball and socket, or other similar connection methods (not shown).

The first base portion 112 can optionally include a boss portion 114 extending opposite the first hook portion 122. The boss portion 114 is configured to be engaged by a transverse member 116 which may be used to connect two spinal implants 100, the transverse member 116 extending across the midline of the spine. The transverse member 116 can be linear or curved, and can be configured to extend through the interspinous tissue or outwardly and around the interspinous tissue. Further, in an alternative embodiment, more than one transverse member 116 is used to connect two spinal implants 100. Preferably, the boss 114 is threaded to permit the transverse member 116 to be securely attached to the boss portion 114 by a securing mechanism, such as a nut.

The first rod portion 180 extends laterally from the first vertebral gripping device 110 along a rod axis 184. In one aspect, the first base portion 112 is integral with the rod portion 180. In another aspect, the rod portion 180 is connected to the first base portion 112 by any known method. As an example (not shown), the first base portion 112 includes a throughbore configured to accept the rod portion 180 therein. The rod portion 180 is securable within the throughbore by any known securing mechanism such as a set screw or pin.

In one aspect, the rod portion 180 includes an annular outer edge configured to permit rotation of one or both of the first and second vertebral gripping device 110, 140 therearound. In a preferred embodiment, as shown in FIG. 1, the rod portion 180 has a non-annular surface 186 to restrict rotation around the rod portion 180.

Figure 6:
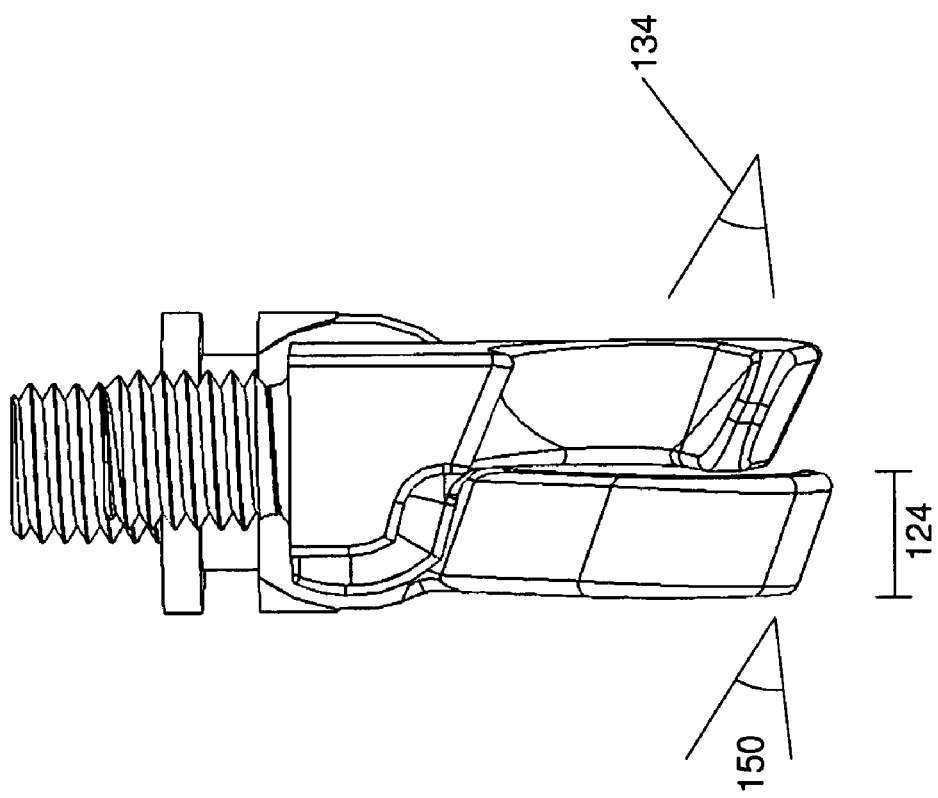
FIG. 6 is an end view of the spinal implant assembly of FIG. 1 showing the offset hooks.

As shown in FIG. 6, the first hook portion 122 has a first width 124 that is less than the width 118 of the first base portion 112. The first hook portion 122 is offset from the first base portion 112 and the rod portion 180. Preferably, the first hook portion 122 is offset so that a first side surface 120 of the first body portion 112 is in line with a first side surface 126 of the first hook portion 122. Preferably, the width 124 of the first hook portion 122 does not extend beyond the center 181 of the longitudinal axis 184 of the rod member 180.

The first hook portion 122 further includes a first seat portion 130 and a tapered distal end portion 123. The distal end portion 123 is tapered to ease in insertion and to minimize the amount of material that is introduced behind the lamina while maintaining the overall strength of the first hook portion 122. The first seat portion 112 has a generally C-shape 131. In one embodiment, the seat portion 130 has a contoured surface configured to engage and extend around the lamina. Preferably, the upper and lower walls 132, 133 of the first seat portion 130 extend across the width 137 of the first seat portion 130 at an upward angle 134 relative to the rod axis 184. The angle 134 of incline is predetermined to conform to the geometry of the individual lamina being engaged.

Further, the rear wall 135 of the first seat portion 130 is tapered across the width 137 of the first seat portion 130 such that the rear wall 135 has a first width 138 at one side of the first seat portion 130 and has a second width 139 shorter than the first width 138 on the other side of the first seat portion 130. Preferably, the rear wall portion 130 has the shorter, second width 139 on the same side of the seat portion 130 as the lowermost part of the upper and lower wall portions 137, 133. As with the angle 134 of the taper, the rear wall portion 135 of the first seat portion 130 is configured to conform to the geometries of the individual lamina being addressed.

The second vertebral gripping device 140 includes a second hook portion 142 and a second body portion 152, the second hook portion 142 extending from the second body portion 152. The second body portion 152 is configured to engage the rod portion 180 and permit the second body portion 152 to translate along the rod portion 180. As shown in FIG. 2, in one embodiment a rod accepting throughbore 154 extends through the second body portion 152. In one embodiment, the rod accepting throughbore 154 is configured to snugly engage the rod portion 180. In an alternative embodiment, as shown in FIG. 6, the rod accepting throughbore 154 is configured to permit the rod portion 180 to adjust laterally and vertically a predetermined amount to allow the second hook portion 142 to not interfere with the first hook portion 122' when the spinal implant 100 is positioned in the compact or inoperable orientation, and to aid in insertion and engagement of the spinal implant 100 with the lamina. The second body portion 152 is secured to the rod portion 180 by a securing mechanism 156. As an example, as shown in FIGS. 1 and 2, the body portion 152 includes a threaded throughbore 158 extending through the body portion 152 to the rod accepting throughbore 154. The threaded throughbore 158 is configured to accept a set screw 160 therein, the set screw 160 being operable to engage and urge the rod portion 180 against the rod accepting throughbore 154, thereby restricting the movement of the second hook body portion 142 along the rod portion 180.

The second hook portion 142 is connected to and extends from the second body portion 152. In one aspect, the second hook portion 142 is integral with the second body portion 152 as shown in FIGS. 1-4. In an alternative aspect, the second hook portion 142 is connected to the second body portion 152 so as to allow for the hook 142 to freely move along one or more axes, such as with a hinge connection or ball and socket. By allowing the second hook portion 142 to freely move in relation to the second body portion 152 the spinal implant 100 can be adjusted to fit the lamina upon insertion and engagement.

The second hook portion 142 extends downward and away from the second body portion 152. The second hook portion 142 includes a straight portion 144 and a curved portion 146 having a second distal end 148. The second straight portion 144 extends downwardly and away from the second body portion 152 at a predetermined angle 150 more than 0 degrees and less than 90 degrees, the predetermined angle 150 depending on the size and geometry of the lamina to be engaged. The second curved section 146 extends from the end of the second straight section 144, and is tapered along a portion thereof toward the second distal end 148. The second curved section 146 is tapered to minimize the size of the implant 100 that is positioned around the lamina while maintaining the desired strength and durability of the spinal implant 100.

The second hook portion 142 extends normally from the rod portion 180 a second distance 168 further than the distance 125 the first hook portion 122 extends normally from the rod portion 180. The second distance 168 is predetermined based on the orientation of the lamina to be engaged. Generally, within the spine the superior edge of the lamina is set back further than the inferior edge of the lamina. By extending the second hook portion 142 further than the first hook portion 122 to account for the setback, the spinal implant 100 maintains its orientation extending along the spine and does not interfere with other portions of the spine, such as the lamina, spinous processes, and transverse processes.

The second hook portion 142 further includes a second seat portion 162 for engaging the lamina. As shown in FIG. 2, the second seat portion 162 has a generally C-shape 164. Similar to the first seat portion 130, in one embodiment the second seat portion 162 extends upwardly across the width 166 of the second seat portion 162 at an angle relative to the rod axis 184 to accommodate the geometry of the lamina.

Figure 4:
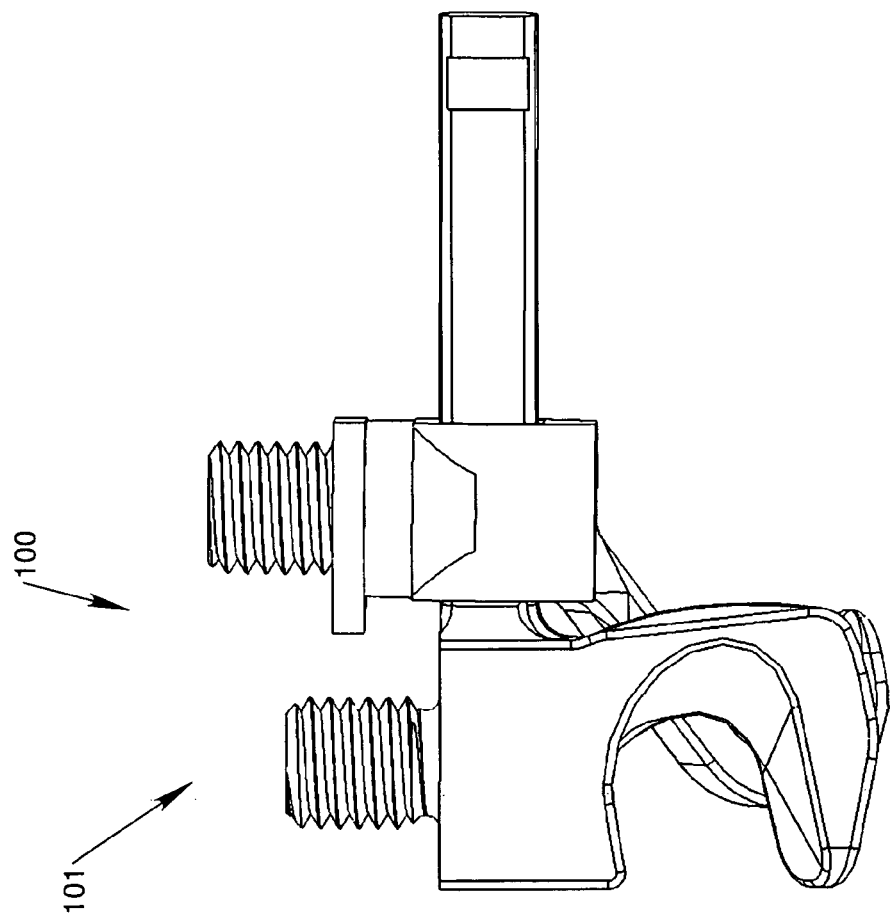
FIG. 4 is a side view of the spinal implant assembly of FIG. 1 in the compact orientation.
Figure 5:
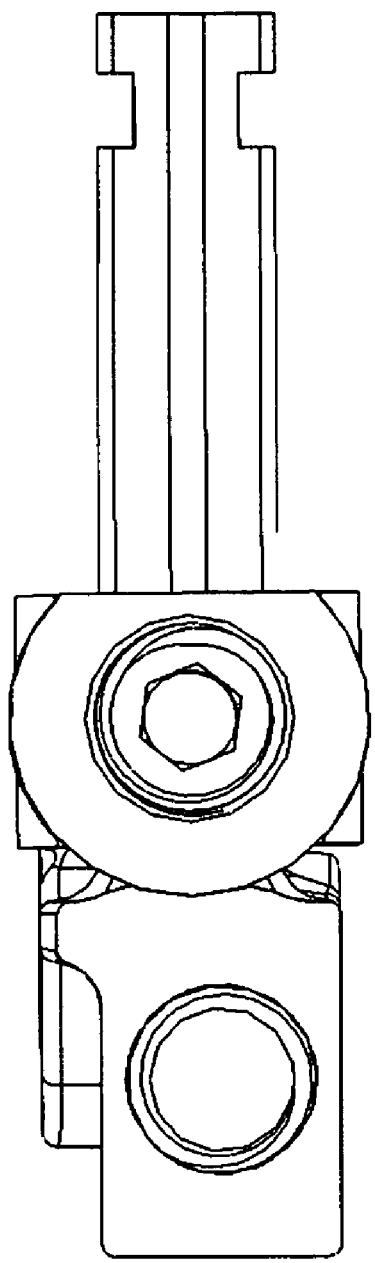
FIG. 5 is a top plan view of the spinal implant assembly of FIG. in the compact orientation.

The second hook portion 142 is preferably offset from the second body portion 152 and the rod portion 180. The offset of the second hook portion 142 is predetermined to minimize interference between the first and second hook portions 122, 142 and permit the hook portions 122, 142 to laterally overlap when the spinal implant 100 is in the compact orientation 101 as shown in FIG. 4. Further, the distance 169 that the second hook portion 142 extends along the rod axis from the second body portion 152 is predetermined so that when the spinal implant 100 is in the compact orientation 101, the first and second hook portions 122, 142 overlap while the first and second body portions 112, 152 are adjacent or abut along the rod portion 180. Preferably, the first and second hook portions 122, 142 overlap such that the overall profile of the first and second hook portions 122, 142 in the compact orientation 101 is approximately the same as the overall profile of the first hook portion 122, thereby minimizing the distance the lamina would need to be distracted for insertion of the spinal implant 100.

Preferably, the first hook body portion 122 is configured to engage the inferior surface of a first lamina, the second hook body portion 142 configured to engage the superior surface of a second lamina, the first lamina being located directly above the second lamina along the spine.

FIGS. 9-16 depict a spinal implant 200 according to a second form of the present invention. In another aspect of the invention, the spinal implant 200 is configured to self adjust to the contour of the vertebrae within an interlaminar space when translated from the compact orientation 201 to the operable orientation 202. The spinal implant 201 includes a first body portion 210, a second body portion 240 and a rod portion 270 extending tangentially from the second body portion 240. The second body portion 240 is connected to the rod portion 270. In one embodiment, the second body portion 240 is integral with the rod portion 270. In an alternative embodiment, the second body portion 240 is secured to the rod portion 270 by a securing mechanism, such as a set screw (not shown) and may be translatable along the rod portion 270.

Figure 11:
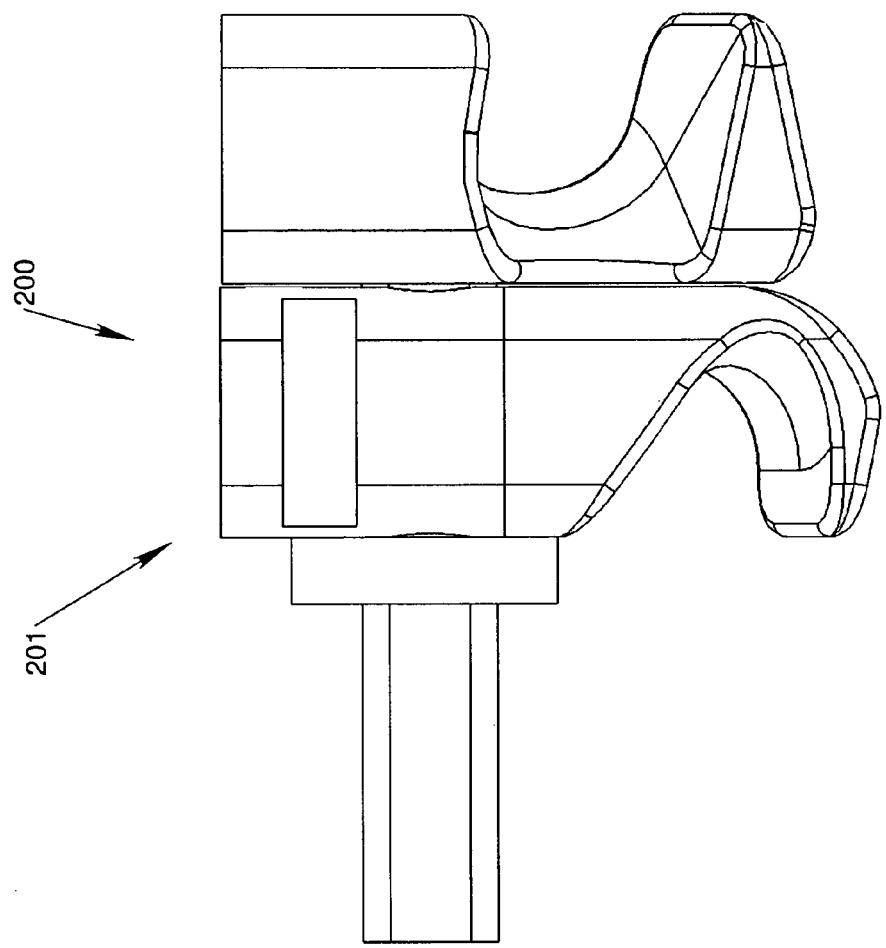
FIG. 11 is a side view of the spinal implant assembly of FIG. 9 showing the assembly in the compact orientation.
Figure 12:
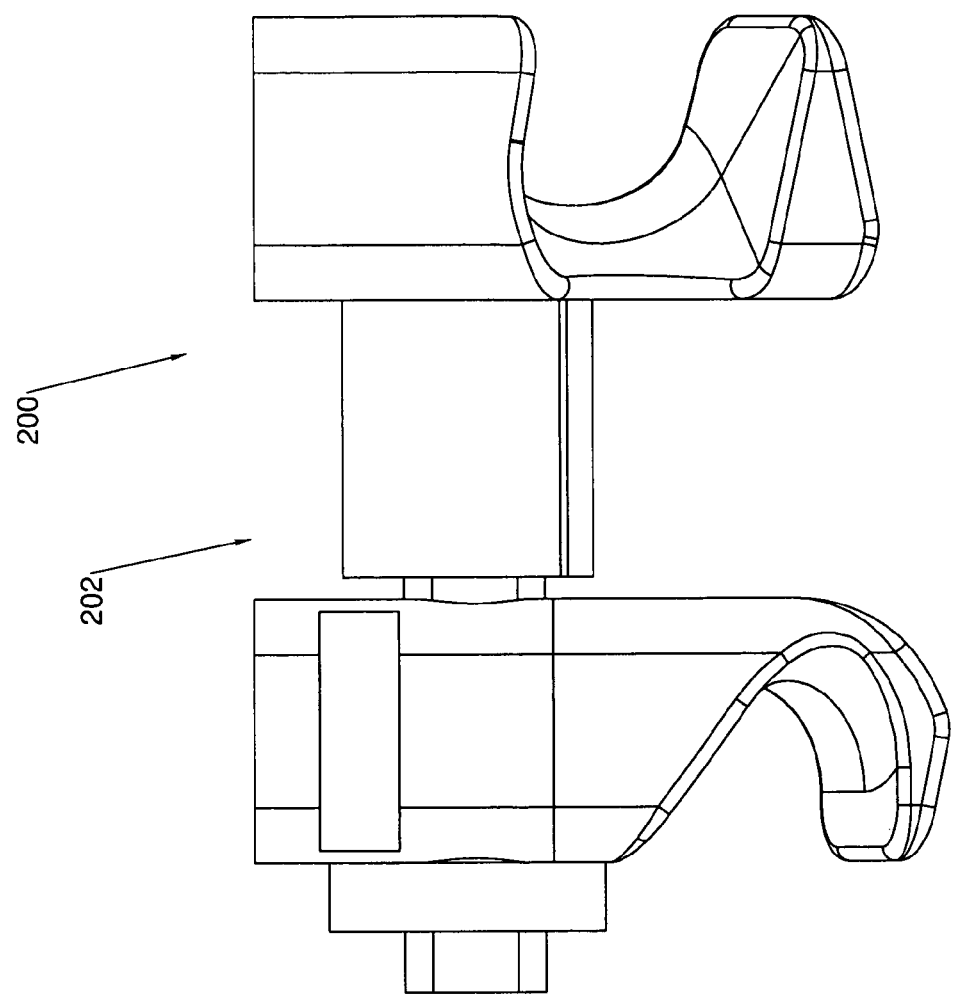
FIG. 12 is a side view of the spinal implant assembly of FIG. 9 showing the assembly in the operable orientation.

The first body portion 210 includes a first hook portion 212 comprising two first lateral surfaces 214, a first rear surface 216, a first forward surface 218 and a first inferior surface 220. The first body portion 210 includes a width 222, a depth 224, and a height 226. The first body portion 210 further includes first seat portion 227 for engaging an inferior portion of a lamina, the first seat portion 227 including a recessed groove that extends across a portion of one of the first lateral surfaces 214, across the first forward surface 218 and across the other first lateral surface 214. The recessed groove further extends from the first forward surface 218 toward the first rear surface 216. The recessed groove 228 extends across the first hook portion 212 at an angle 230 relative to the rod axis 274 between the lateral surfaces 214. The angle 230 is selected to accommodate the shape and configuration of the inferior lamina surface. Further, in alternative embodiments, the recessed groove can includes varying radii of curvature and slopes of curvature. In a further embodiment, the radii of curvature and slope of the curves may vary across between the lateral surfaces 214 of the first body portion 210 and as the recessed groove extends from the forward surface 218 to the rear wall 216. Preferably, as shown in FIGS. 11, 12, the portion of the rear wall 216 defining the seat 227 tapers across the width 222 of the first body portion 210. Additionally, as the seat 227 extends across the width 222 of the first body portion 210 the seat 227 extends upwardly along the height 226 of the first body portion 210.

The first body portion 210 includes a rod accepting portion 242 configured to permit the first body portion 210 to translate along the rod portion 270. In one embodiment the rod portion 270 has an annular surface to permit the first body portion 210 to rotate around the longitudinal axis 274 of the rod portion 270. In a preferred embodiment the rod portion 270 has a non-circular surface 272 to restrict rotation of the first body portion 210 around the rod portion 270.

The second body portion 240 includes a second hook portion 244 comprising two second lateral surfaces 246, a second rear surface 248, a second forward surface 250 and a second inferior surface 252. The second body portion 240 includes a width 254, a depth 256, and a height 258. The second body portion 240 further includes second seat portion 260 for engaging a superior portion of a lamina, the second seat portion 260 being defined by an recessed groove 262 extending across a portion of the rear surface 248, one of the lateral surfaces 246, the forward surface 250 and a portion of the other lateral surface 246. Further, the recessed groove 262 extends from the second forward surface 250 toward the second rear surface 248.

Figure 13:
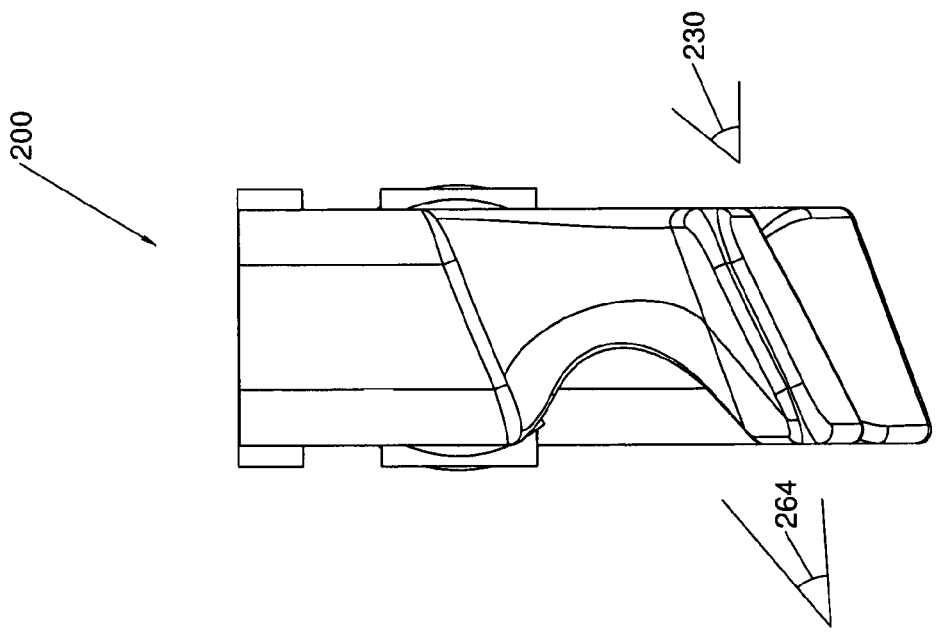
FIG. 13 is an end view of the spinal implant assembly of FIG. 9.

In one embodiment, as shown in FIG. 13, the recessed groove 262 extends across the second hook portion 240 at an angle 264 relative to the rod axis 274 between the second lateral surfaces 246. The angle 264 is selected to accommodate the shape and configuration of the superior lamina surface.

Figure 9:
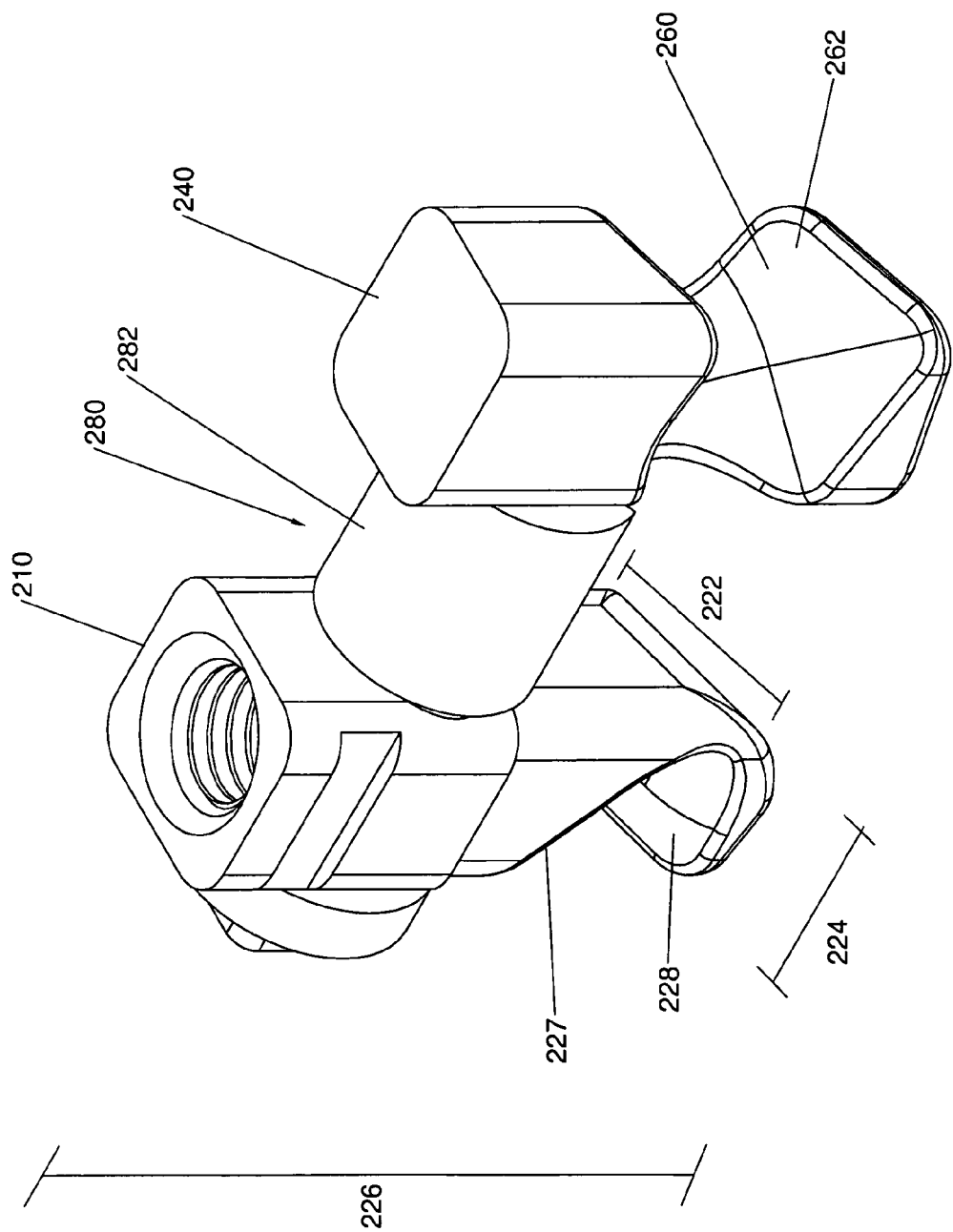
FIG. 9 is a perspective view of a spinal implant assembly according to a second form of the present invention.
Figure 10:
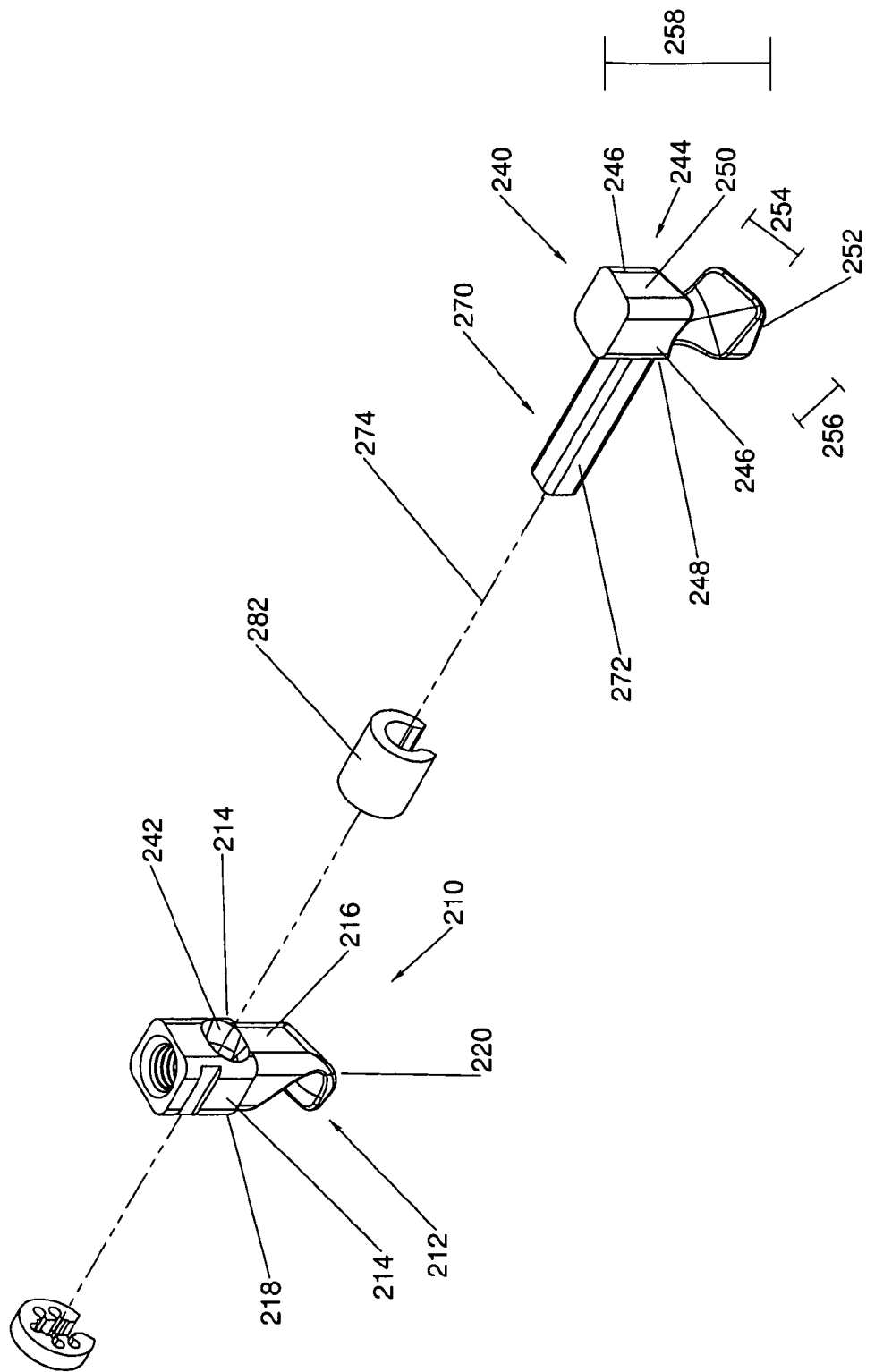
FIG. 10 is an exploded perspective view of the spinal implant assembly of FIG. 9.

Preferably, as shown in FIGS. 9, 11 and 12, the portion of the rear wall 248 defining the seat 260 tapers across a portion of the width 254 of the second body portion 240 such that the rear wall portion 248 does not extend the width 254 of the second body portion 240 along at least a portion of the second seat portion 260. In one embodiment, as shown in FIG. 12, as the seat 260 extends across the width 254 of the second body portion 240 the seat 260 extends upwardly along the height 258 of the second body portion 240.

In one embodiment, the second seat portion 260 includes a contoured configured surface to self adjust to the contour of the superior portion of a lamina when engaged in the operable orientation. In one embodiment, the contoured surface includes varying radii of curvature and slopes extending across the seat portion 260. The radii of curvature and slopes of the contoured surface can vary between the lateral surfaces 246, from the front surface 250 toward the rear surface 248, and along the height of the seat portion 260.

The spinal implant 200 includes a compact or inoperable orientation 201 and an operable orientation 202, each of which is defined by the location of the first body portion 210 and the second body portion 240 on the rod portion 270. The compact orientation 201 is defined by the first body portion 210 being translated toward the second body portion 240 such that the first and second rear surfaces 216, 248 of the first and second body portion 210, 240 are adjacent. The operable orientation 202 is defined by moving at least the first body portion 240 along the rod portion 270 a predetermined distance to engage the lamina. As the first and second body portions 210, 240 engage the lamina, the configuration of the first and second seats 227, 260 urge the implant 200 to the appropriate implantation orientation for ease of insertion.

Figure 14:
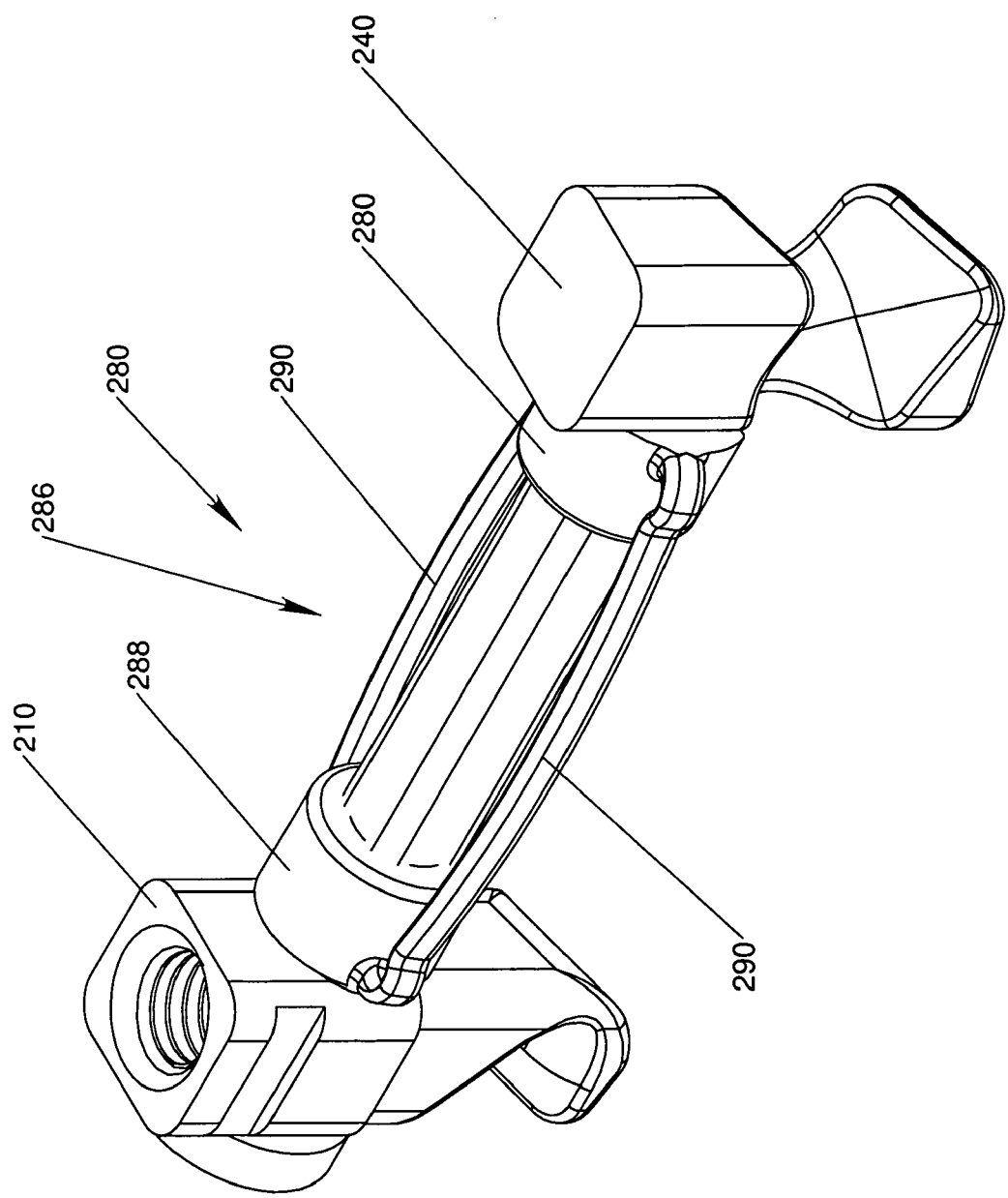
FIG. 14 is a perspective view of the spinal implant assembly of FIG. 9 showing an alternative spacer.
Figure 15:
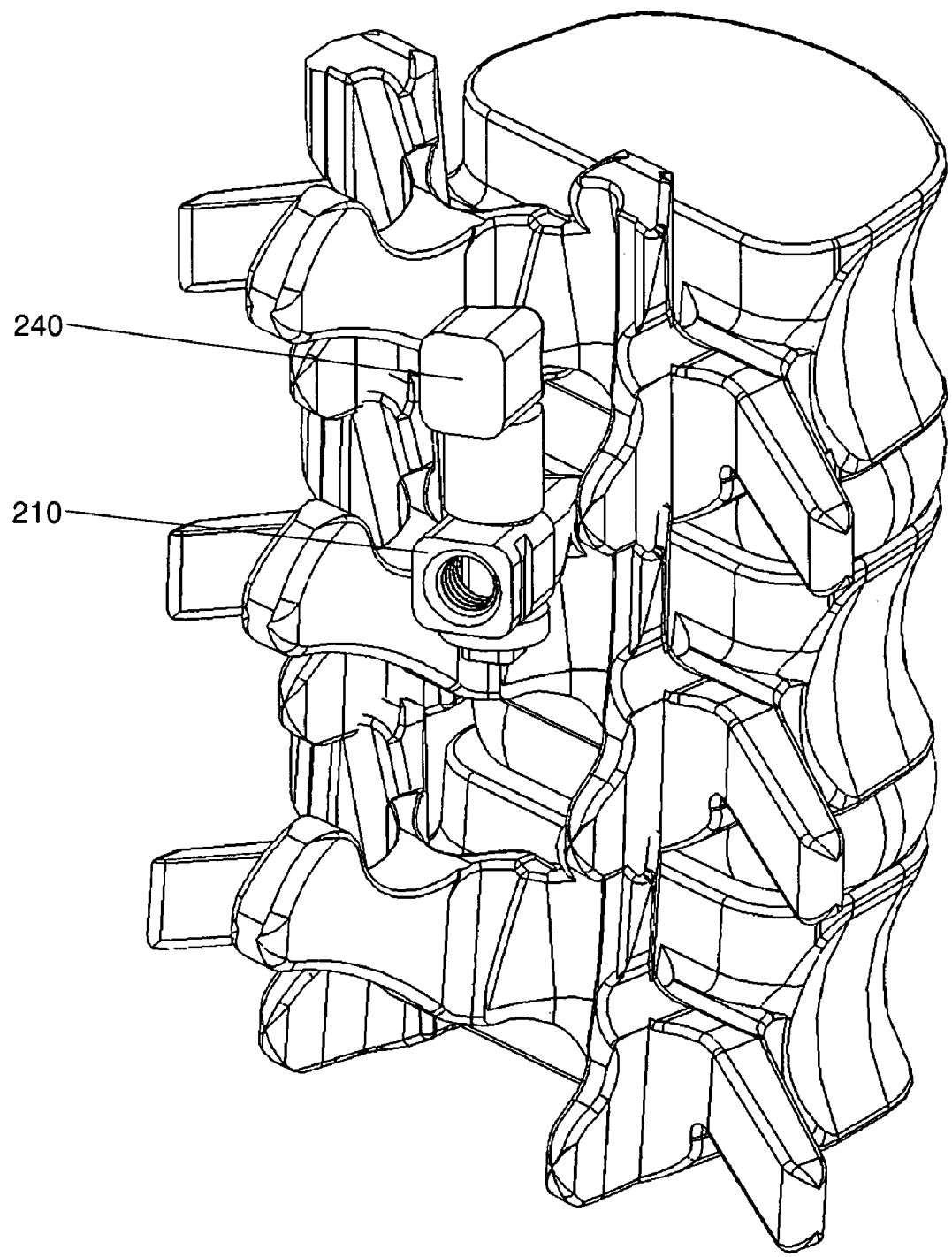
FIG. 15 is a elevation view of a posterior portion of a human spine showing one of the implant devices of FIG. 9 positioned between adjacent lamina.
Figure 16:
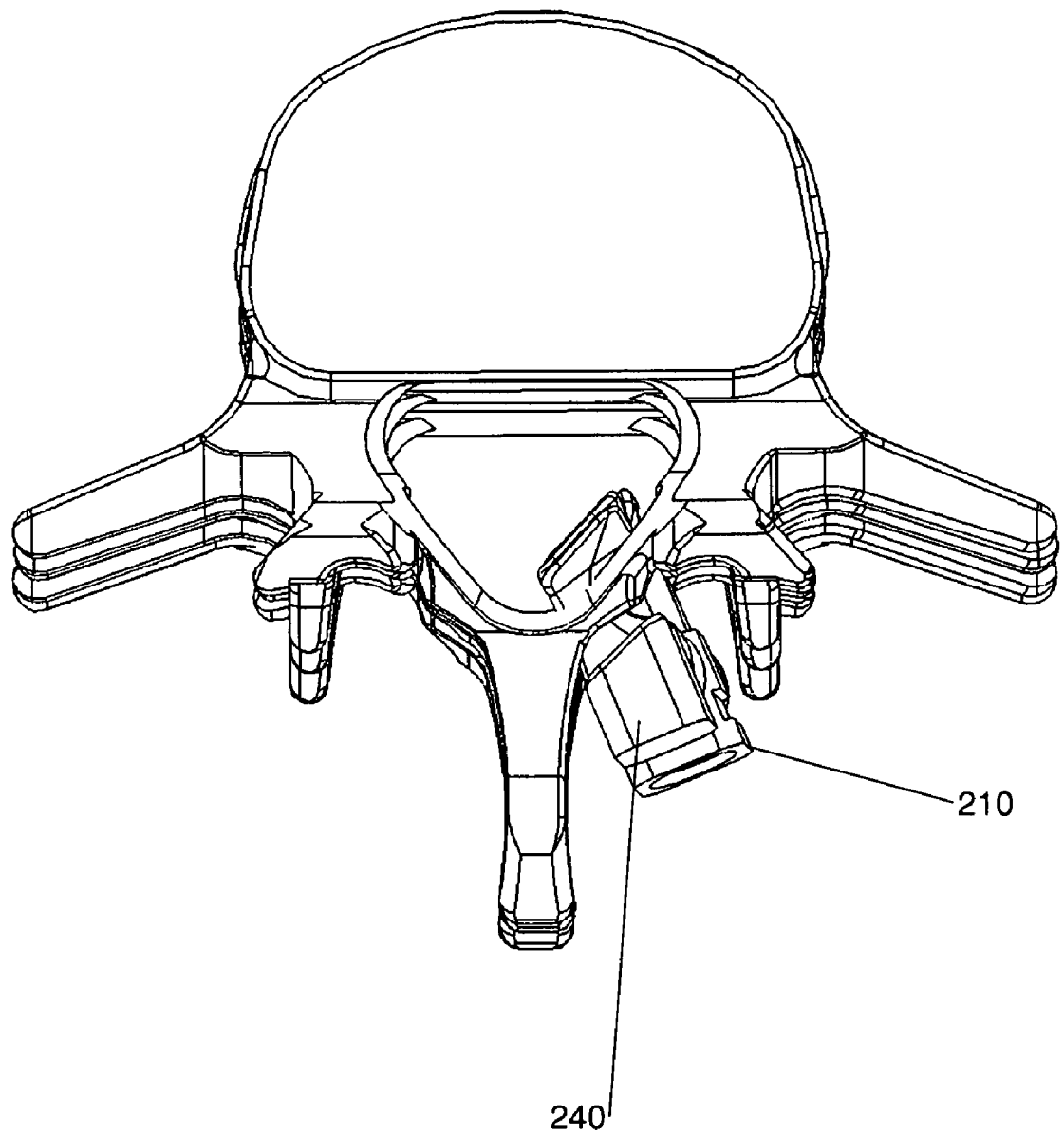
FIG. 16 is a top plan view of a human spine showing one of the implant devices of FIG. 9 positioned between adjacent lamina.
Figure 17:
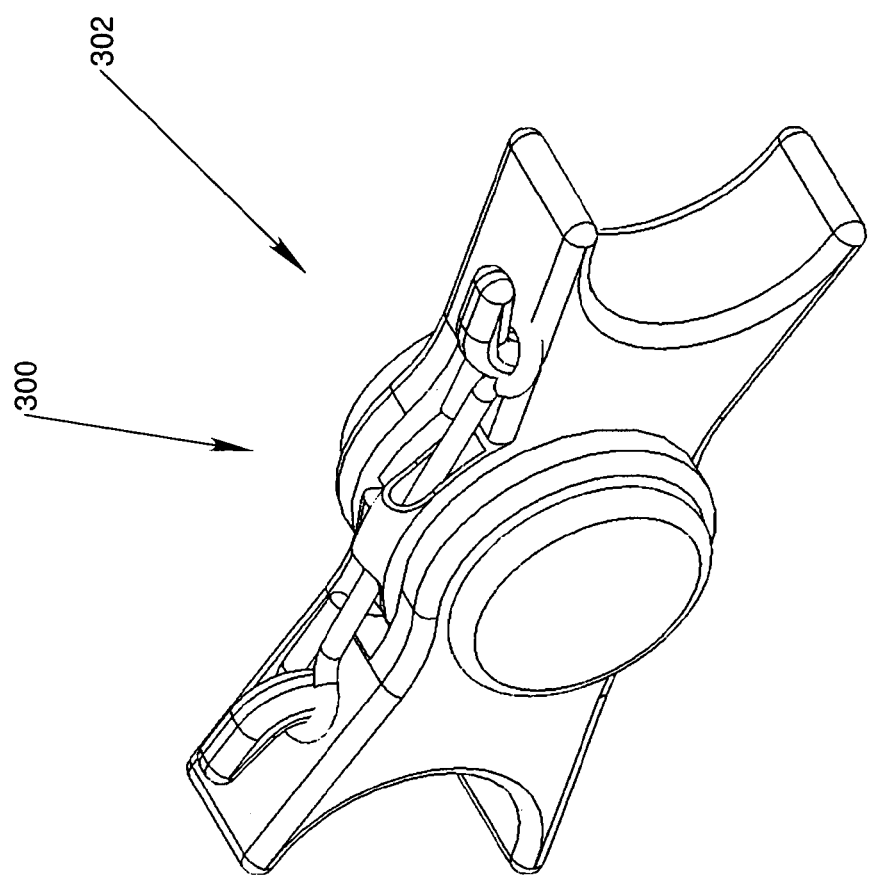
FIG. 17 is a perspective view of a spinal implant assembly according to a third form of the present invention.
Figure 18:
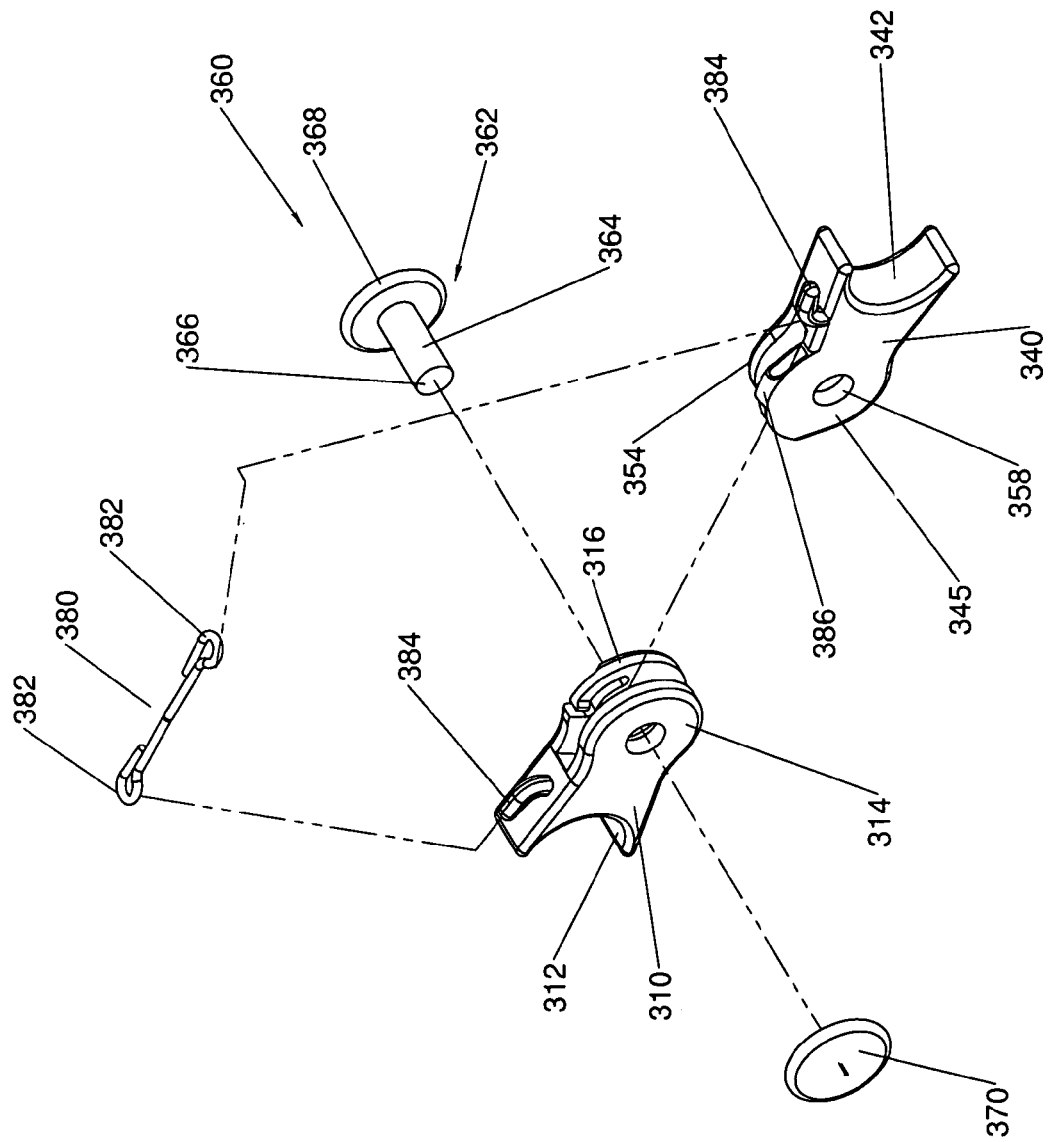
FIG. 18 is an exploded perspective view of the spinal implant assembly of FIG. 17.
Figure 19:
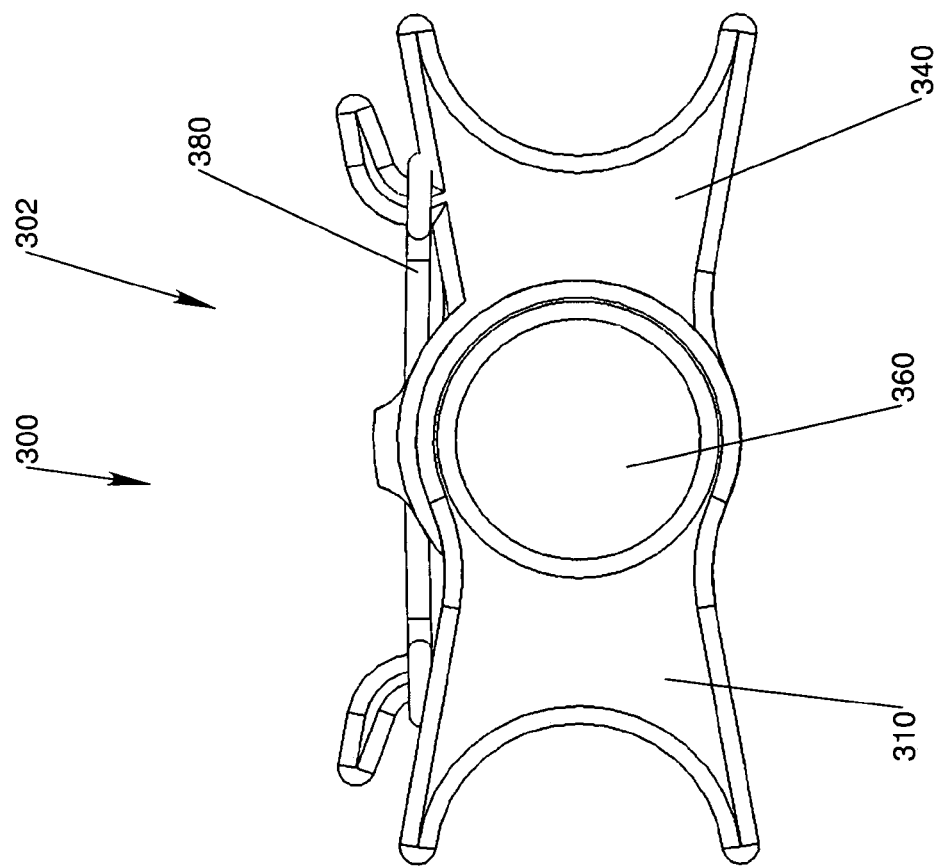
FIG. 19 is a side view of the spinal implant assembly of FIG. 17 showing the assembly in the operable orientation.
Figure 20:
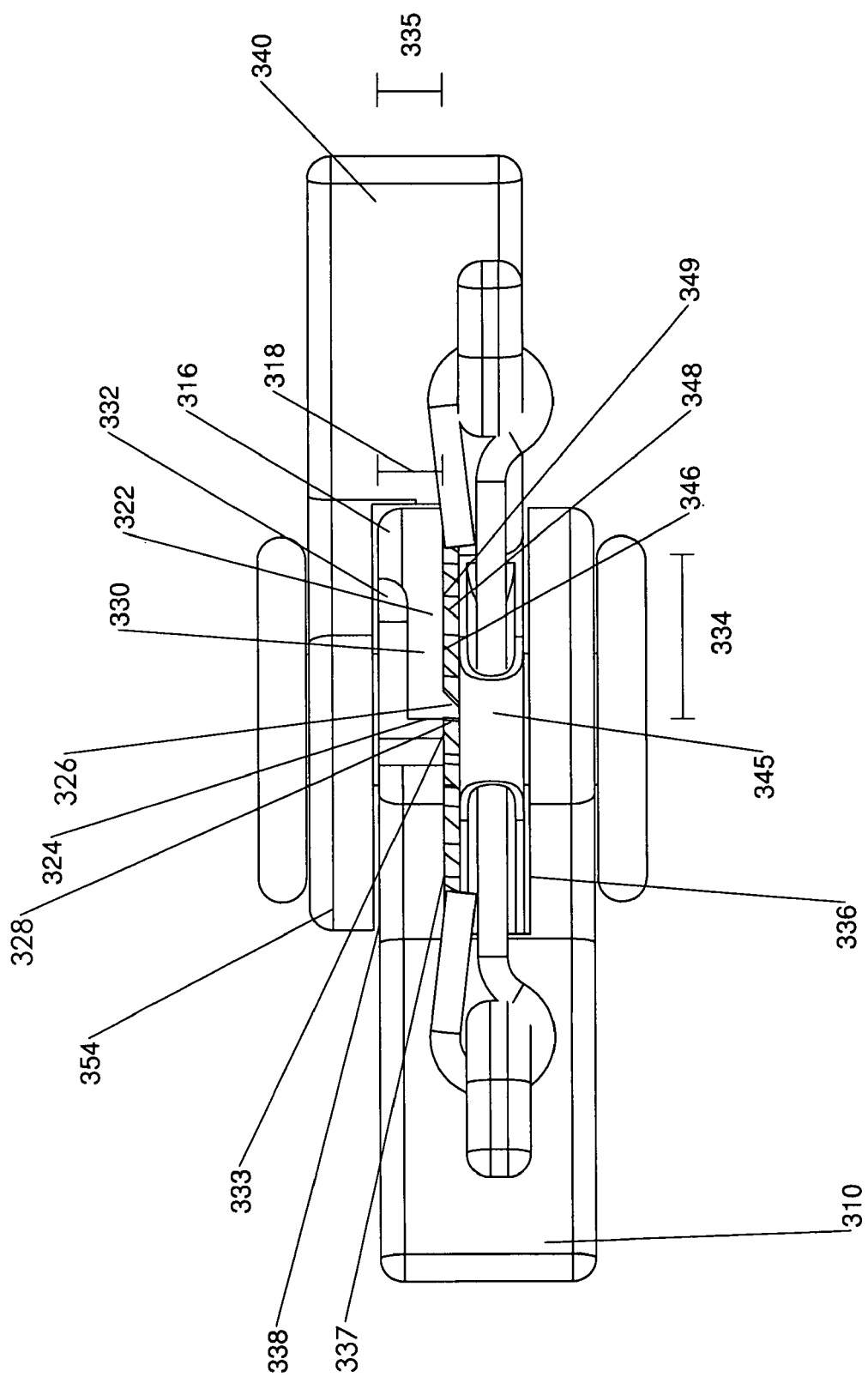
FIG. 20 is a top plan view of the spinal implant assembly of FIG. 17 showing the guide mechanism.
Figure 21:
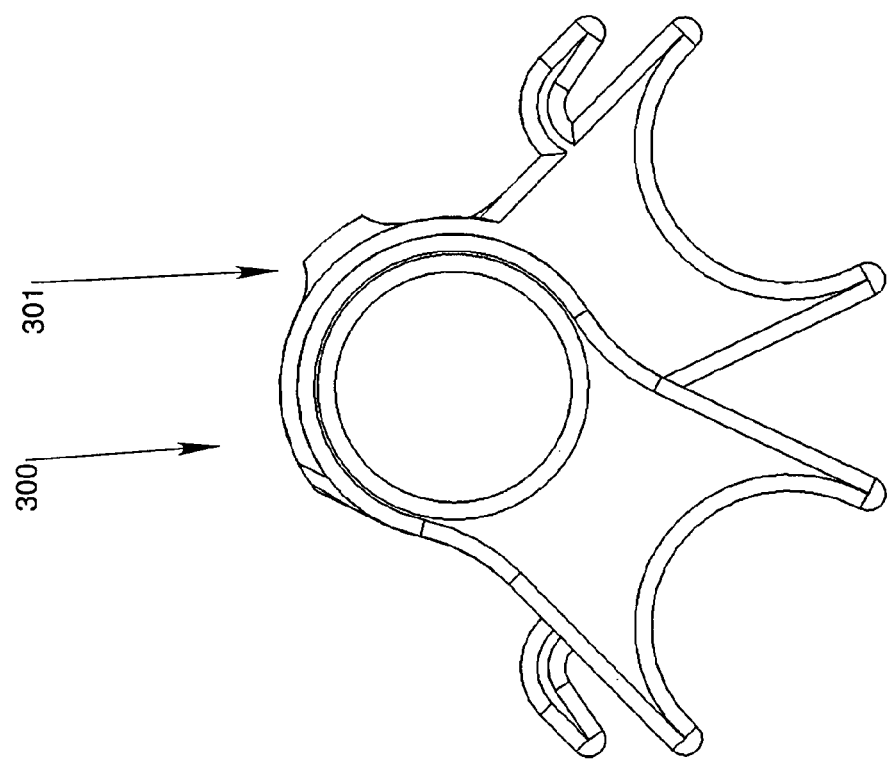
FIG. 21 is a side view of the spinal implant assembly of FIG. 17 showing the assembly in the inoperable orientation.

Upon translation of the spinal implant 200 to the operable orientation 202, the spinal implant includes a securing mechanism 280. The securing mechanism is configured to maintain a desired distance between the first and second body portion 210, 240, and can be accomplished by any known means, such as set screws, tapered sleeves, and pins. As shown in FIGS. 9 and 12, a spacer 282 configured to be inserted on the rod portion 270 can be inserted between the first and second body portions 210, 240. The spacer can be rigid or resilient depending on the application. Another exemplary securing mechanism 280 is shown in FIG. 14, where the securing mechanism 280 is a spring member 286. The spring member 286 includes a pair of sleeves 288 which are configured to be accepted on the rod portion 270. The sleeves 288 are connected by at least two arms 290 extending between the sleeves 288. In one embodiment, the arms 290 are rigid. In a preferred embodiment, the arms 290 are resilient in construction.

FIGS. 17-27 depict spinal implants 300, 400 according to a third form of the present invention. In one embodiment, a spinal implant 300, 400 includes a guide mechanism. The spinal implant 300, 400 includes a guide mechanism to transition the implant 300, 400 from the compact or inoperable orientation to the operable orientation. The guide mechanism is configured to permit the implant 300, 400 to transition in a predetermined direction, whether it is linear or rotational. Preferably, the guide mechanism includes a locking mechanism to restrict the movement in the predetermined direction. In one aspect, the locking mechanism allows for movement only toward the operable orientation and restricts movement toward the compact orientation. The locking mechanism can be any known locking mechanism, such as a ratcheting mechanism. Generally, the ratcheting mechanism includes teeth portions and corresponding teeth engagement portions. Preferably, the teeth portions have a camming surface which extends outwardly from the guide mechanism at an angle less than 90 degrees and a stop surface which extends from the guide mechanism at an angle of about 90 degrees. The teeth engagement portion includes corresponding second camming surfaces which correspond to the camming surface of the teeth portions to permit the second camming surface to shift along the second camming surface toward the operable orientation. The teeth engagement portion also includes a corresponding second stop surface which is configured to engage the stop surface of the teeth portion and restrict movement toward the compact orientation.

In one aspect of the third form of the invention, as shown in FIGS. 17-21, the spinal implant 300 includes a first engagement portion 310, a second engagement portion 340 and a pivot mechanism 360. The spinal implant 300 further includes an operable orientation 302 wherein the first and second engagement portions 310, 340 extend in opposite directions and a compact orientation 302 wherein the first and second engagement portions 310, 340 are adjacent one another.

The first engagement portion 310 includes a first seat portion 312 for engaging the lamina and a first arm 314 and second arm 316 extending opposite the first seat portion 312. The first arm 314 extends parallel to the second arm 316, each arm 312, 314 having a throughbore 320 extending therethrough for accepting a pivot mechanism 360 therein.

The second arm 316 includes a locking arm 322 having a teeth engaging portion 324 at the distal end 333 thereof. The teeth engaging portion 324 extends from the locking arm 332 toward the first arm 314 and beyond the inner surface 337 of the second arm 316. The locking arm 322 extends along the outer edge 338 of the second arm 316 and is defined by a cut-out portion 332 of the second arm 316 along the distal end 333 and length 334 of the locking arm 322. Further, the locking arm 322 is configured to be shifted away from the first arm 314 upon the application of force thereon to disengage the teeth engaging portion 324 from the teeth portion 346 allowing the spinal implant 300 to be transitioned back to the compact orientation 301. In one embodiment, the locking arm 322 has a width 335 that does not extend the width 318 of the second arm 316 thereby permitting the locking arm 322 to shift within the space defined by the width 318 of the second arm 316. In a further embodiment, the second arm 316 includes two or more locking arms 322 for engaging the teeth portions 346.

The second engagement portion 340 includes a second seat portion 342 for engaging the lamina, and first and second arms 345, 354 extending opposite the second seat portion 342. The first arm 345 extends parallel to the second arm 354, each arm 345, 354 having an throughbore 358 extending therethrough for accepting the pivot mechanism 360. The first arm 345 includes the teeth portion 346, which extend around a portion of the throughbore 358 and toward the second arm 354. In one embodiment, the teeth portion 346 extends circumferentially around the throughbore 358.

The first and second engagement portions 310, 340 are configured so that the first arm 345 of the second engagement portion 340 is receivable between the first and second arms 314, 316 of the first engagement portion 310, and the second arm 316 of the first engagement portion 310 is receivable between the first and second arms 345, 354 of the second engagement portion 340.

The pivot mechanism 360 extends through the throughbores 320, 358 in the first and second arms 312, 314, 345, 354 of the first and second engagement portions 310, 340. In one embodiment, the pivot mechanism 360 includes a first member 362 including a pivot pin portion 364 configured to extend through the throughbores 320', 358 and a head portion 368 configured to be larger than the throughbores 320, 358 to restrict movement of the rod portion 364. The pivot mechanism 360 further includes a securing member 370 to be attached at the distal end 366 of the pivot pin portion 364, such as a nut. Preferably, the throughbores 320, 358 and pivot pin portion 364 have smooth, annular surfaces to permit free rotation.

As the first and second engagement portions 310, 340 pivot around the pivot mechanism 360 from the compact orientation 301 toward the operable orientation 302, the camming surface 348 of the teeth portion 346 engage the corresponding second camming surface 326 of the teeth engaging portion 324 of the locking arm 322, thereby urging the locking arm 322 away from the teeth portions 346. When the teeth engaging portion shifts past the teeth portion 346 and thereby 324 ceases to be engaged with the teeth portion 346 the locking arm 322 shifts back toward the teeth portion 346.

The stop portions 328, 349 of the teeth portion 346 and teeth engaging portion 324 are configured to engage one another and block pivoting of the first and second engagement portions 310, 340 toward the compact orientation. As described above, in one embodiment the locking arm 322 is configured to disengage the teeth portion 346 upon the application of force to the locking arm 322 urging the locking arm 322 away from the teeth portion 346.

The spinal implant 300 can be further secured in the operable orientation 302 by any of the known methods. Further, in one embodiment the spinal implant 300 includes a band portion 380 extending from the first engagement portion 310 to the second engagement portion 340. Preferably, the band portion 380 is configured to be secured at each end, such as by a loop or hook portion 382. The securing mechanism further includes a pair of band hooks 384 extending from the first and second engagement portions 310, 340 configured to be engaged by the loop or hook portions 382. Further, one of the arms 312, 314, 345, 354 of the first and second engagement portion 310, 340, such as the first arm 345 of the second engagement portion 340, includes a sleeve 386 configured to accept the band 380 therein to guide and hold the band 380 in place while the spinal implant 300 is inserted and shifted to the operable orientation 302. The band 380 may be rigid or resilient pending the desired operation.

In another aspect of the third form of the invention, as shown in FIGS. 22-27, the spinal implant 400 includes a box portion 401, a secured hook 420, a movable hook 450 and a securing block 480.

The box portion 401 includes end walls 402, 403, sidewalls 407, a lower floor surface 404, and an open upper end 413. The lower floor surface 404 includes a first aperture 405 extending therethrough adjacent the end wall 402 for receiving secured hook 420 and a slot 406 extending across the lower surface floor 404 for receiving and accommodating movable hook 450.

Secured hook 420 includes a hook connector 421 and a hook portion 435 connected to the hook connector 421. The hook connector 421 includes a head 422 and an elongate body 427, the head 422 configured to be received within the box portion 401 and the elongate body 427 configured to extend through the first aperture 405. The elongate body 427 has a predetermined width 428 and depth 430 to allow the elongate body to extend through the first aperture 405 such that the elongate body 427 is rotatable and movable within the first aperture 405. Further, the head 422 is sized larger than the first aperture 405 so that the head 422 prevents the hook connector 421 from shifting completely through the first aperture 405.

The elongate body 427 extends a predetermined length 429 and includes an indentation portion 431 extending perpendicular the longitudinal axis 432 of the elongate body 427 and positioned a predetermined distance from the distal end of the elongate body 427. The elongate body 427 is configured to be accepted within an aperture 437 extending through the upper surface 436 of the hook 435. The hook 435 further includes an indention engaging portion 438 configured and sized to accept and engage the indention 431 of the elongate body 427, thereby securing the elongate body 427 with the hook 435.

The hook 435 further includes a curved end portion 439 and a seat 440 for engaging the lamina. In one embodiment, the hook includes a rear surface 441 having at least one indentation 442 therein for being contacted and accepting the rear edge 453 of the movable hook 450.

The movable hook 450 includes a hook portion 451 and a translating portion 465. The hook portion 451 includes a seat 452 for engaging lamina, a flat upper surface 455 configured to extend below the end wall 403 of the box portion 401 when the movable hook 450 is in the operable orientation, and a rear edge 453 having a convex shape 454. In one embodiment, the convex shape 454 of the rear edge 453 is configured to be accepted by the indentations 442 of the rear surface 441 of the secure hook 420.

The translating portion 465 of the movable hook 450 includes a first bottom surface 466, a second bottom portion 468, an upper surface 478, and a pair of end surfaces 477, 477a. The second bottom portion 468 extends a distance 467 from the first bottom surface 466, and is connected to the hook portion 451 by a rigid or pivotable connection. The distance 467 is predetermined based on the height of the head 422 of the secured hook 420. By having an elevated first bottom surface 466, the movable hook 450 is able to translate across the length of the box portion 401 because, in the compact orientation 498, the first bottom surface 466 is in contact with the upper surface 423 of the head 422, rather than the end surface 477 coming into contact with the head 422.

In one embodiment, the box portion 401 is configured to maintain the movable hook 450 within the box portion 401 once inserted. In one embodiment, the box portion 401 includes a pair of runners 410 extending along a portion of the upper edge of the sidewalls 407. The runners 410 are separated by a width 412 and include a tapered lower end 411. The width 412 between the runners 410 is predetermined to be less than the width of the translating portion 465, thereby maintaining the movable hook 450 within the box portion 401 when the translating portion 465 is located under the runners 410. The translating portion 465 includes tapered upper end edges to assist in the insertion of the movable hook 450 in the box portion 401.

Figure 22:
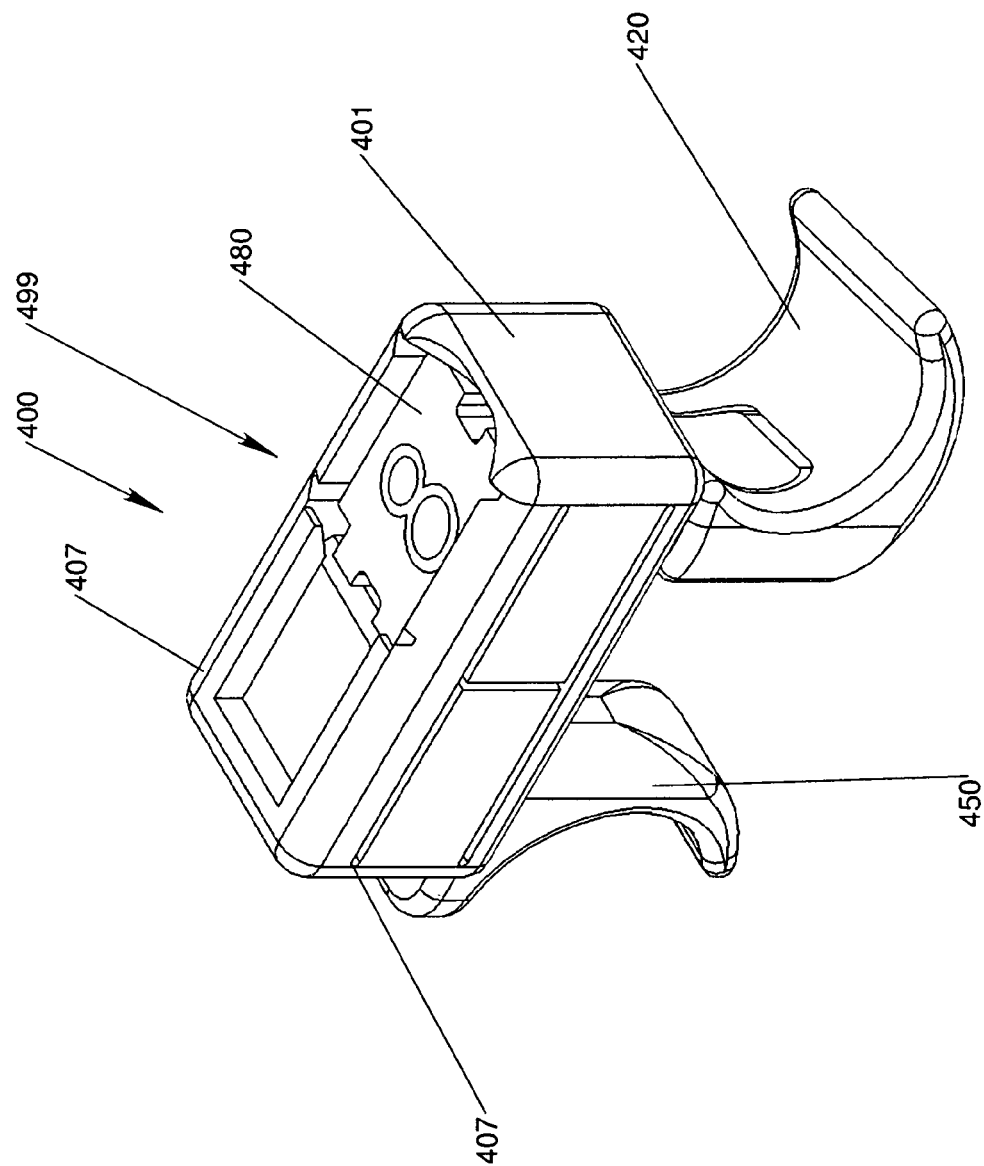
FIG. 22 is a perspective view of an alternate spinal implant assembly according to a third form of the present invention.
Figure 23:
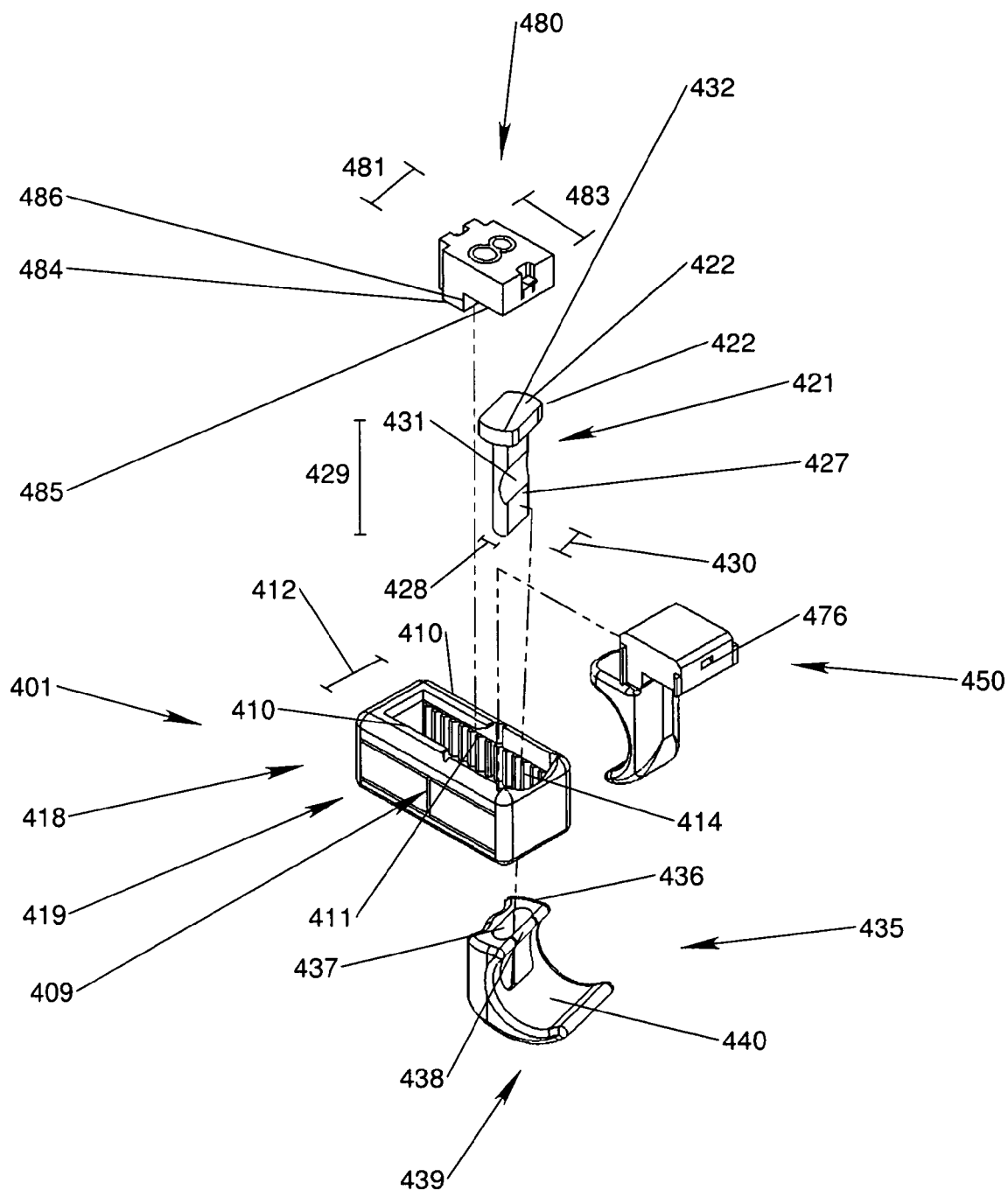
FIG. 23 is an exploded perspective view of the spinal implant assembly of FIG. 22.
Figure 24:
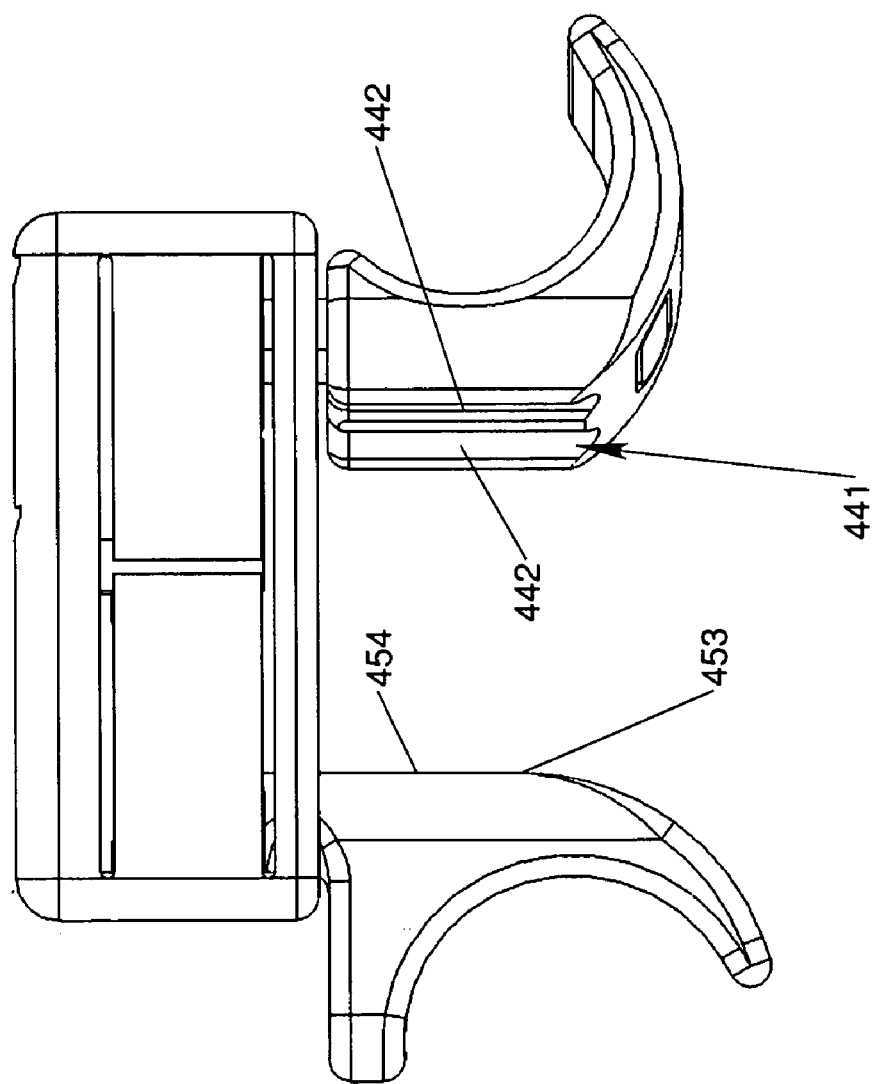
FIG. 24 is a is a side view of the spinal implant assembly of FIG. 22.
Figure 25:
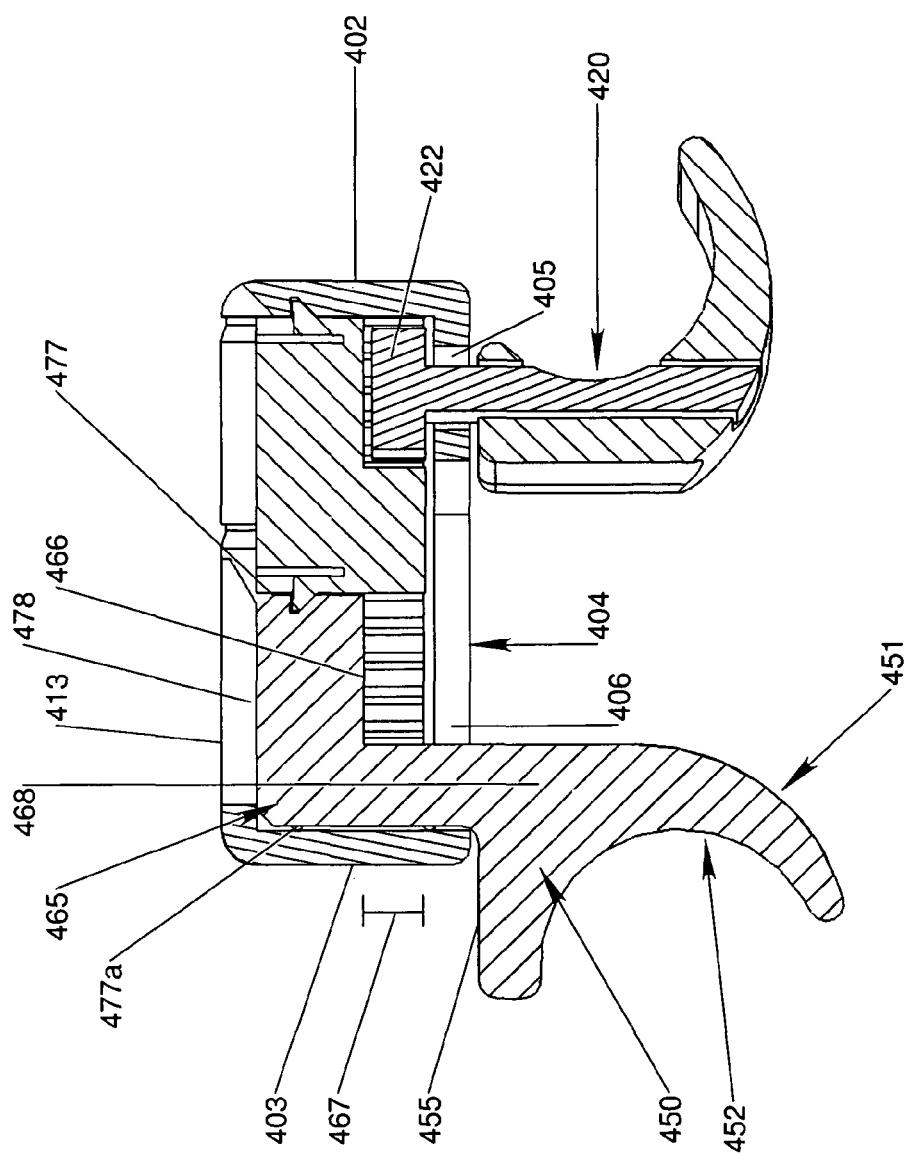
FIG. 25 is a partial cut-away side view of the spinal implant assembly of FIG. 22.
Figure 26:
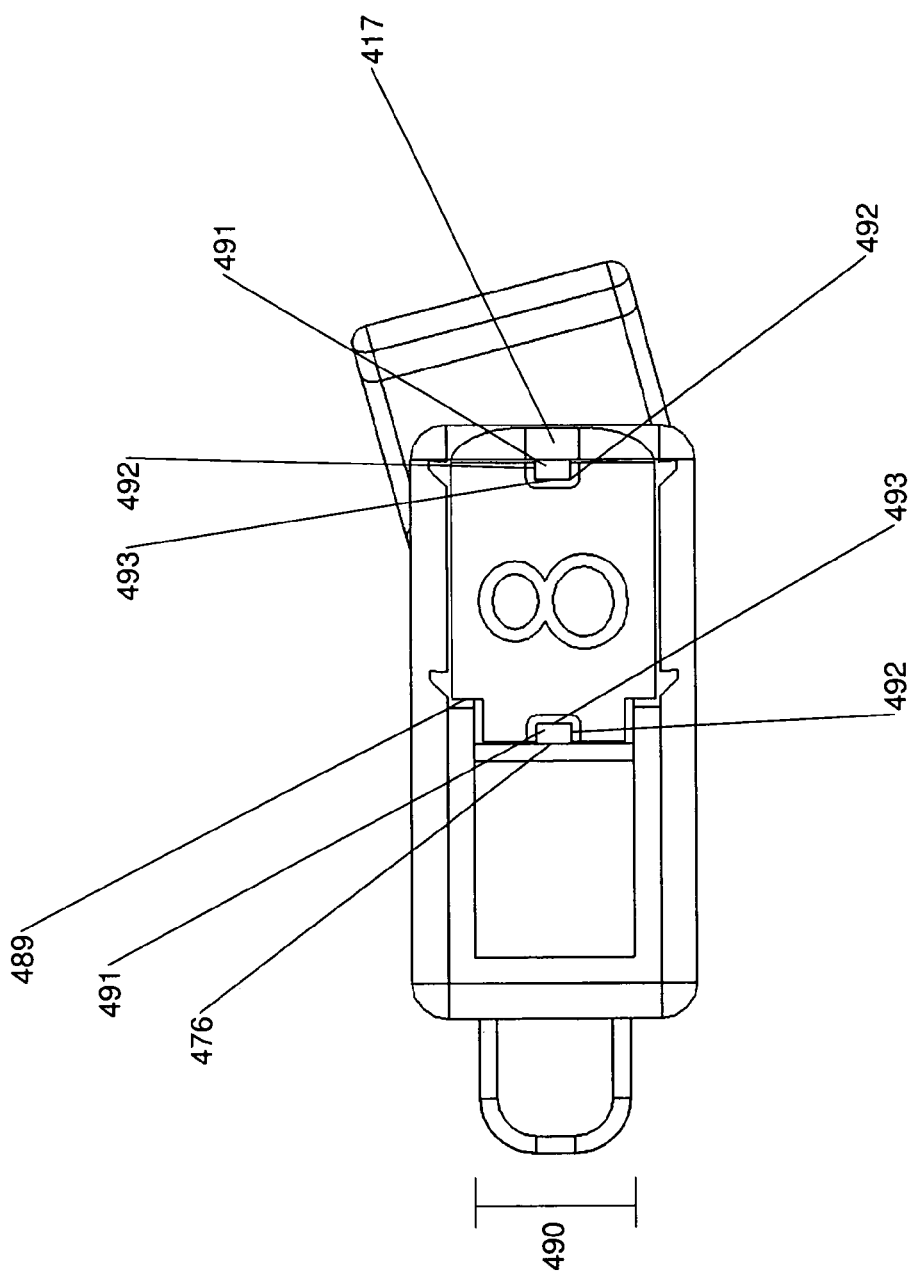
FIG. 26 is a top plan view of the spinal implant assembly of FIG. 22.
Figure 27:
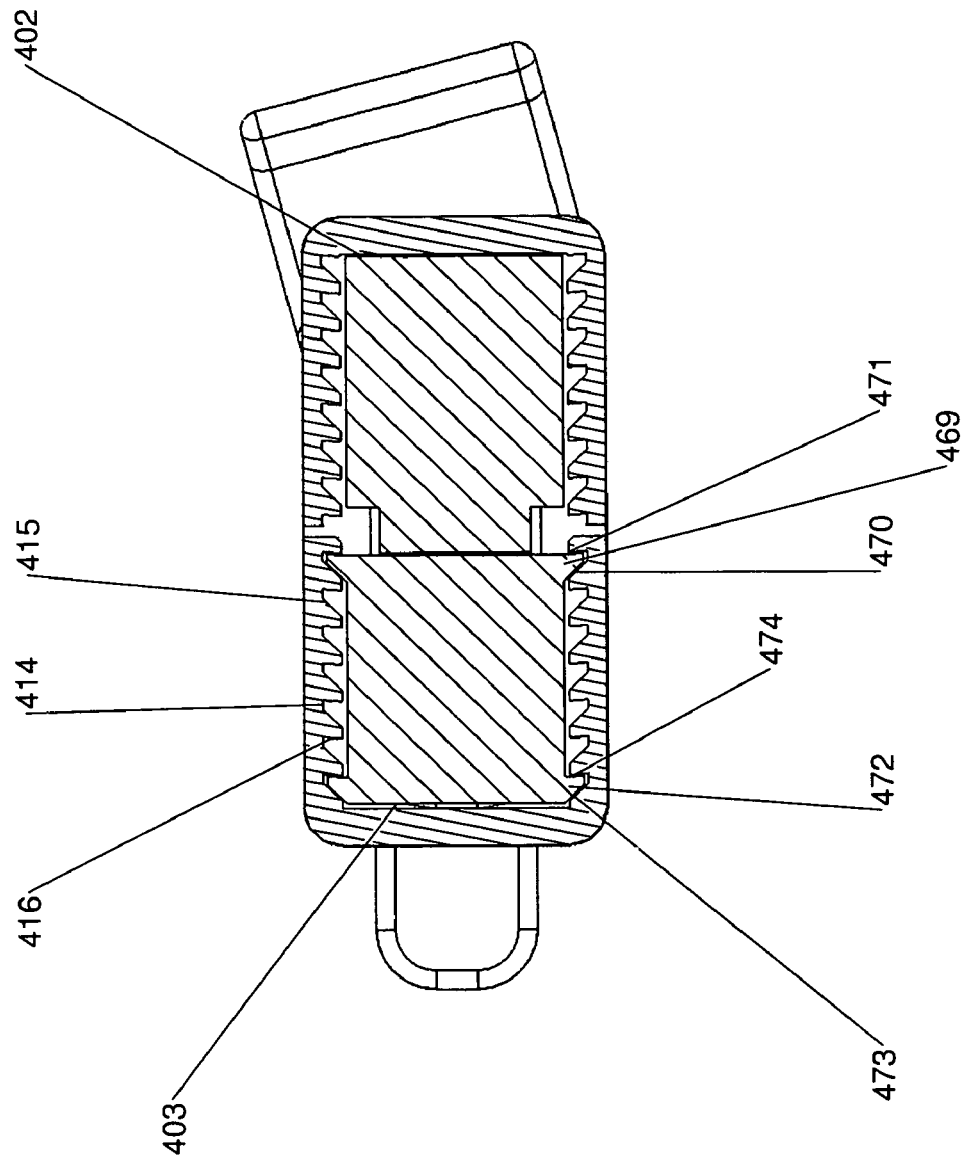
FIG. 27 is a partial cut-away top plan view of the spinal implant assembly of FIG. 22.
Figure 28:
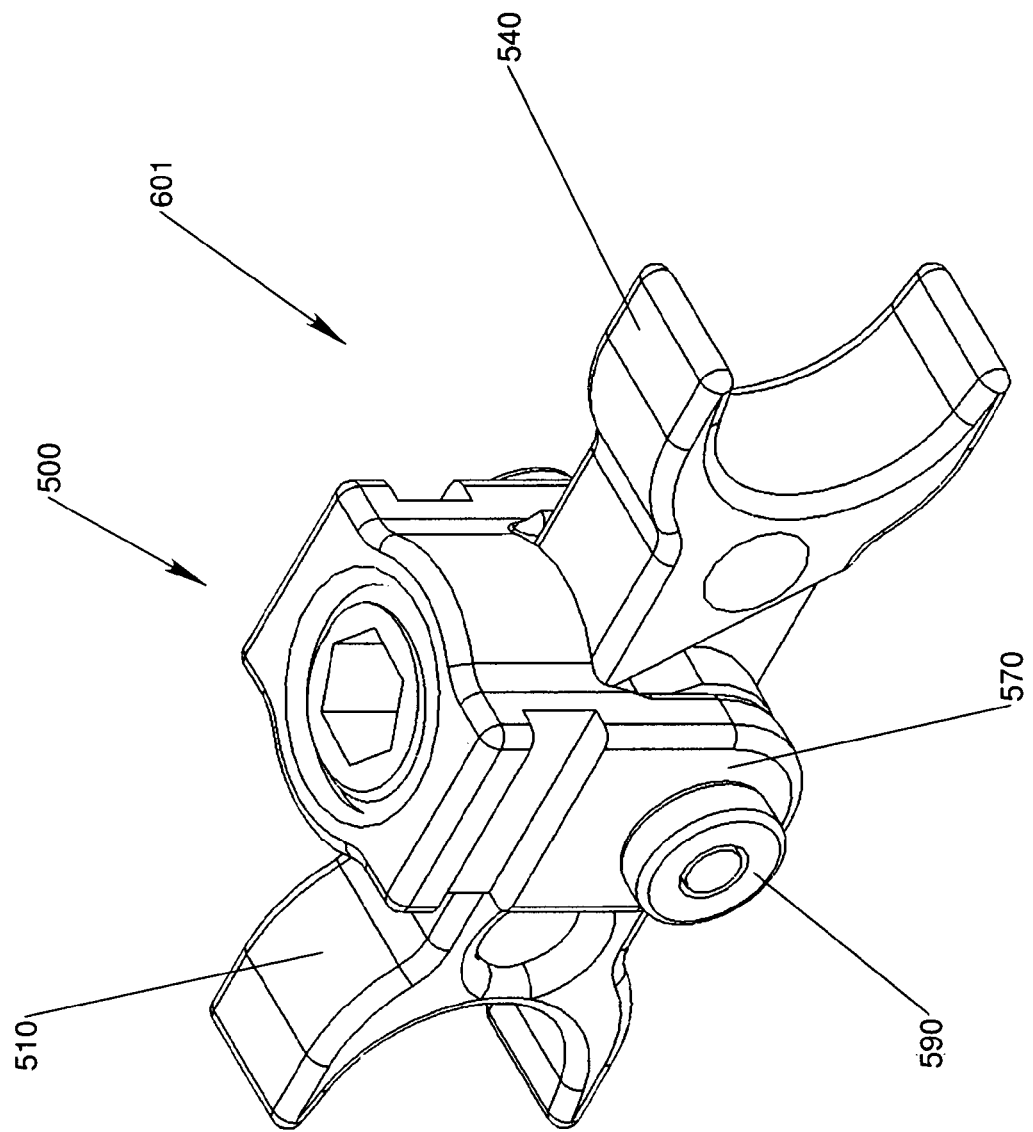
FIG. 28 is a perspective view of a spinal implant assembly according to a fourth form of the present invention.

The box portion 401 and movable hook 450 provide for the guide mechanism 418 and the locking mechanism 419. As shown in FIGS. 22-24, the box portion 401 includes sidewalls 407 having a pair of cutouts 409 on each sidewall 407 which are connected to the box portion 401 on one end, as shown in FIG. 24.

Further, on the inner surface 408 of the sidewalls 407 there are a plurality of teeth portions 414. The teeth portions 414 include a camming surface 415 facing the end wall 402 and a stop surface 416 facing the end wall 403. The stop surface 416 extends from the sidewall 407 at an angle of about 90 degrees, preferably 90 degrees. The camming surface 415 extends from the sidewalls 407 at an angle less than 90 degrees. In one embodiment, the camming surface 415 extends at an angle between 30 and 60 degrees. In addition, the movable hook 450 includes corresponding forward hook teeth portions 469 and rear hook teeth portions 472, each having a camming surface 470, 473 configured to face the end wall 403 and a stop surface 471, 474 configured to face end wall 402. The stop surface 471, 474 extends from the translating portion 465 at an angle of about 90 degrees, preferably 90 degrees. The camming surface 470, 473 extends from the translating portion 465 at an angle less than 90 degrees. In one embodiment, the cammings surface 470, 473 extends at an angle between 30 and 60 degrees.

As the movable hook 450 translates along the box portion 401, the camming surfaces 415 engage the hook camming surfaces 470, 473. The cutouts 409 are urged outward until the camming surfaces 470, 473 translate past the camming surface 415, wherein the cutouts 409 shift to their natural position. This process is continued until the movable hook 450 is in the desired operable orientation 499.

When the movable hook 450 and secured hook 420 are under load conditions, such as when inserted between adjacent lamina, the stop surfaces 416 will engage the stop surfaces 471, 474. The engagement of the stop surfaces 416 with the stop surfaces 471, 474, will resist translation of the movable hook 450 toward the compact orientation 498.

In one embodiment the cutouts 409 can be urged outwardly by an external application of force to permit the securing surfaces 416 to bypass the securing surfaces 471, 474 and allow the movable hook 450 to be translated to the compact orientation 498.

The securing block 480 is configured to be inserted into the box portion 401 when the movable hook 450 is in the operable orientation 499 to further resist translation of the movable hook 450 toward the compact orientation 498. The securing block 480 has a width 481 greater than the space 412 between the runners 410 of the box portion 401. The securing block 480 also has a predetermined length 483 based on the predetermined operable orientation 499 of the movable hook 450. An example of length 483 includes the range of about 1 mm to about 8 mm. In addition, the securing block 480 includes a first bottom surface 484, a second bottom surface 485 and a bottom step 486 therebetween. The bottom step 486 is configured to permit the first bottom surface 484 to contact the floor 404 of the box portion 401 while also allowing the second bottom surface 485 to contact the upper surface 423 of the head 422 of the secured hook 420. The length 483 of the securing block 480 is sized so that the securing block 480 engages the end wall 402 of the box portion 401 and the end surface 477 of the translating portion 465 of the movable hook 450.

The securing block 480 further includes a pair of tapered bosses 491 extending from either end of the securing block 480 to secure the securing block 480 between the movable hook 450 and the end wall 402 of box portion 401. The tapered bosses 491 are preferably cut-out on the sides 492 and rear 493 to permit limited movement of the tapered bosses 491. The end wall 402 of the box portion 401 includes a corresponding detent 417 to accept one tapered boss 491, while the end surface 477 of the movable hook 450 has a similar corresponding detent 476 to accept the other tapered boss 491.

In one embodiment, the sidewalls 487, 488 include a pair of steps 489 therein to aid in insertion of the securing block 480. The steps 489 have a width 490 less than the width 412 between the runners 410 of the box portion 401. Therefore, the steps 489 permit the insertion of a securing block 480 having a length 483 which extends from the end wall 402 beyond the start of the runners 410.

FIGS. 28-33 depict a spinal implant 500 according to a fourth form of the present invention. The spinal implant 500 includes a vertebral engaging arm 510, a second vertebral engaging arm 540, a generally U-shaped body 570 and a pivoting mechanism 590.

The first vertebral engaging arm 540 includes a first engagement portion 520, a spacer portion 511 and a pair of spaced arms 530. The first engagement portion 520 includes a semicircle-shaped seat 521 for contacting and engaging one of the adjacent lamina. The first engagement portion 520 extends from a distal end 512 of the spacer portion 511. In one embodiment, the spacer portion 511 includes an insertion throughbore 514 extending across the width 516 of the spacer portion 530 and configured to be engaged by an inserter tool. Preferably, the spacer portion 520 further includes a first tapered portion 515 surrounding the insertion throughbore 514 to aid in engaging the insertion tool.

Extending from the proximal end 513 of the spacer portion 511 are the pair of spaced arms 530. The spaced arms 530 have an annular distal end 531 and are offset from the spacer portion 511 such that the arms 530 extend beyond the width 516 of the spacer portion 511. The spaced arms 530 have a pair of corresponding pivot throughbores 533 configured to accept the pivot mechanism 590 therein. In a preferred embodiment, the throughbores 533 include a tapered edge therearound.

The second vertebral engaging arm 540 includes a second engagement portion 541, a spacer portion 545 and a centered arm 558. The second engagement portion 541 includes a semicircle-shaped seat 542 for contacting and engaging the other of the adjacent lamina. The second engagement portion 541 extends from a distal end 546 of the spacer portion 545. The spacer portion 545 includes an insertion throughbore 549 extending across the width 548 of the spacer portion 545 and configured to be engaged by an inserter tool. The spacer portion 545 further includes a first tapered portion 550 surrounding the insertion throughbore 549 to aid in engaging the insertion tool.

Figure 29:
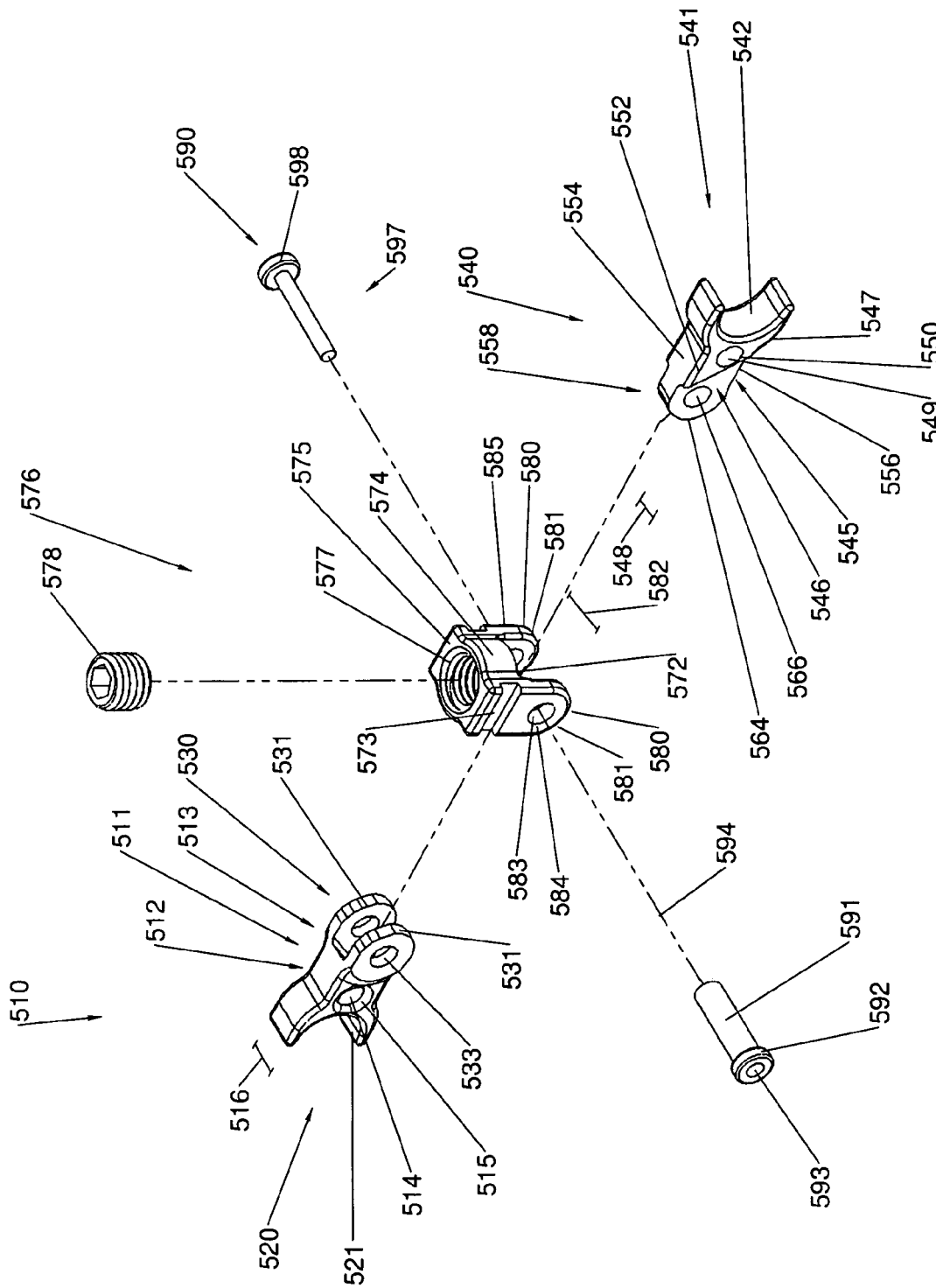
FIG. 29 is an exploded perspective view of the spinal implant assembly of FIG. 28.
Figure 30:
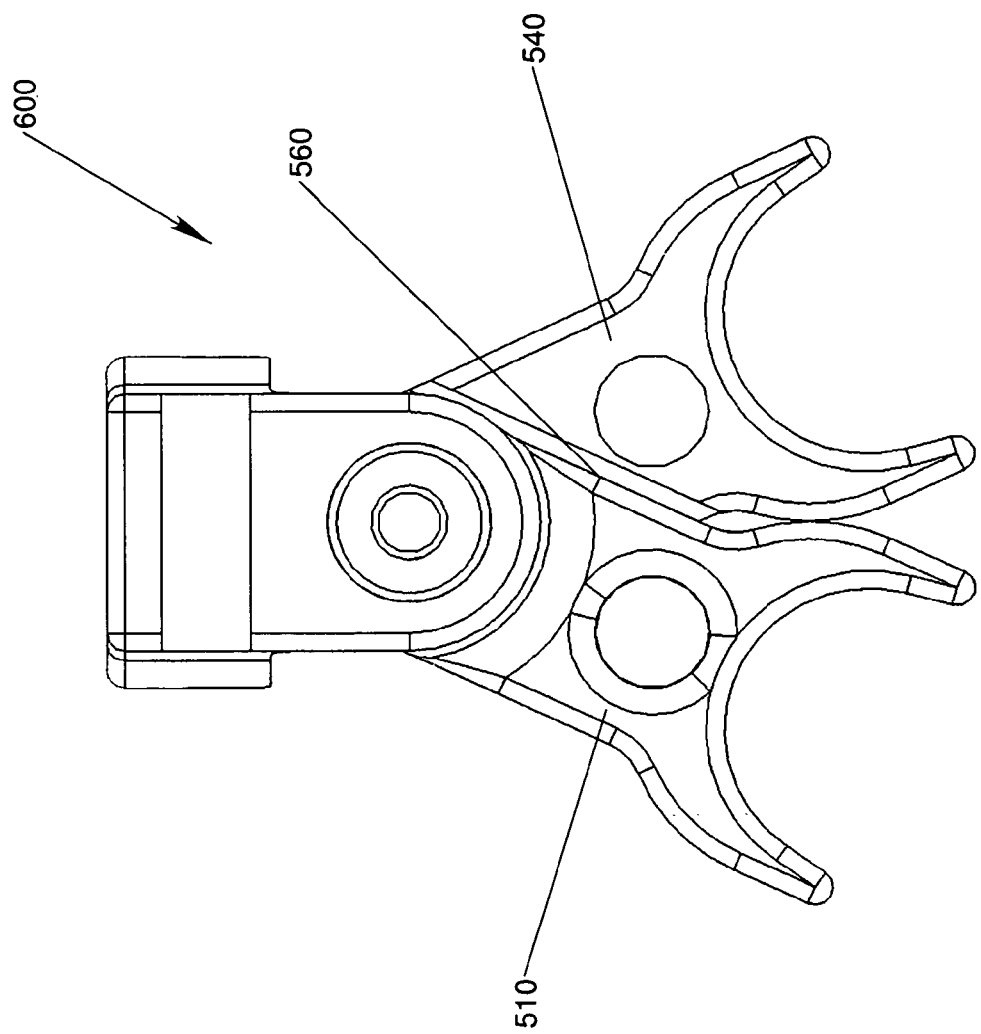
FIG. 30 is a side view of the spinal implant assembly of FIG. 28 showing the implant in the inoperable orientation.
Figure 31:
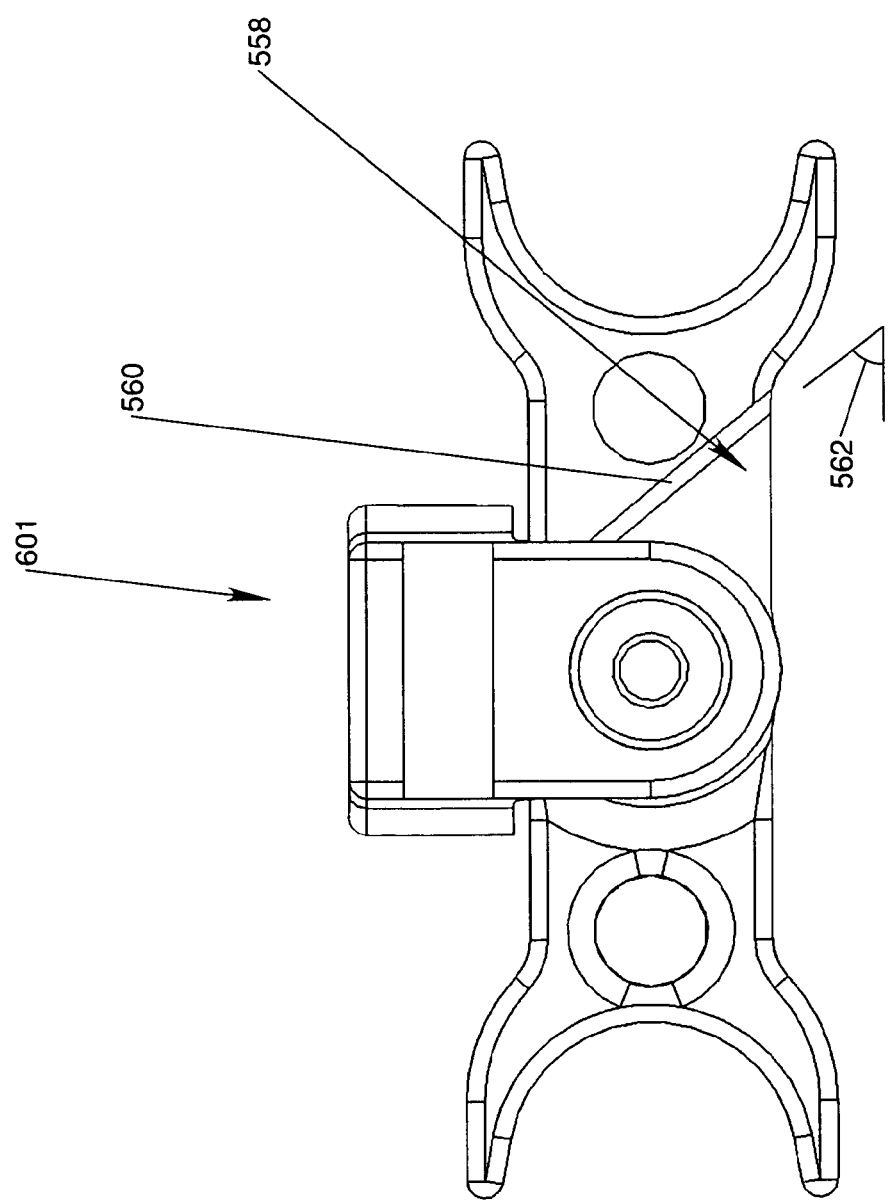
FIG. 31 is a side view of the spinal implant assembly of FIG. 28 showing the implant in the operable orientation.
Figure 32:
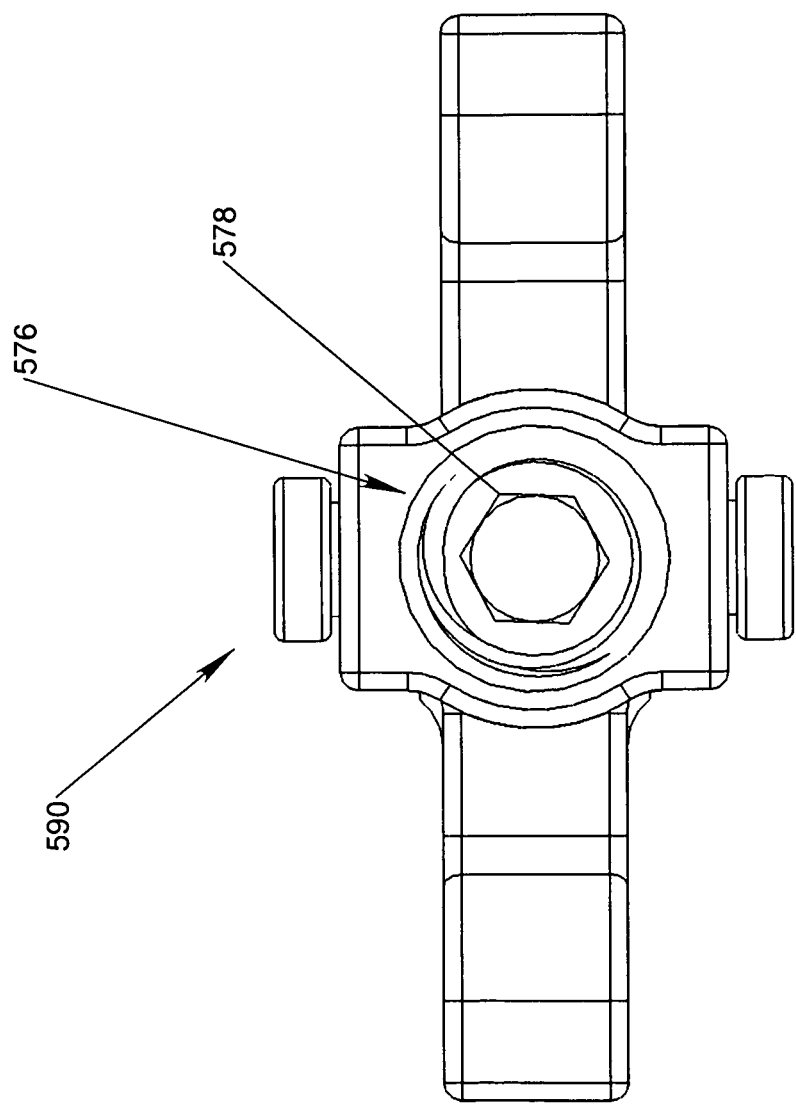
FIG. 32 is a top plan view of the spinal implant assembly of FIG. 28.
Figure 33:
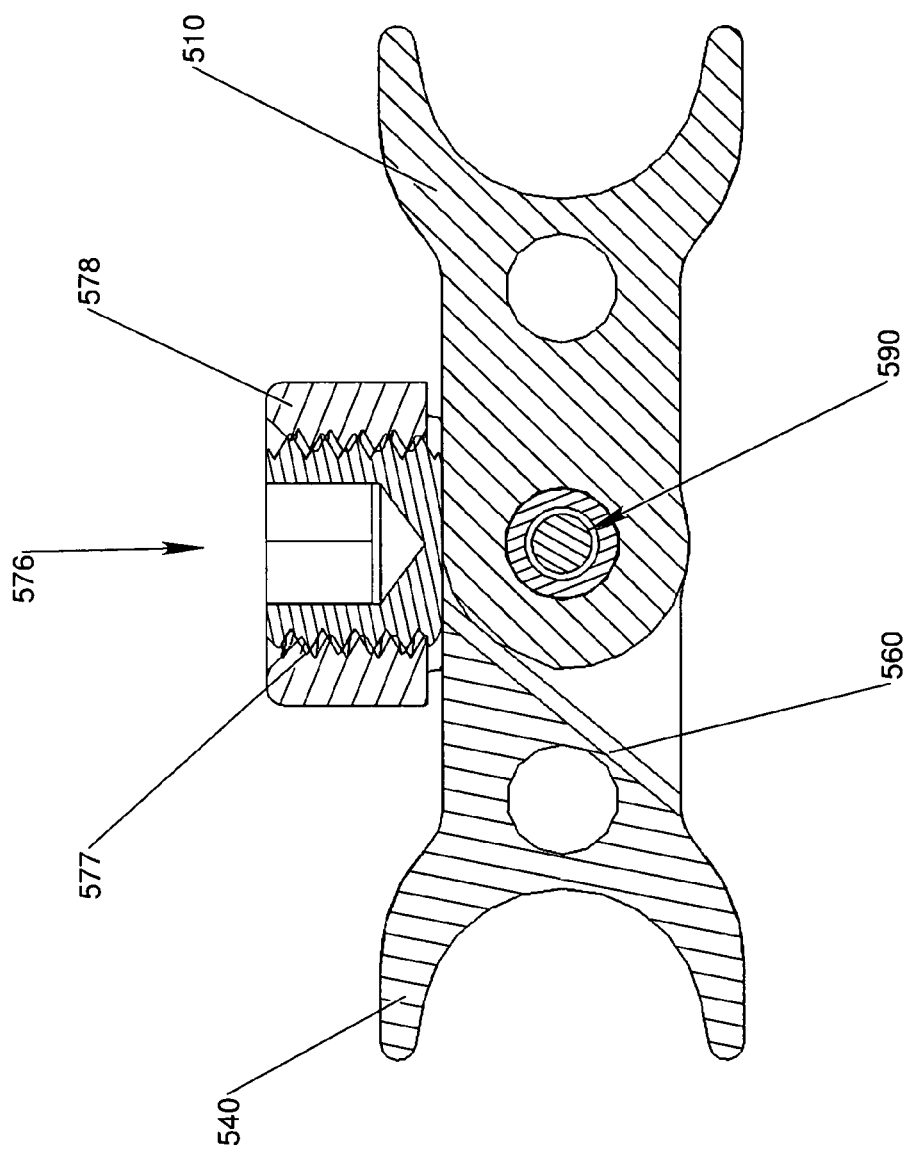
FIG. 33 is a partial cut-away side view of the spinal implant assembly of FIG. 28.
Figure 34:
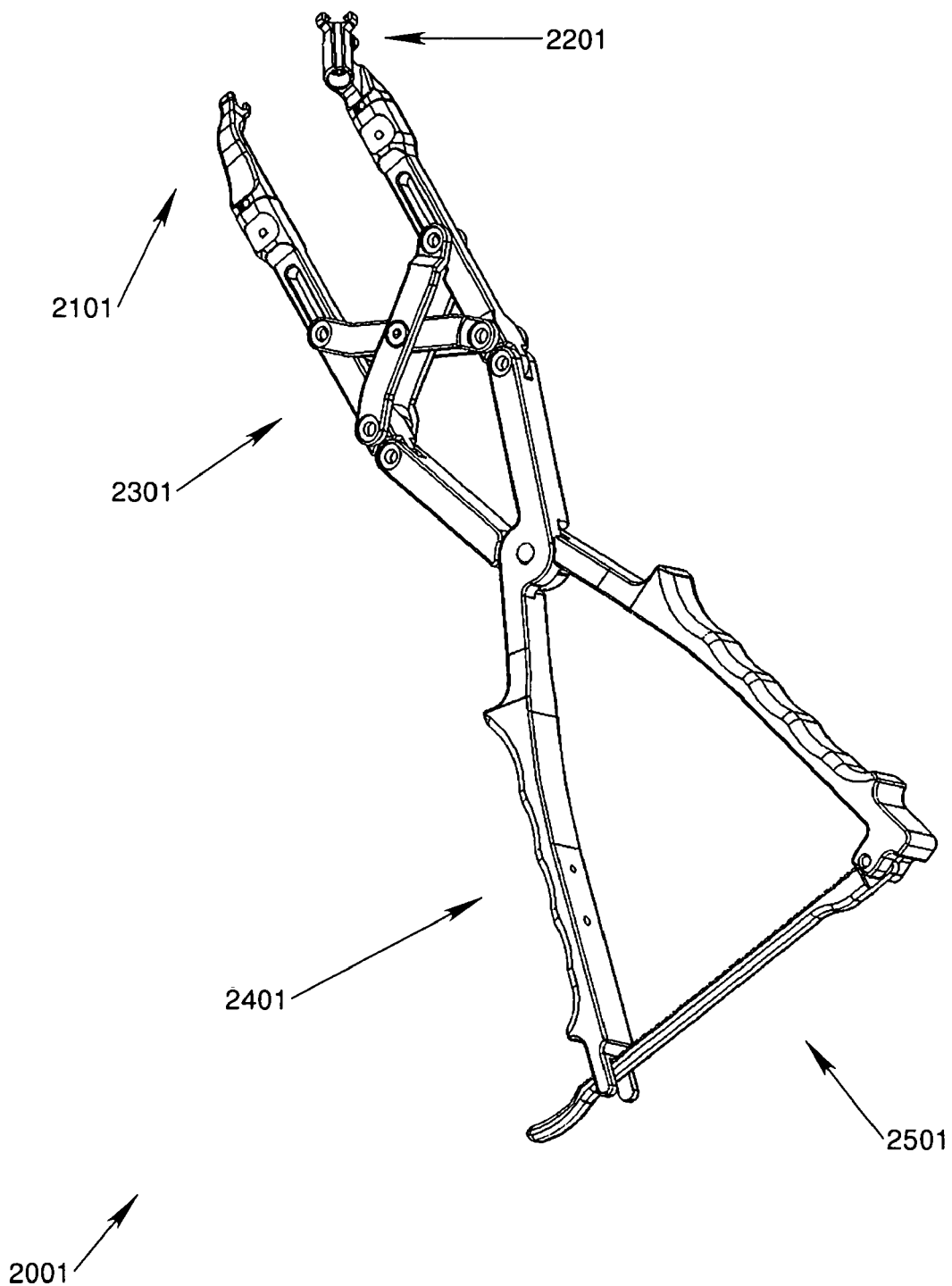
FIG. 34-52 are perspective views of the implant tools for inserting a spinal implant assembly of FIGS. 1, 9, 17, 22, and 28.
Figure 35:
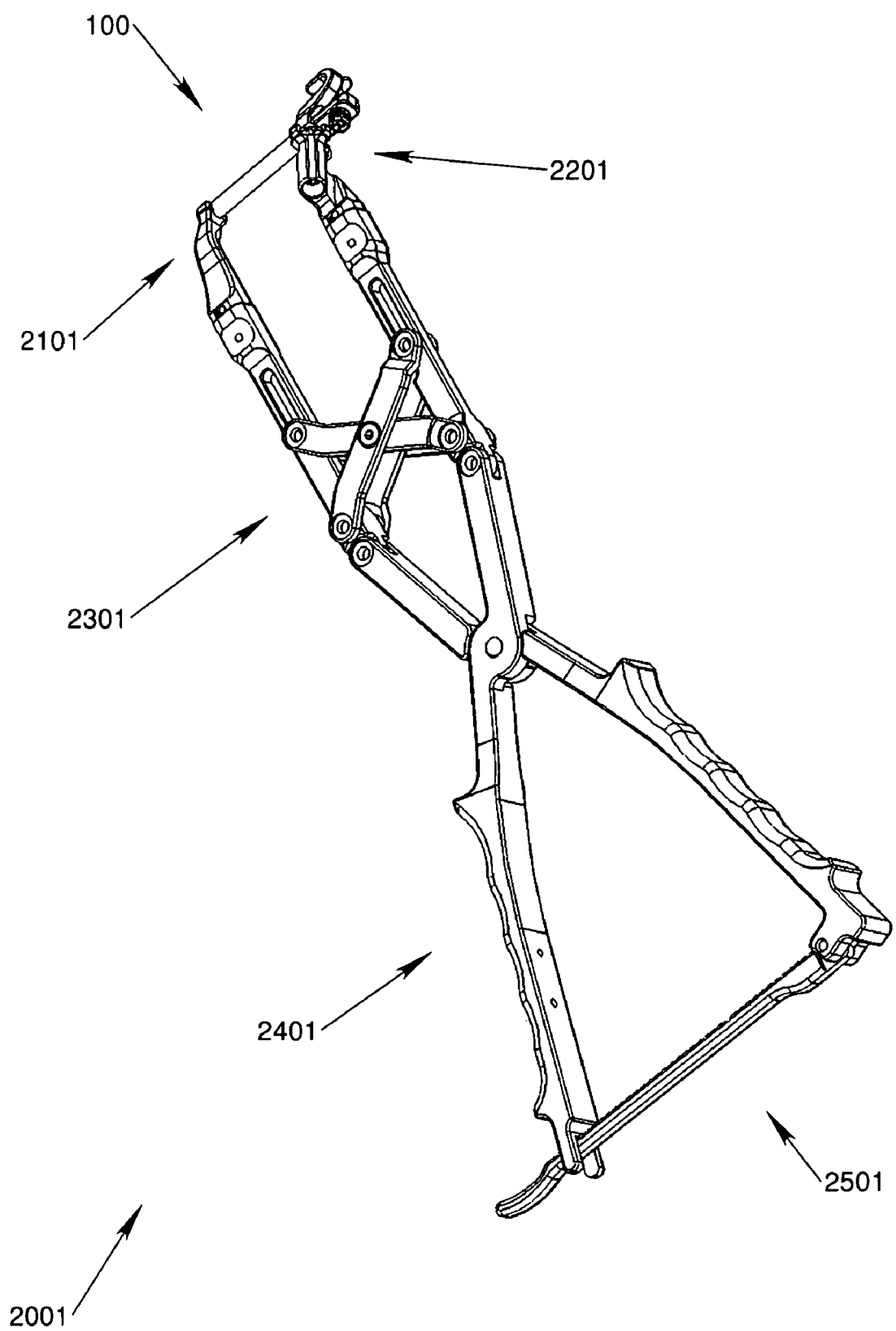
Figure 36:
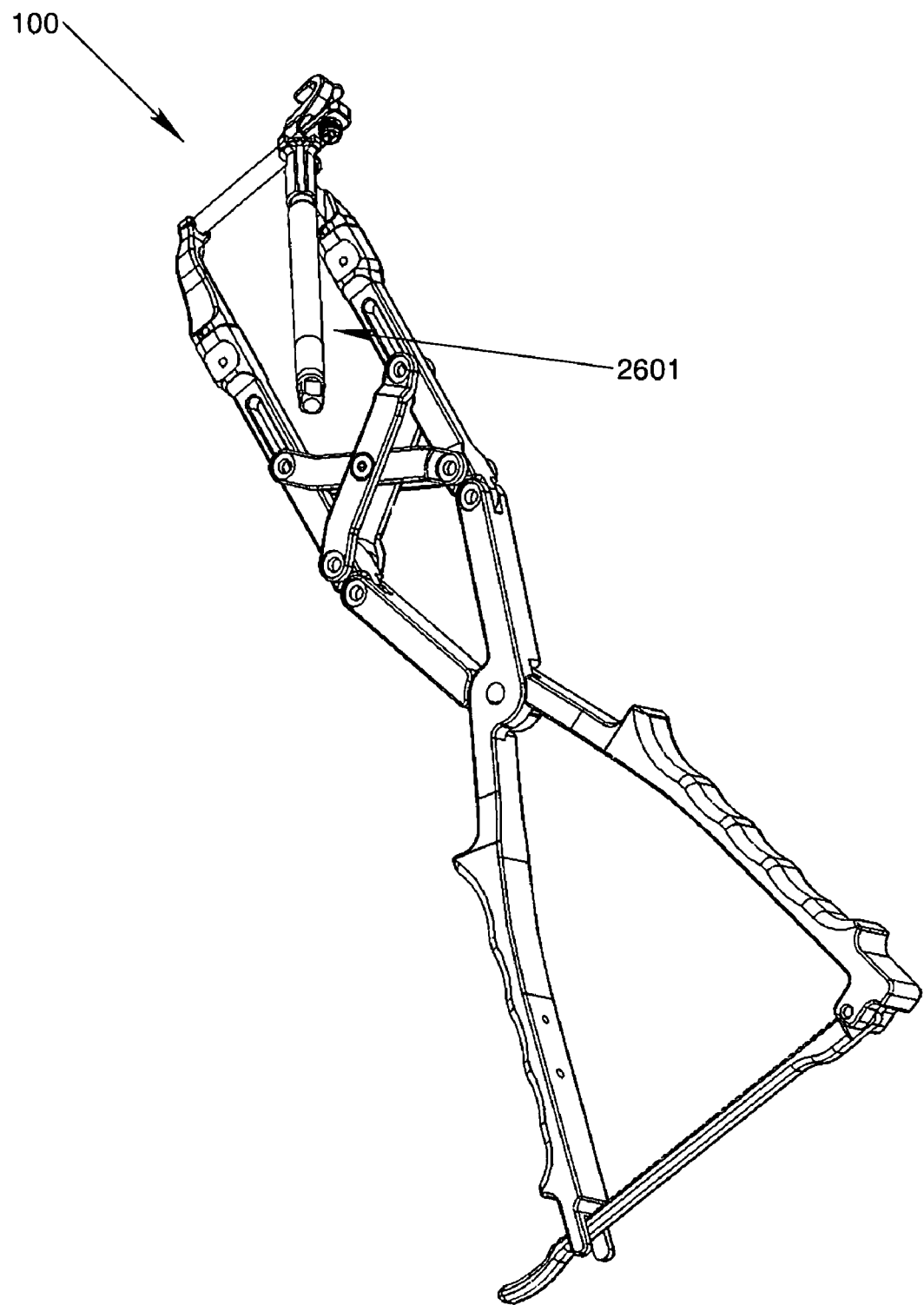
Figure 37:
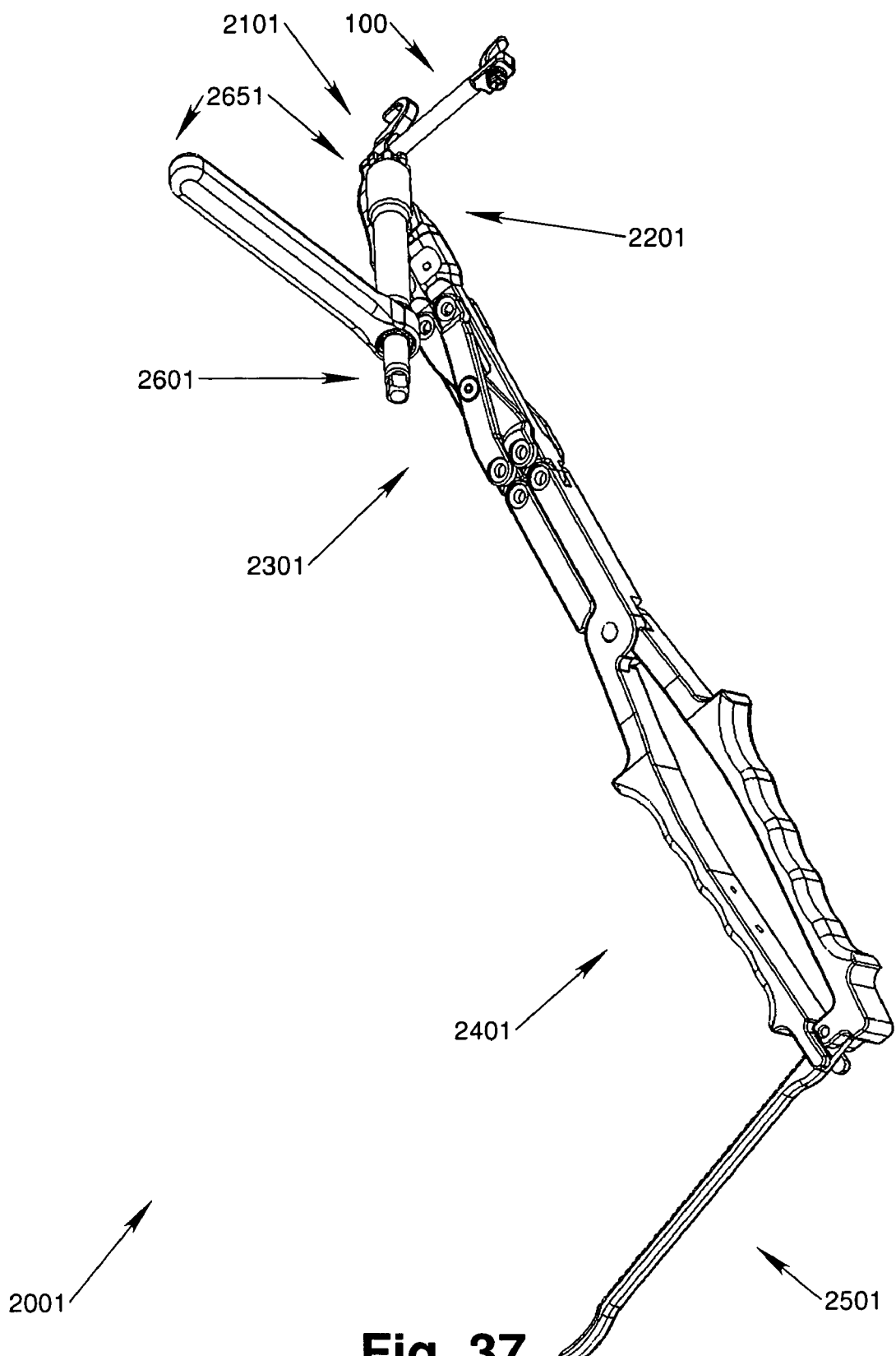
Figure 38:
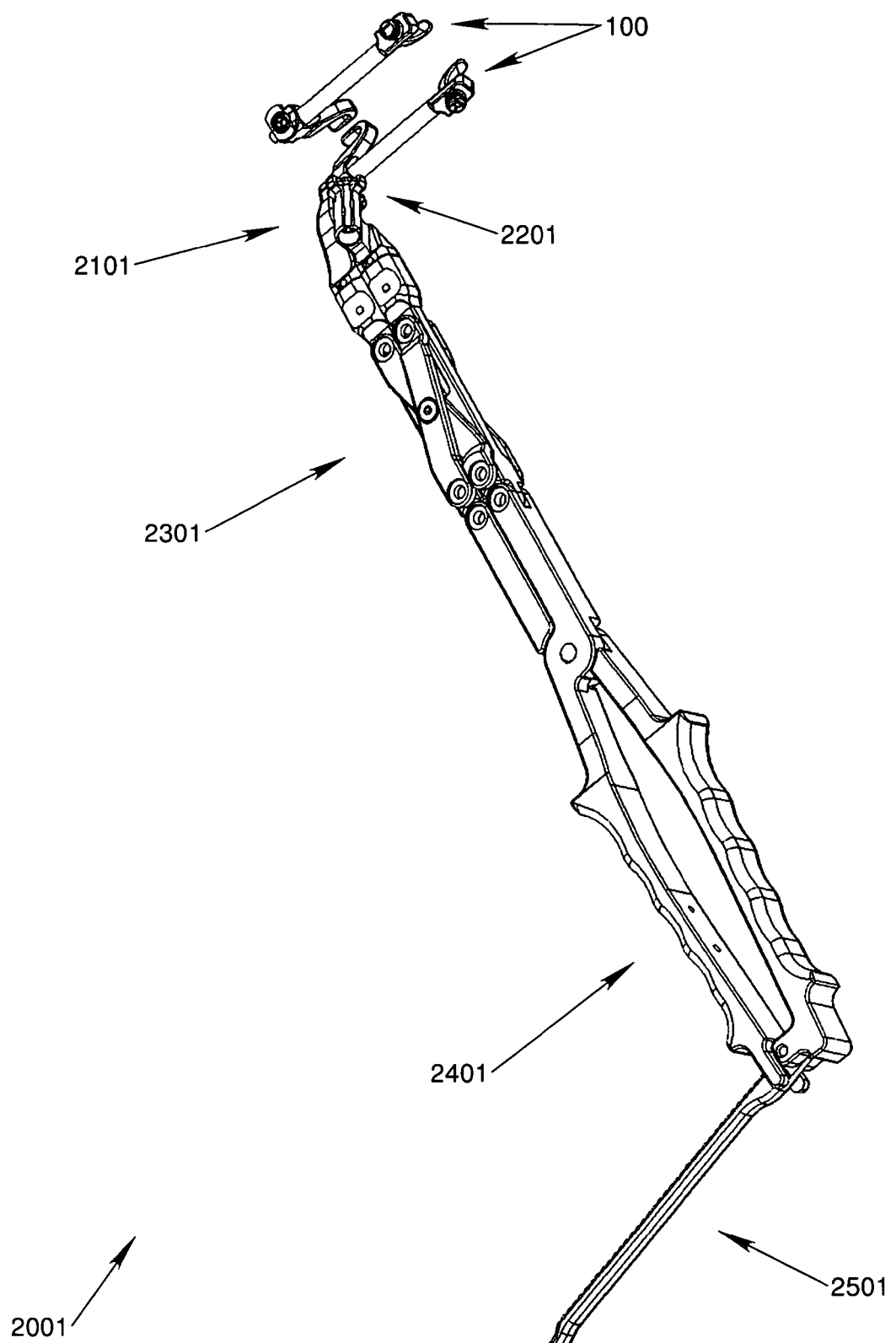
Figure 39:
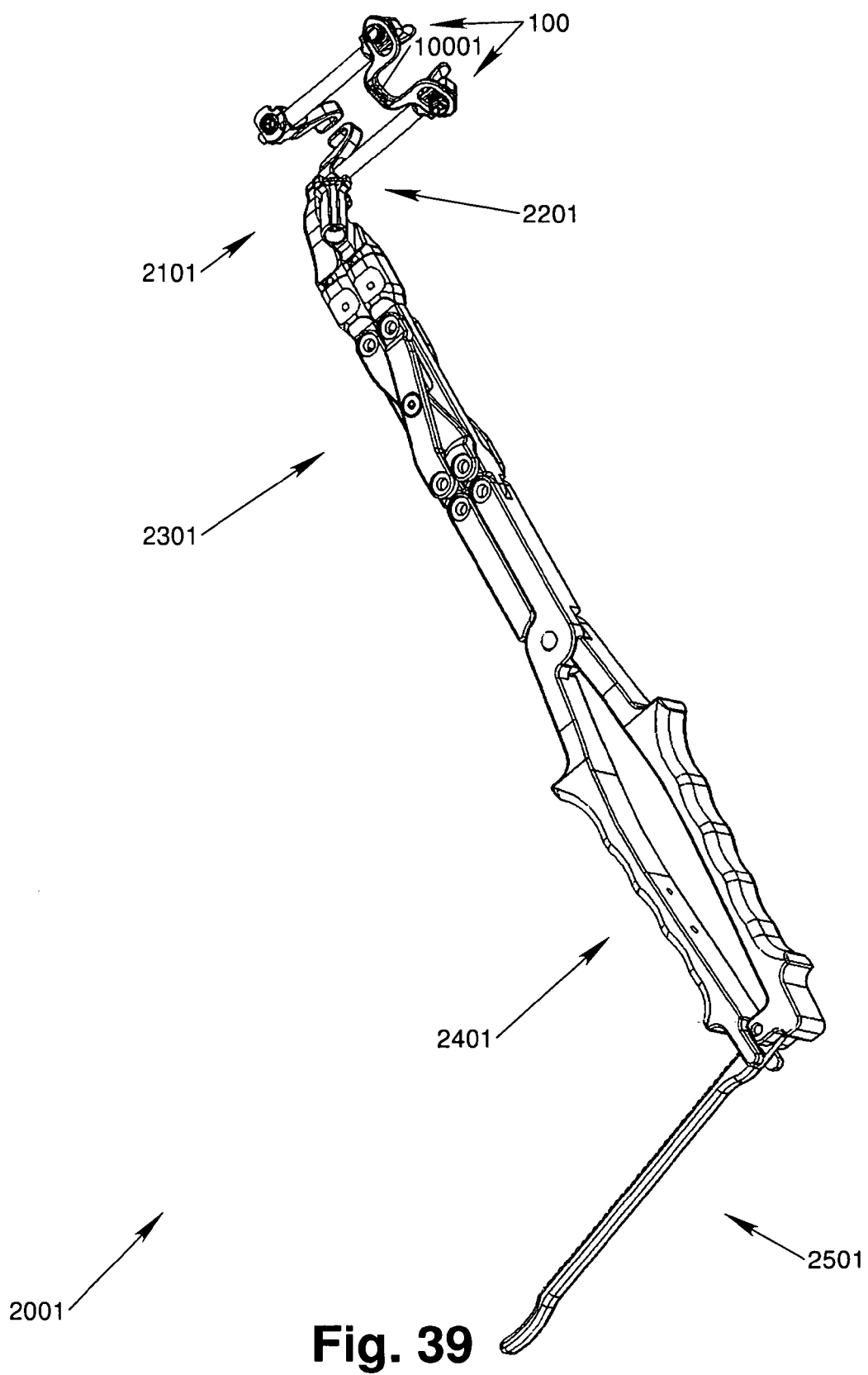

Extending from the proximal end 547 of the spacer portion 545 is the centered arm 558. The centered arm 558 is defined by a pair of steps 560 positioned on either lateral surface 552 of the second arm portion 545. The steps 560 extend across the lateral surface 552 from the upper edge 554 of the second vertebral engaging arm 540 toward the lower edge 556 and at an angle 562 extending toward the distal end 546, as shown in FIGS. 29, 31, 33. The depth of the steps 560 is predetermined so that the centered arm 558 is receivable between the spaced arms 530 of the first vertebral engaging arm 510. The centered arm 558 includes an annular end portion 564 and a second pivot throughbore 566 extending therethrough configured to accept the pivot mechanism 590 therein.

The U-shaped body 570 includes a base portion 571 and a pair of spaced side arms 580. The spaced side arms 580 extend in parallel from the bottom surface 572 of the base portion 571 and include annular-shaped distal ends 581. The spaced side arms 580 are separated by a distance 582 sufficient to receive the spaced arms 530 of the first vertebral engaging arm 510 therebetween. Further, the spaced side arms 580 include third pivot throughbores 583 extending therethrough and configured to accept the pivot mechanism 590 therein, the third pivot throughbores 583 further corresponding to the pivot throughbores 533 of the spaced arms 530 of the first vertebral engaging arm 510 and second pivot throughbore 566 of the centered arm 558 of the second vertebral engaging arm 540. As with the first and second vertebral engaging arms 510, 540, the sleeve arms 580 preferably include rounded edges to minimize damaging the adjacent tissue when inserted between lamina in the spine.

The base portion 571 includes a stop portion 572. In one embodiment, the stop portion 572 is defined by a bottom surface 572, the bottom surface 572 configured for contacting the spaced arms 530 and center arms 558. In addition, the base portion 571 further includes slotted side surfaces 573 for being engaged by the inserter tool, rounded end surfaces 574 and an upper surface 575. The base portion 571 further includes a securing mechanism 576. In one embodiment, as shown in FIG. 29, the base portion 571 includes a threaded throughbore 577 extending from the top surface 575 to the bottom surface 572. The threaded throughbore 577 is configured to receive a set screw 578 therein, the set screw 578 configured to engage the centered arm 558 and spaced arms 530 to restrict movement of the centered 558 and spaced arms 530 when in the operable configuration.

The pivot mechanism 590 is configured to extend through the pivot throughbores 533, second pivot throughbore 566 and third pivot throughbores 583 and provide a structure around which the first and second vertebral engaging arms 510, 540 could pivot. In one embodiment, as shown in FIG. 29, the pivot mechanism 590 includes a bushing 591 and a pin 597. The bushing 591 is configured to extend through the pivot throughbores 533, second pivot throughbore 566 and third pivot throughbores 583. The bushing 591 further includes an enlarged head portion 592 for engaging an outer surface 584 of a sleeve arm 590 and a hollow portion 593 extending along the longitudinal axis 594 of the bushing 591 and configured to receive the pin 597 therein. The pin 597 includes an oversized pin head 598 configured to engage a second outer surface 585 of the sleeve arm 580. The pin 597 and bushing 591 can be secured in any manner known in the art, including a threaded connection, pins or set screws, for example.

Upon assembly of the spinal implant 500, the first and second vertebral engaging arms 510, 540 are free to pivot around the pivot mechanism 590. The angle 562 of the steps 560 on the second vertebral engaging arm 540 provides the spaced arms 530 with additional space to occupy thereby permitting the first and second vertebral engaging arms 510, 540 to be moved adjacent one another. By moving the steps 560 toward the second seat portion 542 and by optimizing the angle 562 of the steps 560, the first and second vertebral engaging arms 510, 540 are able to be positioned closer one another in the compact orientation 600.

The spinal implant 500 is adjustable between a compact orientation 600 and an operable orientation 601. Upon inserting the spinal implant 500 between adjacent lamina, the first and second vertebral engaging arms 510 can be extended from the compact orientation 600 to the operable orientation 601. Once the first and second vertebral engaging arms 510, 540 are extended to the operable orientation 601, the set screw 578 is inserted and tightened in the sleeve threaded throughbore 577 of the sleeve body portion 571 until the set screw 578 engages the first and second vertebral engaging arms 510, 540 and restricts the movements of those vertebral engaging arms 510, 540.

While the spinal implants 100, 200, 300, 400, 500 described above were directed toward insertion between adjacent lamina, the spinal implants 100, 200, 300, 400, 500 could be inserted in other portions of the spine. Alternatively, the spinal implant could function to relieve pressure on the spinal nerves branching off of the spinal cord due to spinal stenosis when implanted between the transverse processes. The spinal implants would provide distraction, thus expanding the spinal canal volume to reduce pressure on the spinal cord or spinal nerves branching off of the spinal cord. The placement of the implants near the middle of the span of the transverse process will tend not to impinge on the spinal nerves branching off of the spinal cord under the superior edge of the transverse process, yet not create a structural failure in the dense cortical bone of the transverse process itself.

Further, the placement of the implant on the transverse processes would provide equivalent decompress to the spinal cord or spinal nerves branching off of the spinal cord without risking damage to the spinal cord itself and the attendant paralysis to all inferior nerves below the point of implantation. The spinal nerves branching off of the spinal cord under the superior edge of the transverse process are under much less risk of damage during implantation on the transverse process because the spinal nerves can shift along with surrounding tissue and will not be pinched between the implant and the bone of the vertebrae. The loading on the transverse processes would be minimal because only minimal distraction and deflection of the structures of the spine are required with stenosis patient where typically the intervertebral discs have only subsided and have not failed. Placement of implants laterally on both transverse processes would limit lateral bending but minimally reduce extension and flexion.

The implant devices 100, 200, 300, 400, 500 of the present invention may be fabricated from any suitable materials having desirable strength and biocompatibility. Suitable materials may include, for example, biocompatible metals and related alloys (such as titanium and stainless steel), shape memory metals (such as Nitinol), biocompatible polymers (including, for example, materials of the polyaryletherketone family such as PEEK (polyetheretherketone), PAEK (polyaryletherketone), PEK (polyetherketone), PEKK (polyetherketoneketone), PEKEKK (polyetherketoneetherketoneketone), PEEKK (polyetherketoneketone), and PAEEK (polyaryletheretherketone), filled materials (such as carbon or glass fiber-reinforced materials), bone substitute materials (such as hydroxyapatite and tricalcium phosphate), composite materials, and/or any combination of the above.

In one form, the implant devices are formed of a PEEK-type material. In another from, the implant device may be formed, in whole or in part, or coated with a calcium phosphate ceramic bone substitute such as hydroxyapatite, tricalcium phosphate, and/or mixtures thereof. Particularly preferred hydroxyapatite and tricalcium phosphate compositions include those disclosed in, for example, U.S. Pat. No. 6,013,591, U.S. Pat. No. RE 39,196, and U.S. Patent Application Publication No. 2005/0031704, which are hereby incorporated in their entirety herein. Coating with the calcium phosphate ceramics can be achieved by any known method, including dip coating-sintering, immersion coating, electrophoretic deposition, hot isostatic pressing, solution deposition, ion-beam sputter coating and dynamic mixing, thermal spraying techniques such as plasma spraying, flame spraying and high-velocity oxy-fuel combustion spraying. In one preferred embodiment, hydroxyapetite coating is achieved by plasma spraying.

In yet another form, the implant device may be formed of a PEEK-type material and coated with such a bone substitute material. In yet another form, the implant device may be formed, in whole or in part, coated with, injected with, incorporate, and/or retain a bone growth stimulating composition such as the bioactive hydrogel matrix described, for example, in U.S. Pat. No. 6,231,881, U.S. Pat. No. 6,730,315, U.S. Pat. No. 6,315,994, U.S. Pat. No. 6,713,079, U.S. Pat. No. 6,261,587, U.S. Pat. No. 5,824,331, U.S. Pat. No. 6,068,974, U.S. Pat. No. 6,352,707, U.S. Pat. No. 6,270,977, U.S. Pat. No. 5,614,205, U.S. Pat. No. 6,790,455, U.S. Pat. No. 5,922,339, and U.S. Patent Application Publication No. 2005/0118230, which are hereby incorporated in their entirety herein. Another example of a composite for the spinal implant is a composition formed from PEEK coated with hydroxyapatite (HA) with no significant alteration to the biocompatibility profile to the PEEK. The HA coating provides sufficient mechanical bond strength to allow the HA to sufficiently adhere to the PEEK support structure which forms the implant body without having to melt PEEK to obtain sufficient bond strength. The HA coated PEEK now preserves the biocompatibility profile of the PEEK and yet still provides a bioactive interface for improved biologic integration between the implant and patient. The HA coating provides sufficient bioactivity to allow an interface between the adjacent bone and HA to allow bone ingrowth, ongrowth, or otherwise act as an osteoconductive agent, i.e. fusion, by the patient's body.

A spinal implant inserter apparatus is shown in FIGS. 34-52. The inserter apparatus 2001 generally securely engages a spinal implant 100, 200, 300, 400, 500, and is configured to distract the spine and implant the spinal implant device 100, 200, 300, 400, 500 simultaneously.

Figure 44:
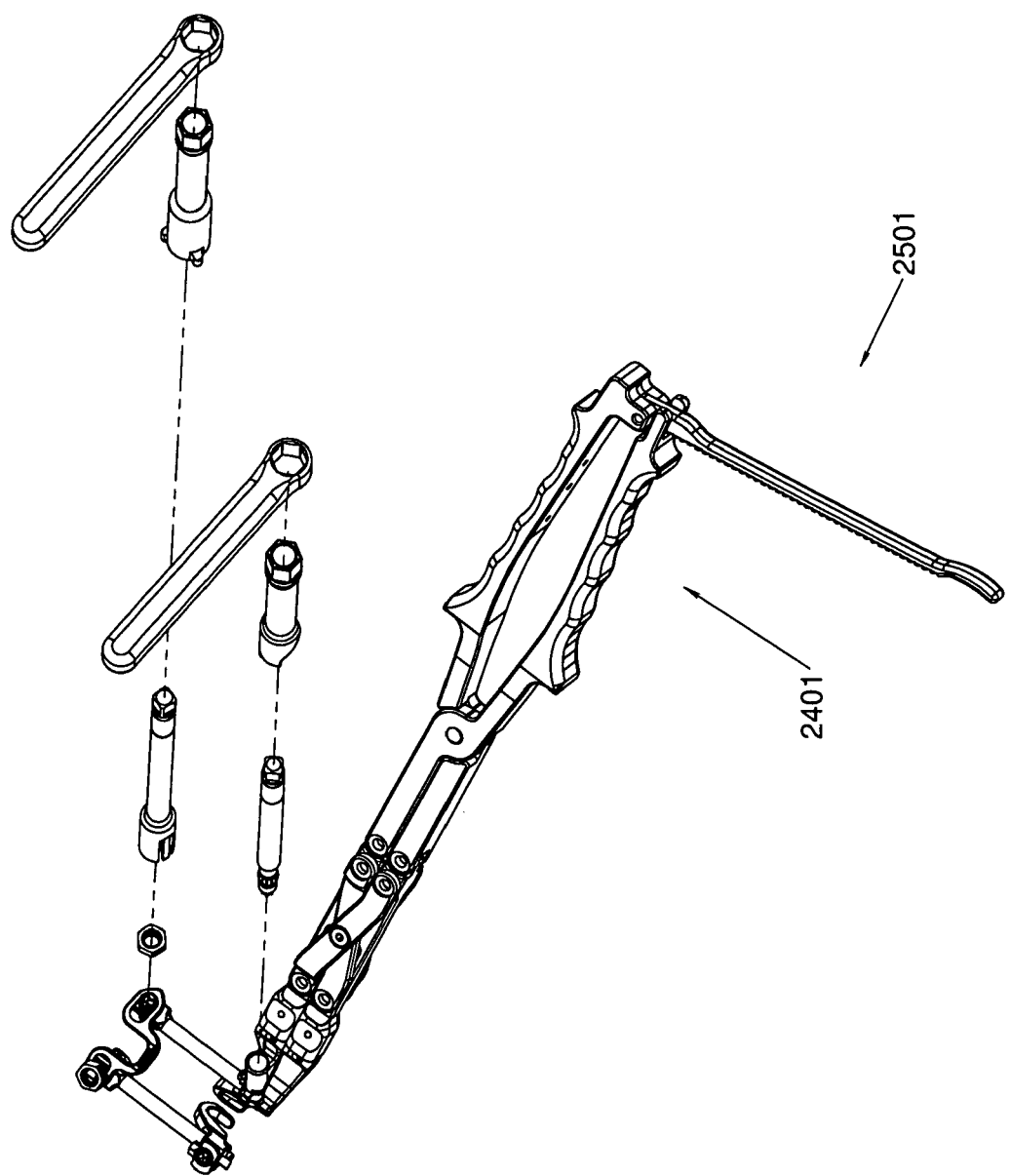
Figure 45:
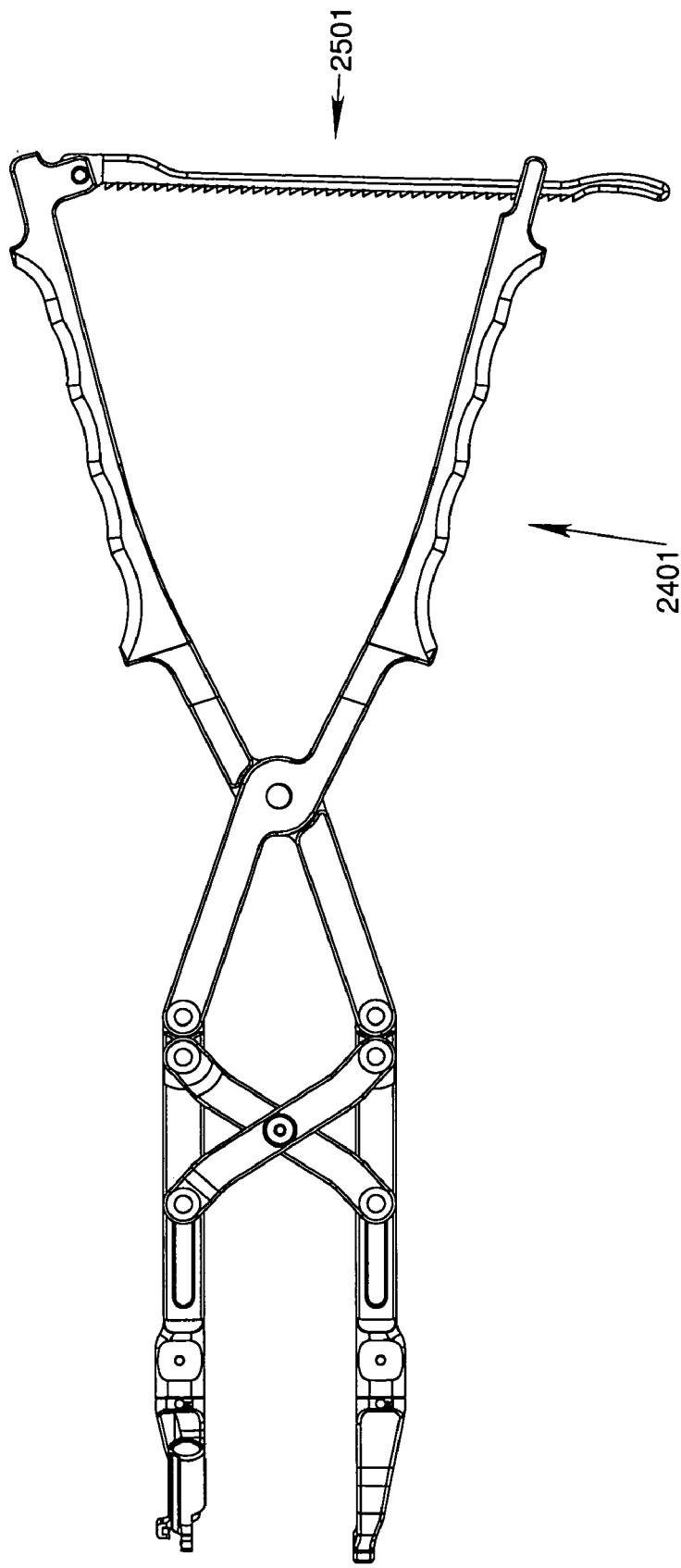

The inserter apparatus 2001 includes the first gripping portion 2101, the second gripping portion 2201, the parallel-action assembly 2301, the handles 2401, the ratchet bar 2501, the screw driver 2601, the counter-torque device 2651, the nut driver 2701, and the counter-torque handler 2751 shown together in FIG. 44.

Figure 46:
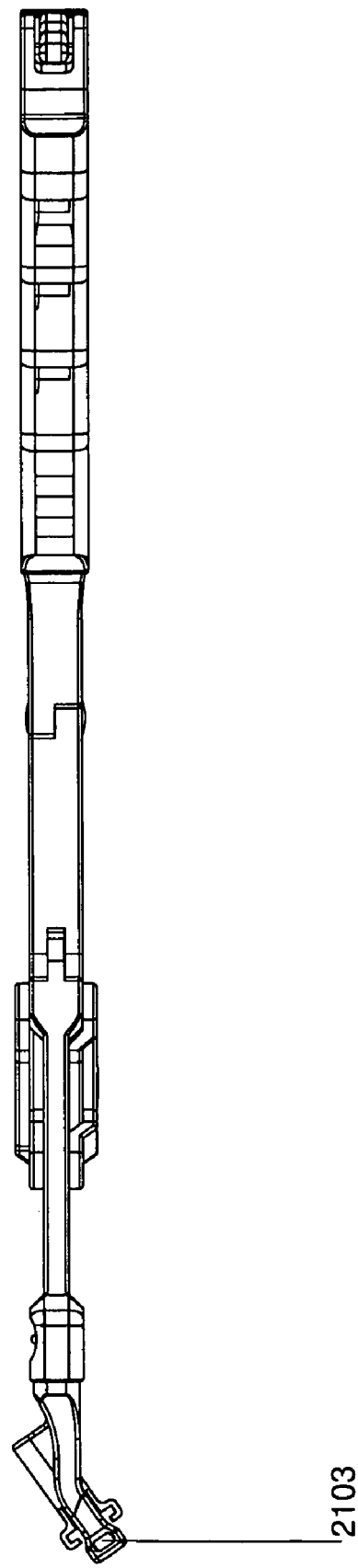
Figure 48:
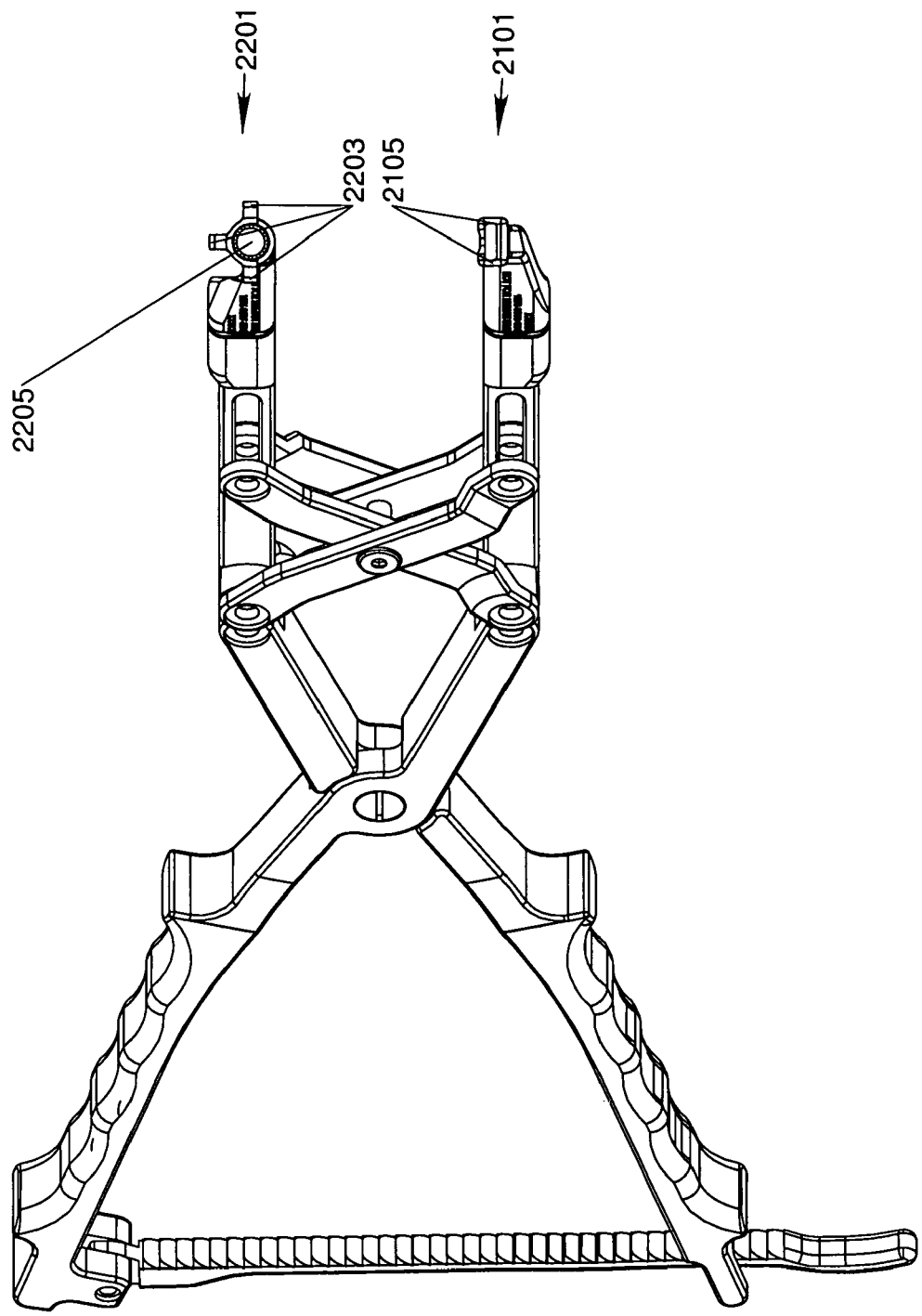

The first gripping portion 2101 includes two flanges 2105 as shown in FIG. 48, and a groove 2103 shown in FIG. 46, the groove located at the distal end of the inserter apparatus 2001 for providing a fixed anchor point for the spinal implant 100, 200, 300, 400, 500. The first gripping portion 2101 allows for the mechanical engagement of the spinal implant 100, 200, 300, 400, 500 and the release of the spinal implant 100, 200, 300, 400, 500 upon completion of the implantation process as described below.

Figure 47:
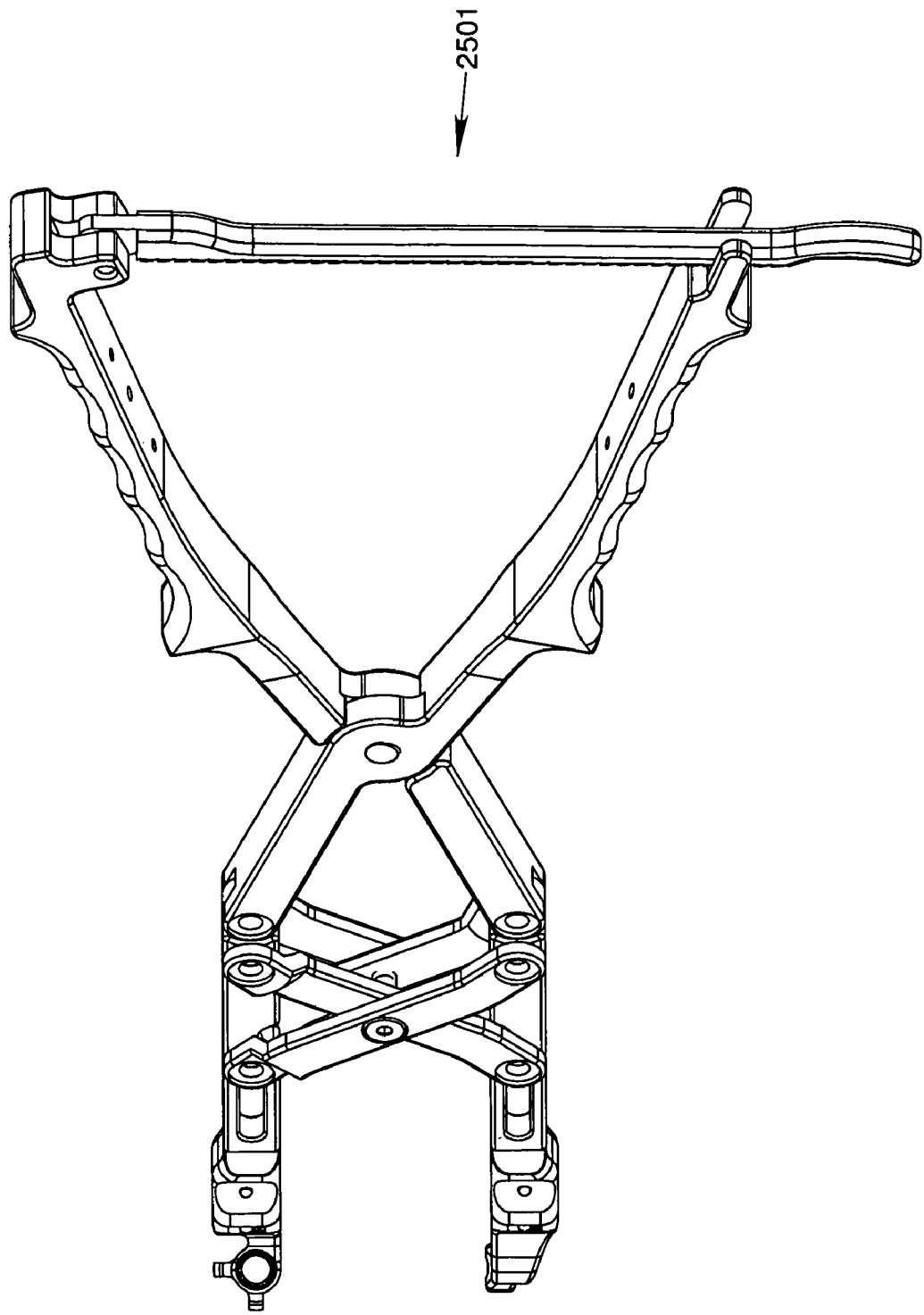

The first and second gripping portion 2101 & 2201 are canted at an angle K of approximately 36 degrees as shown in FIG. 46. As shown in FIG. 47, the canting allows a surgeon to look directly into the incision to see the progress of the implantation without the insertion tool itself obstructing the surgeon's vision. In addition, the first and second gripping portion 2101 & 2201 are preferably made of 17-4 stainless steel. The 17-4 stainless steel is preferably low friction chrome coated, hardened, and electropolished to allow the spinal implants 100, 200, 300, 400, 500 to easily connect and disconnect to the flanges 2105.

The second gripping portion 2201 is composed of three fingers 2203 and a centrally located through bore 2205. The fingers 2203 provide for a way to release ably connect the spinal implants 100, 200, 300, 400, 500 to the insertion tool 2001 as previously described. The through bore 2205 provides a guide for the screw driver 2601 in order to prevent inadvertent injury to the spinal cord or nerves when driving the driver 2601 as shown in FIG. 44.

The parallel-action assembly 2301 is composed of multiple links 2303 joined together for providing parallel movement, i.e. linear rather than arcuate translation. The parallel-action assembly 2301 functions to convert arcuate translation of the handles 2401 to parallel translation. For example, the first and second gripping portions 2011 & 2201 move together and away from one another while remaining parallel. The links 2303 overlap one another and shift within slots 2305 as shown in FIGS. 47 & 48 to create parallel movement of the first and second gripping sections 2101 & 2201. Pins used to connect the links 2303 provide pivot points for the parallel-action assembly 2301 are preferably clear plastic to prevent galling and smooth movement of the linkages.

The handles 2401 are connect by a pivot 2403 for providing force and leverage to the operator of the inserter 2001 as shown in FIGS. 45-48. The handles 2401 are threadably connected, i.e. screwed, by the pivot 2403 which provides the pivot axis for the arcuate movement of the handles.

The ratchet bar 2501 is composed of a rack 2505 connected with a ratchet pin 2507 for providing a safety mechanism to prevent unintended mechanical release of the implant 100, 200, 300, 400, 500 from the inserter 2001. The rack is composed of a length of teeth shown in FIG. 48 that interface with a catch 2405 in the handles 2401 shown in FIG. 46. As the handles 2401 are moved together, the catch 2405 will interface with the teeth of the rack 2505 to allow motion together, such as by providing shifting mechanical engagement, in only one direction, such as allowing the handles to only move together. This allows the implant 100, 200, 300, 400, 500 to deploy and distract the vertebrae of the spine without the handles moving away from one another due to the force exerted by the vertebrae on the inserter 2001. As described previously, the ratchet bar can be disengaged to allow the handles 2401 to move away from one another. Alternatively, the ratchet pin 2507 can be coupled to a torsional spring to bias the rack 2505 to the closed position to prevent any possibility of unintended mechanical release of the implant 100, 200, 300, 400, 500.

The screw driver 2601 is composed of a guide spring 2603, a drive head 2605, and connector 2607 for providing torque to rotate and secure the fastener of the spinal implant 100, 200, 300, 400, 500. The guide spring 2603 is composed of a series of counter poised cantilevered springs to create an egg shaped elliptical form that provides a circular line contact to the through bore 2205 to provide precise rotation of the screw driver 2601. The drive head 2605 shown is a torx type screw head shown in FIG. 51 but any type of screw head could be used alternatively, i.e. crosshead, slotted, etc. The connector 2607 allows for quick connection to any of a wide variety of handles for surgical instruments, such as T-bar handles or off-set ratcheted handles.

Figure 52:
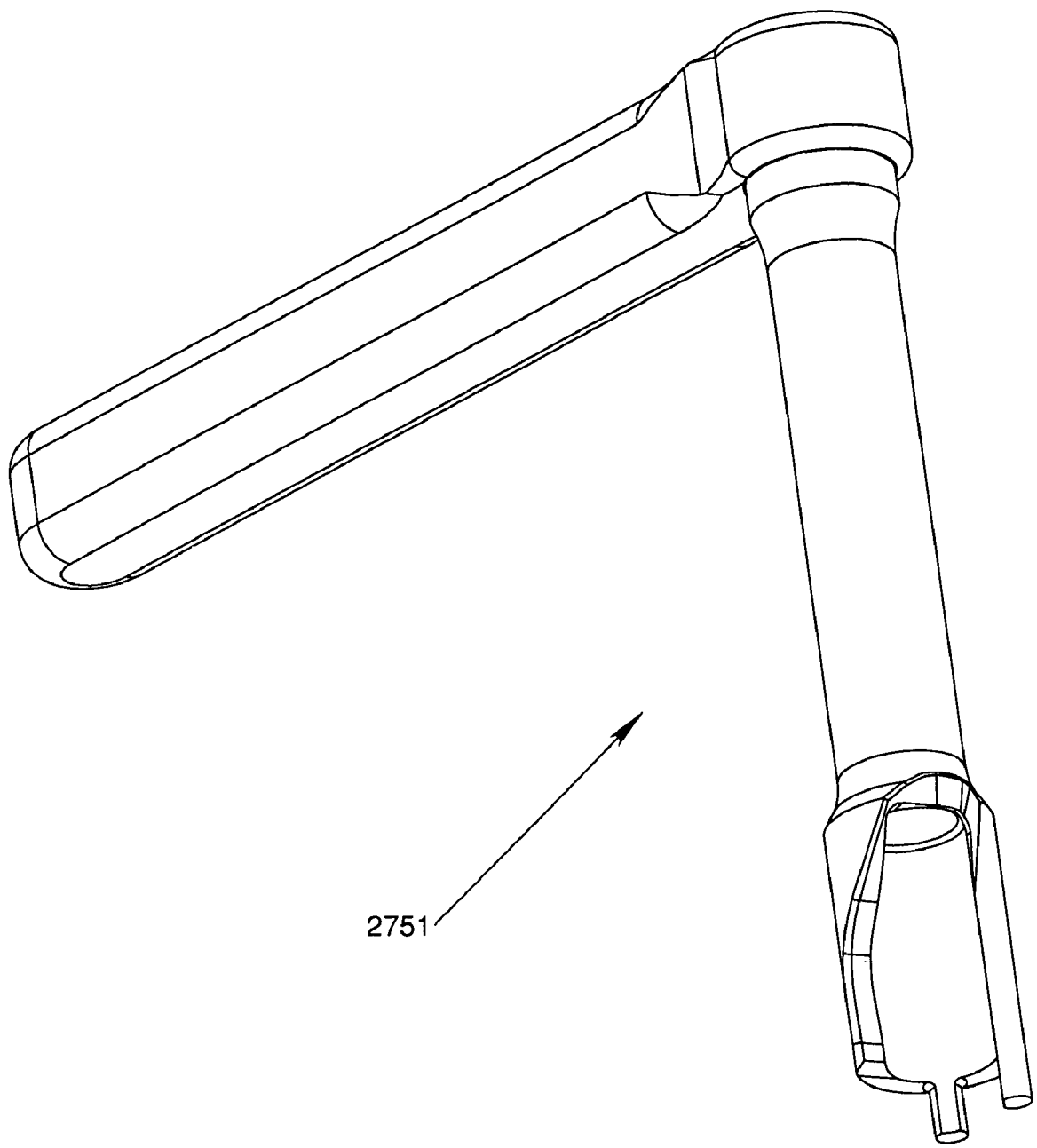

The counter-torque device 2651 is composed of a counter-torque device shaft 2653, a counter-torque device handle 2655, and counter-torque device pins 2657 for providing counter-torque to offset the torque created by the screw driver 2601 and prevent rotation or dislocation of the spinal implant 100, 200, 300, 400, 500. As shown in FIG. 52, the counter-torque device shaft 2653 fits within the counter-torque device handle 2655 with a male and female hexagonal slip fit connection as shown in FIG. 44. The counter-torque device pins 2657 engage grooves within the receiving portion of the spinal implant 100, 200, 300, 400, 500 to resist torque and rotation.

Figure 49:
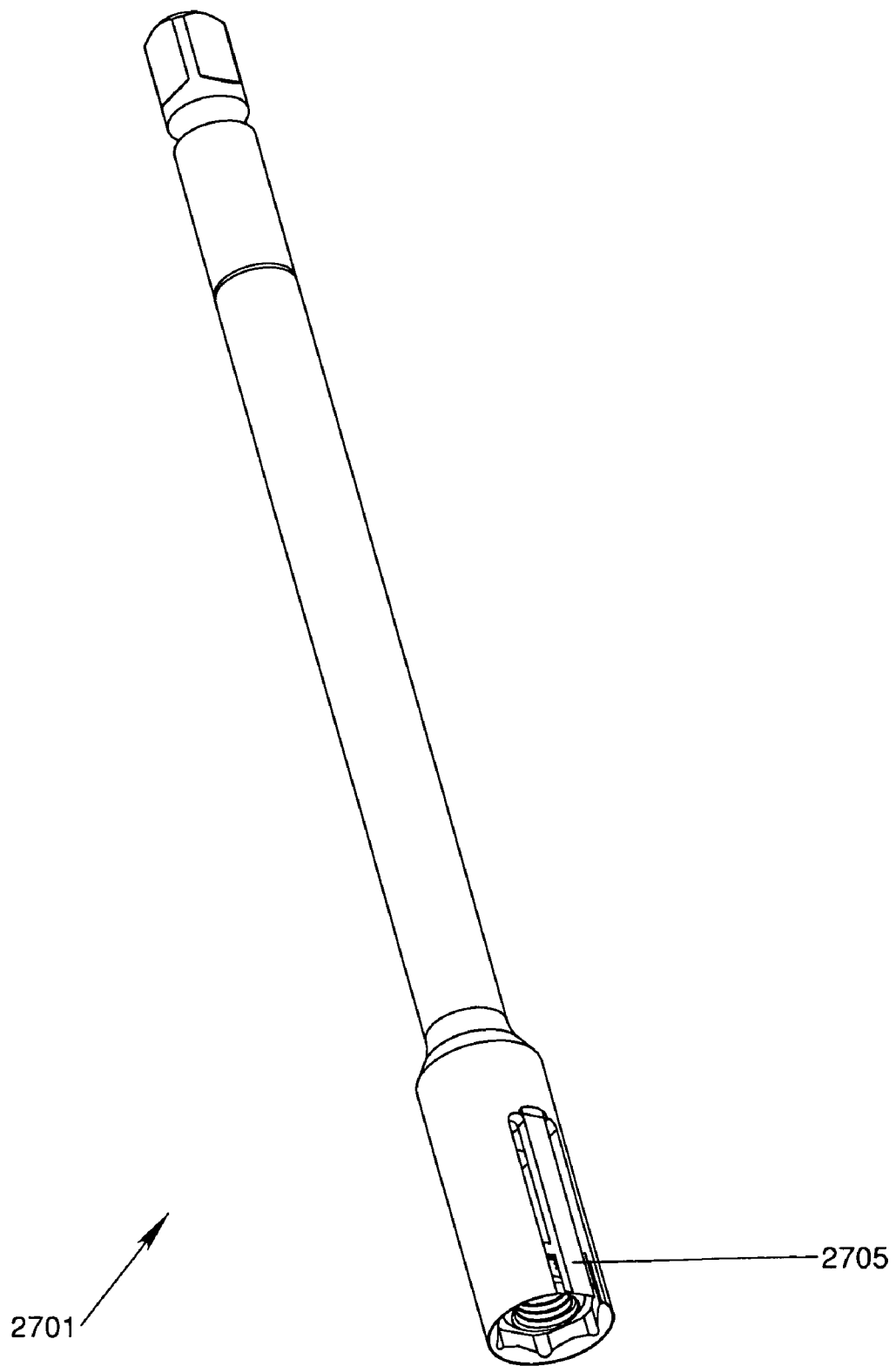

The nut driver 2701 is composed of an access port 2703, a cantilever spring 2705 as described previously. The nut driver 2701 is also composed of a nut driver shaft 2701 for providing a structural connection between the fastener and the operator as shown in FIG. 49. The nut driver connector 2709 again provides a quick connect for various commercially available handles as previously described.

Figure 50:
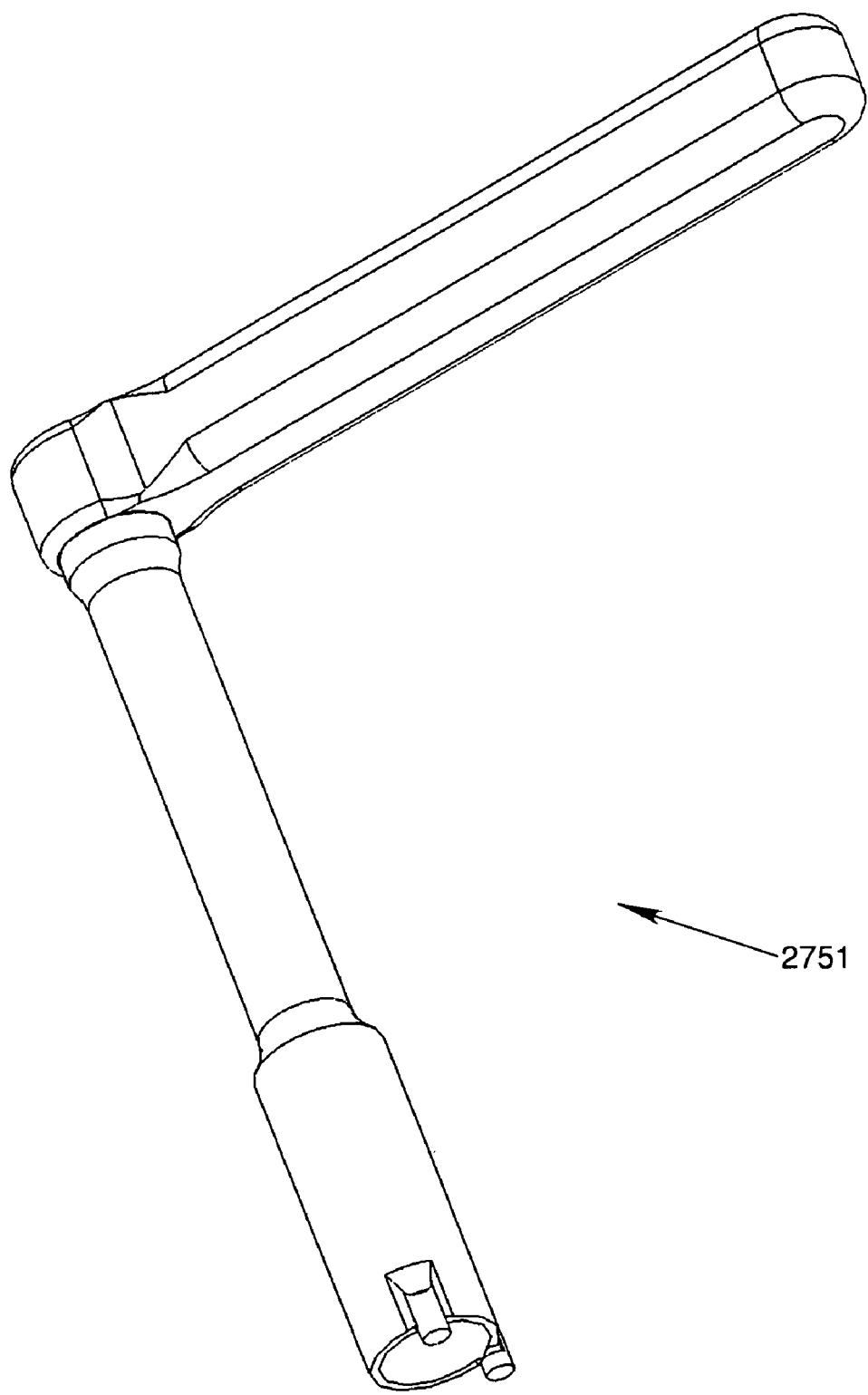
Figure 51:
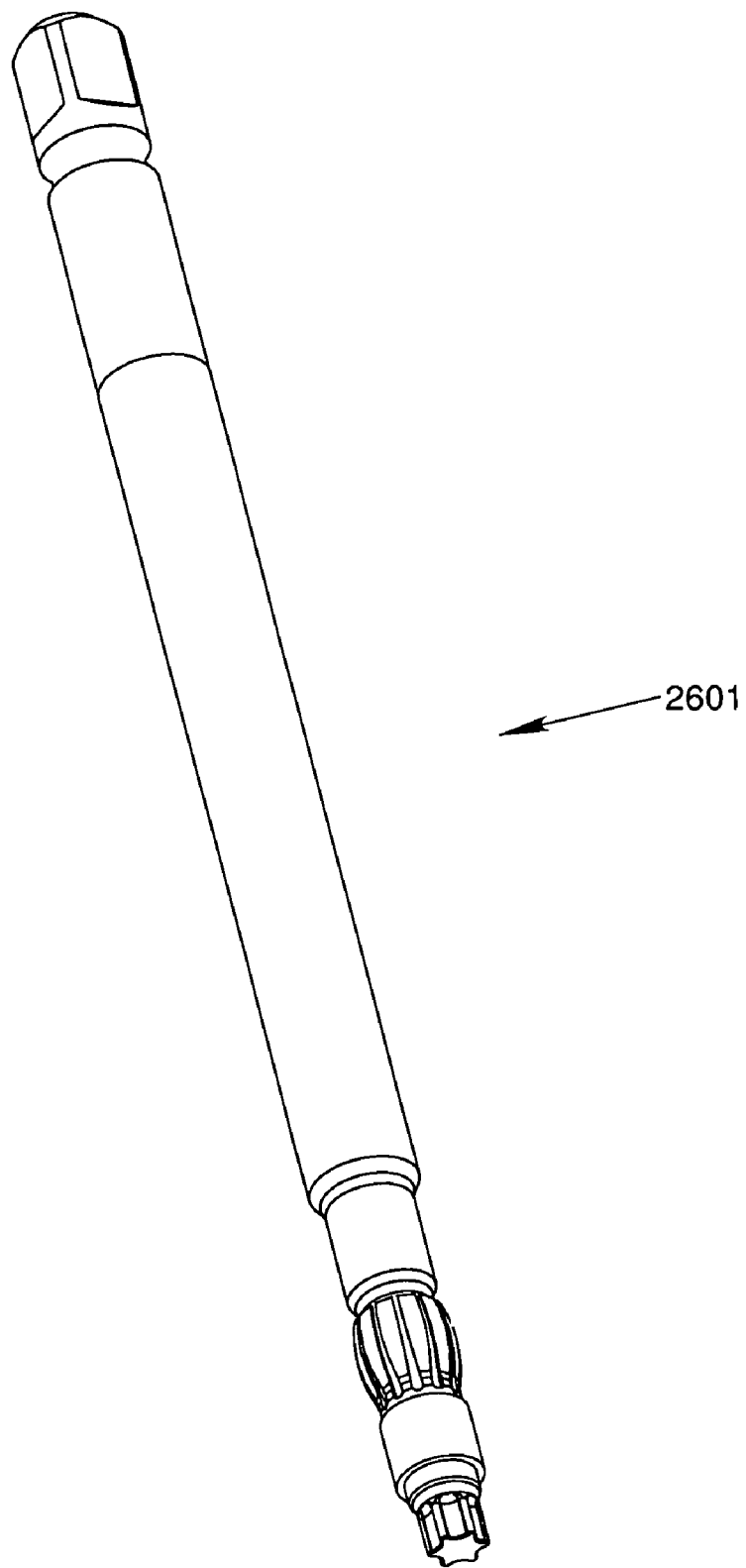

The counter-torque handler 2751 is composed of a counter-torque handler shaft 2753, a counter-torque device handle 2755, and counter-torque handler pins 2757 for providing counter-torque to offset the torque created by the nut driver 2701 and prevent rotation or dislocation of the spinal implant 100, 200, 300, 400, 500. As shown in FIG. 50, the counter-torque handler shaft 2753 fits within the counter-torque handler handle 2755 with a male and female hexagonal slip fit connection as shown in FIG. 50. The counter-torque handler pins 2657 engage on both sides of the connector 10001 to resist torque and rotation of both the connector 10001 and the spinal implant 100, 200, 300, 400, 500.

Insertion of the spinal implant assembly includes multiple steps. First, after sterilizing the surgical field and anesthetizing the patient, a surgical incision is made in the patient from the posterior, or the back of the patient. A posterior approach is used because it provides greater access for the surgeon to the boney structures of the spine. The access to the spine permits surgical implantation of the spinal implant.

Once the incision is made the surrounding tissue is distracted or moved out of the way using standard instruments and methodology. Distraction of tissue at the implantation site provides a direct line of sight for the surgeon to visually see the implantation of the spinal implant on the lamina of the spine without causing undue tissue damage.

The spinal implant is then attached to the implant insertion apparatus 2001. In the preferred embodiment, the spinal implant 100, 200, 300, 400, 500 with the elongate rod member is attached to the insertion apparatus 2001. The spinal implant 100, 200, 300, 400, 500 is attached by mechanically engaging the elongate rod member to the first gripping portion 2101. The implant 100, 200, 300, 400, 500 engages the first gripping portion 2101 by inserting the distal end or tip of the elongate rod member into the groove 2103 shown in FIG. 46 at a 45 degree angle. The implant is then rotated about the first gripping portion 2101 until the flanges 2105 shown in FIG. 48 engage or fit into the grooves of the elongate rod member of the implant 100, 200, 300, 400, 500.

The implant 100, 200, 300, 400, 500 rod member is rotated until it is parallel to the first gripping portions 2001 and second gripping portion 2201. The flange of the spinal implant 100, 200, 300, 400, 500 receiving portion then can be shifted into the fingers 2203 of the second gripping portion 2201 shown in FIG. 45 to surround around the flange of the implant 100, 200, 300, 400, 500.

The attached implant 100, 200, 300, 400, 500 has a screw driver 2601 inserted into the through bore 2205 of the second gripping portion 2201. The screw driver 2601 is placed in contact and mechanically engaged to the implant fastener. The driver 2601 is then rotated counter clockwise to loosen the fastener of the spinal implant 100, 200, 300, 400, 500.

The fastener is loosened enough to allow ease of shifting of the receiving portion on the elongate rod yet maintain connection of the faster to the implant 100, 200, 300, 400, 500. The fastener is loosened to allow shifting because of the need to avoid friction by the rod on the receiving portion when the implant is forcefully driven into position on the lamina and to allow the implant to be adjustable.

Figure 7A:
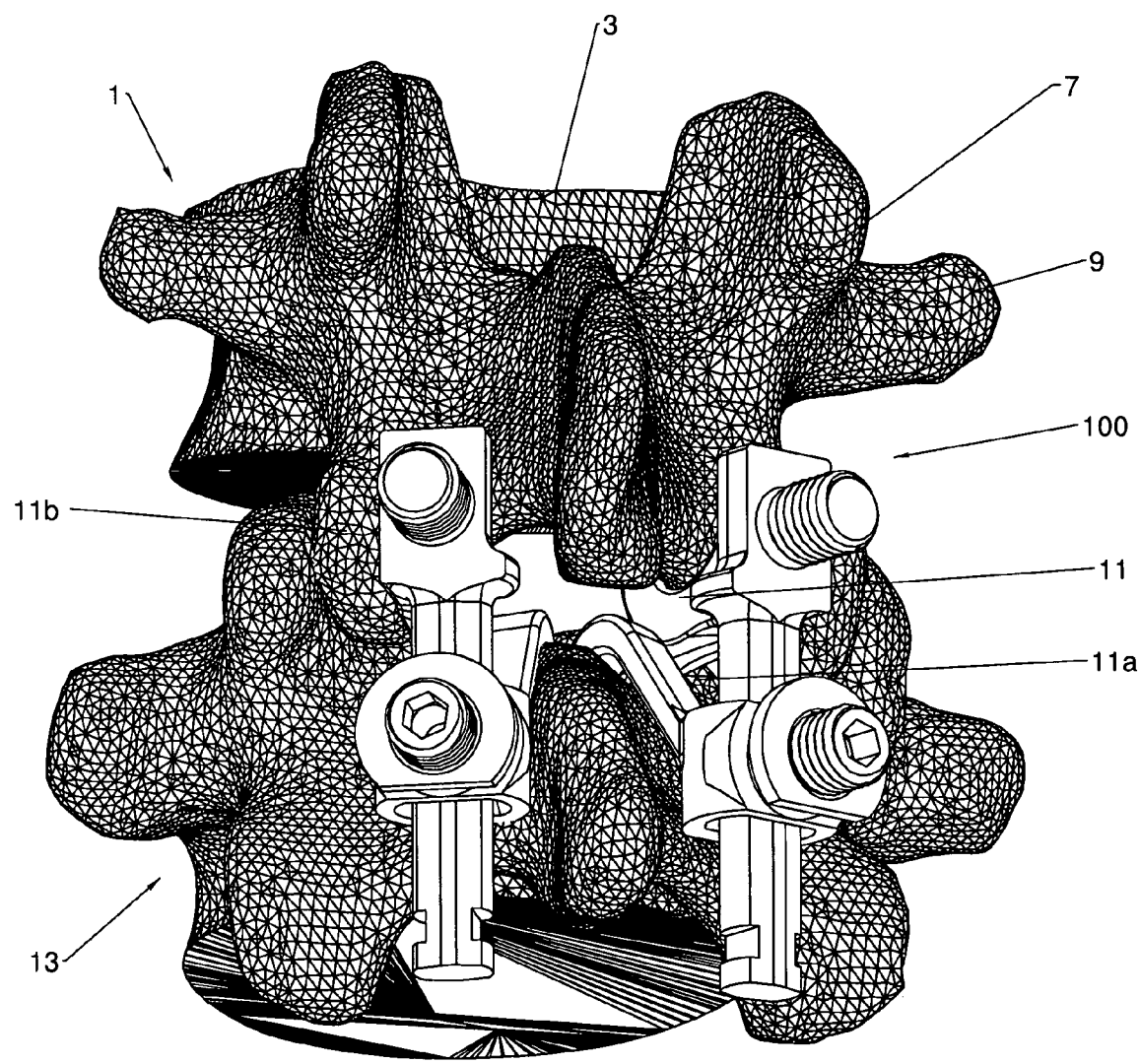
FIG. 7A is a perspective view of the spinal implant assembly of FIG. 1 showing two assemblies inserted between adjacent lamina.
Figure 7B:
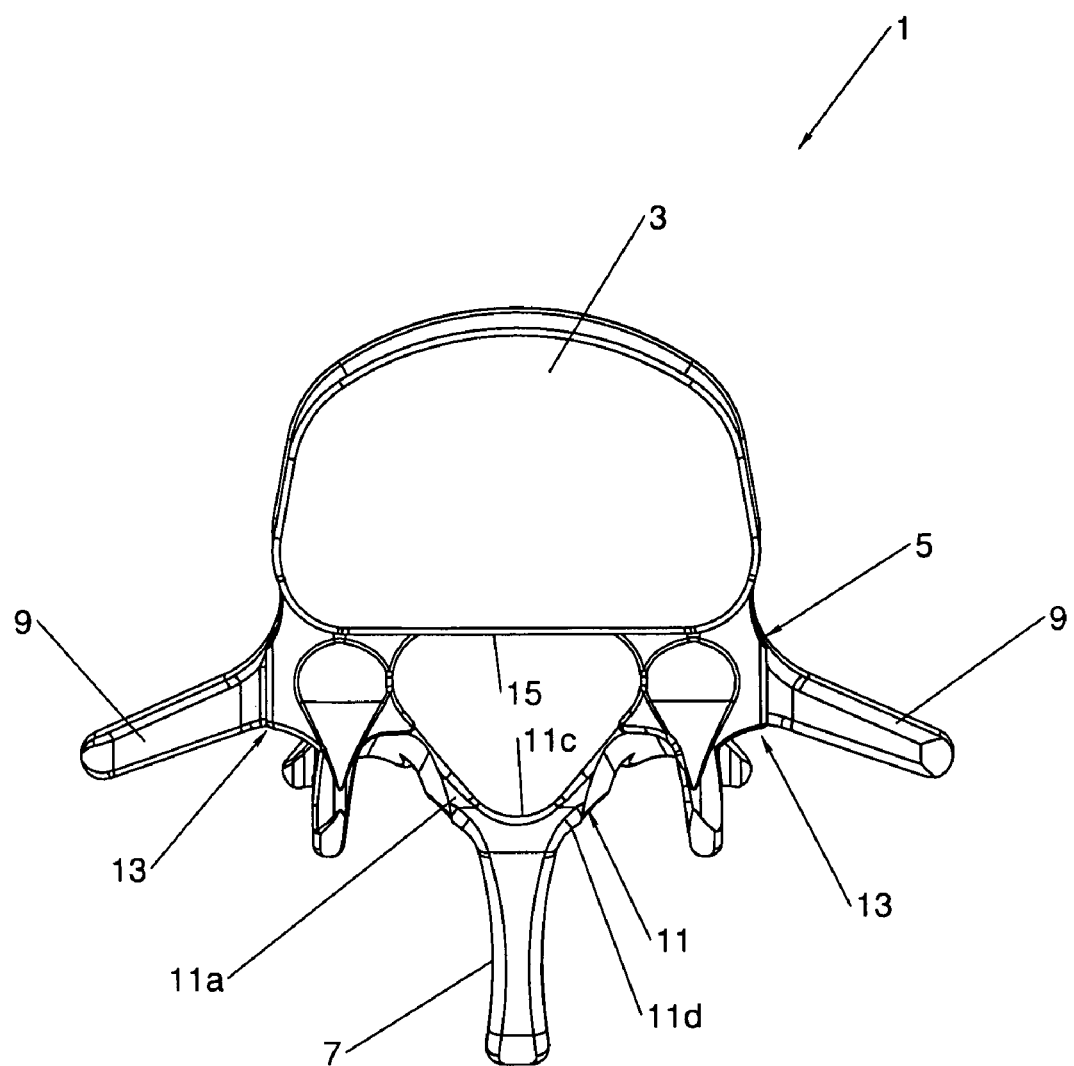
FIG. 7B is a top plan view of a vertebral body.
Figure 8:
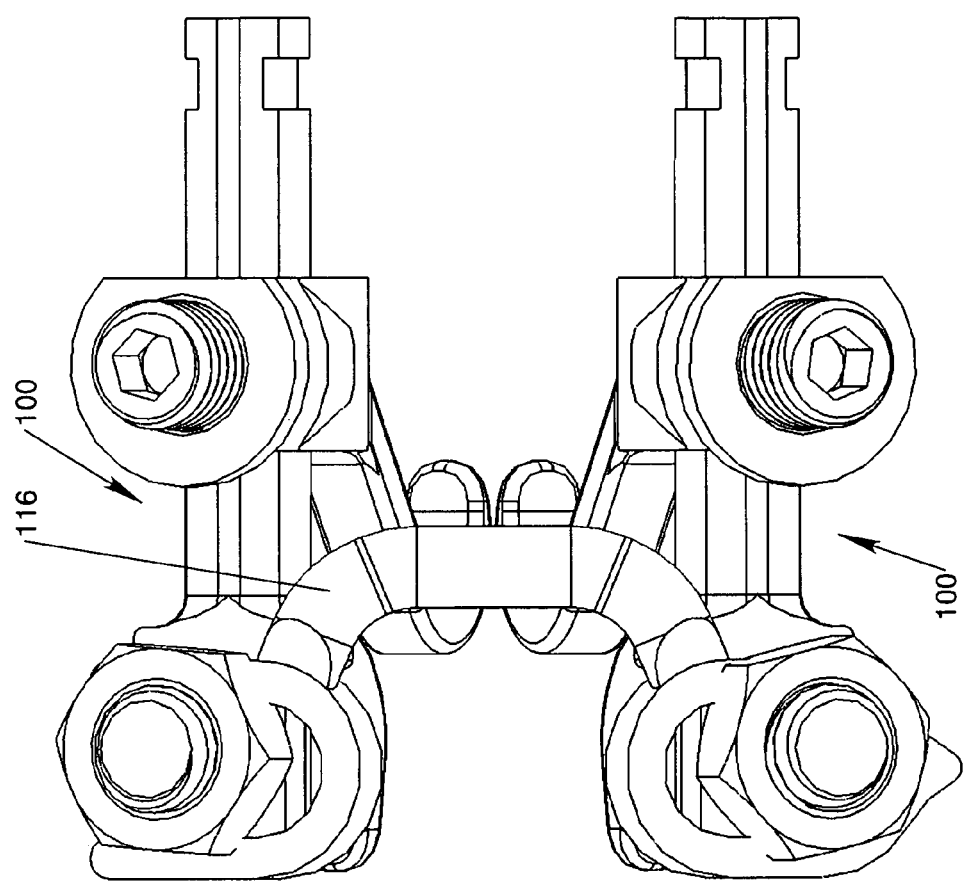
FIG. 8 is a is a perspective view of the spinal implant assembly of FIG. 1 showing two assemblies connected by a transverse member.

The upper engagement portion of the spinal implant 100, 200, 300, 400, 500 is inserted to engage the inferior portion of a laminar region of a vertebral body as shown in FIG. 7A. The installation site of the implant may be prepared by removing some of the bone of the vertebrae to conform to the surface of the spinal implant thus reducing the risk that the implant will shift out of position.

The handles 2401 of the inserter 2001 are moved toward and away to adjust the position of the spinal implant so that the lower engagement portion of the spinal implant will engage the superior portion of a laminar region of a second vertebral body. The movement of the handles 2401 together maintains the parallel position of the first and second gripping portion through the mechanical action of the parallel-action assembly 2301 otherwise known as a scissor lift. The parallel-action assembly 2301 can be kinematically described as a set of four bar linkages that convert arcuate translation to linear translation. The handles 2401 provide mechanical advantage to the surgeon's hands so that the vertebral bodies can be distracted sufficiently by the deployment of the spinal implant 100, 200, 300, 400, 500 to relieve the pressure by the facets on the spinal cord or spinal nerves.

The spinal implant 100, 200, 300, 400, 500 is fully deployed when the elongate rod member has reached the end of its travel. Once the spinal implant 100, 200, 300, 400, 500 has been adjusted to the proper positioned on the spine the lower engagement portion of the implant 100, 200, 300, 400, 500 engages the superior portion of a laminar region of the second vertebral body.

Once the spinal implant 100, 200, 300, 400, 500 is in proper position then the implant fastener must be locked into its final position. To lock the fastener, the screw driver 2601 has a counter-torque device 2651 slipped over the screw driver 2601. The counter-torque device 2651 is held in position to prevent the spinal implant 100, 200, 300, 400, 500 from moving out of position, i.e. dislocation, due to the torque of the screw driver 2601. The torque would otherwise be transmitted to the implant and spine causing undesired translation as a final lock down torque is applied by the screw driver 2601 on the fastener of the implant 100, 200, 300, 400, 500. The final lock down of the fastener secures the spinal implant 100, 200, 300, 400, 500 to a fixed condition.

A set of spinal implants 100, 200, 300, 400, 500 will typically be used to structurally support the spine of the patient. The insertion of a second spinal implant to provide structural support on both sides of the spinous processes of the spine is shown in FIG. 7A. The implants 100, 200, 300, 400, 500 are designated left and right to fit the contour of the lamina on the left and right sides of the spinous process. The pairing of spinal implant 100, 200, 300, 400, 500 allows for greater stability, because the compression loading of the spine is shared by both implants providing better balance while supporting the spine and preventing excessive loading on one side of the spine.

A connector 100001, or transverse member 116, can then be added to the set of spinal implants 100, 200, 300, 400, 500 to provide additional stability. The use of a connector 10001 increases the resistance of the spinal implants to displacement. Specifically, the connector 10001 prevents movement of the implants 100, 200, 300, 400, 500 out of position should the patient bend or twist because the connector 10001 will maintain alignment of the implants with that of the spine. Alternatively however, a standard pedicle screw and distraction rod connector may also be used to provide a mechanical connection between the spinal implants.

Figure 40:
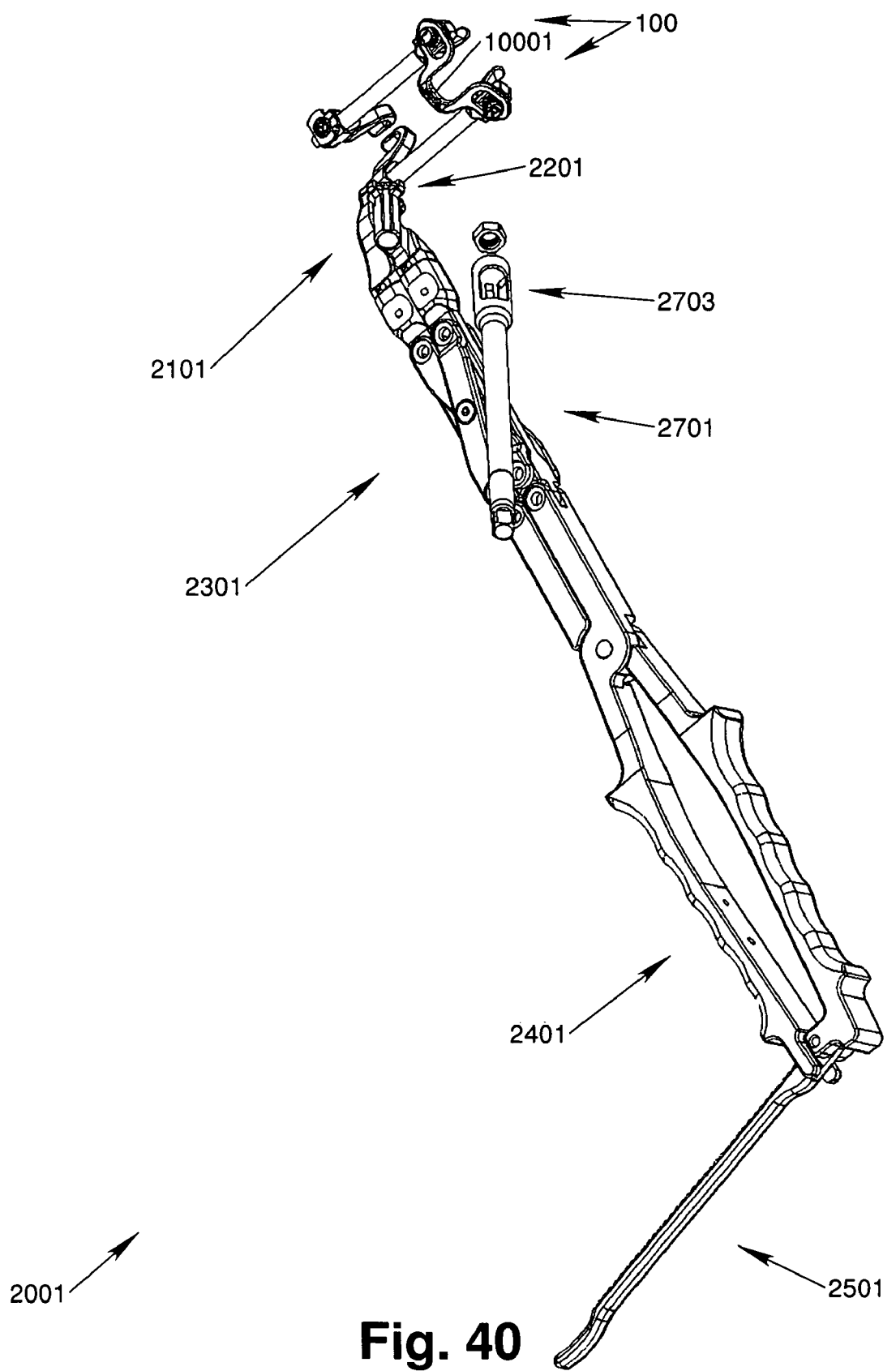

The attachment of the connector begins with attaching a fastener, i.e. a hexagonal nut, to a nut driver 2701 as shown in FIG. 40. The fastener is held in place by the nut driver 2701 by a female receptacle in the nut driver 2701 and by deflection of a cantilever spring 2705 shown in FIG. 49. The cantilever spring 2705 deflects to allow the fastener to be locked into the nut driver 2701 with a snap fit connection. Should the fastener, such as a hexagonal nut, need to be removed an access port 2703 is provided to allow access to the fastener, to remove the fastener as shown in FIG. 40. Alternatively, other types of mechanical fasteners can be used such as screws, snap fit connectors, and pins.

Figure 41:
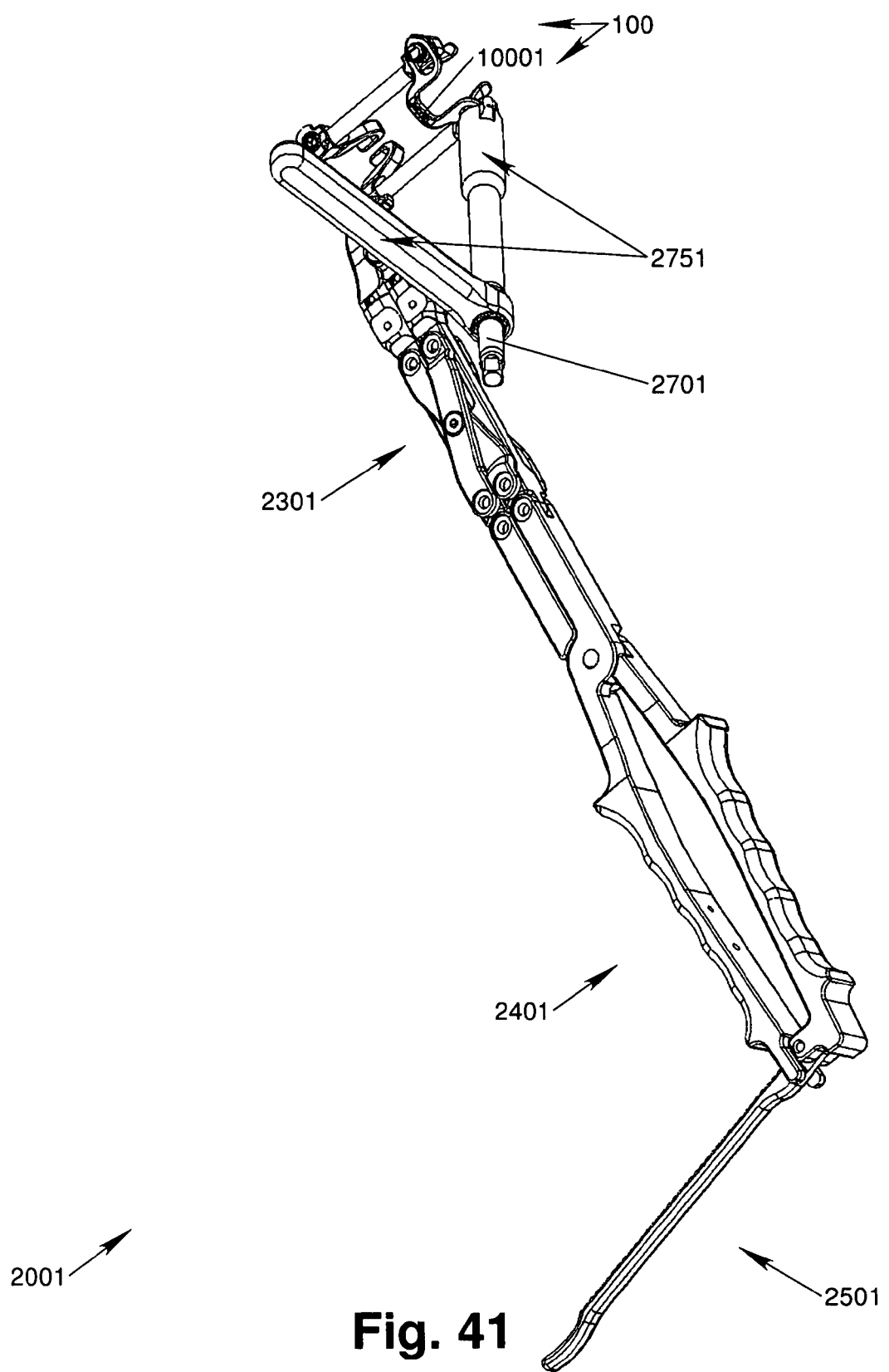
Figure 42:
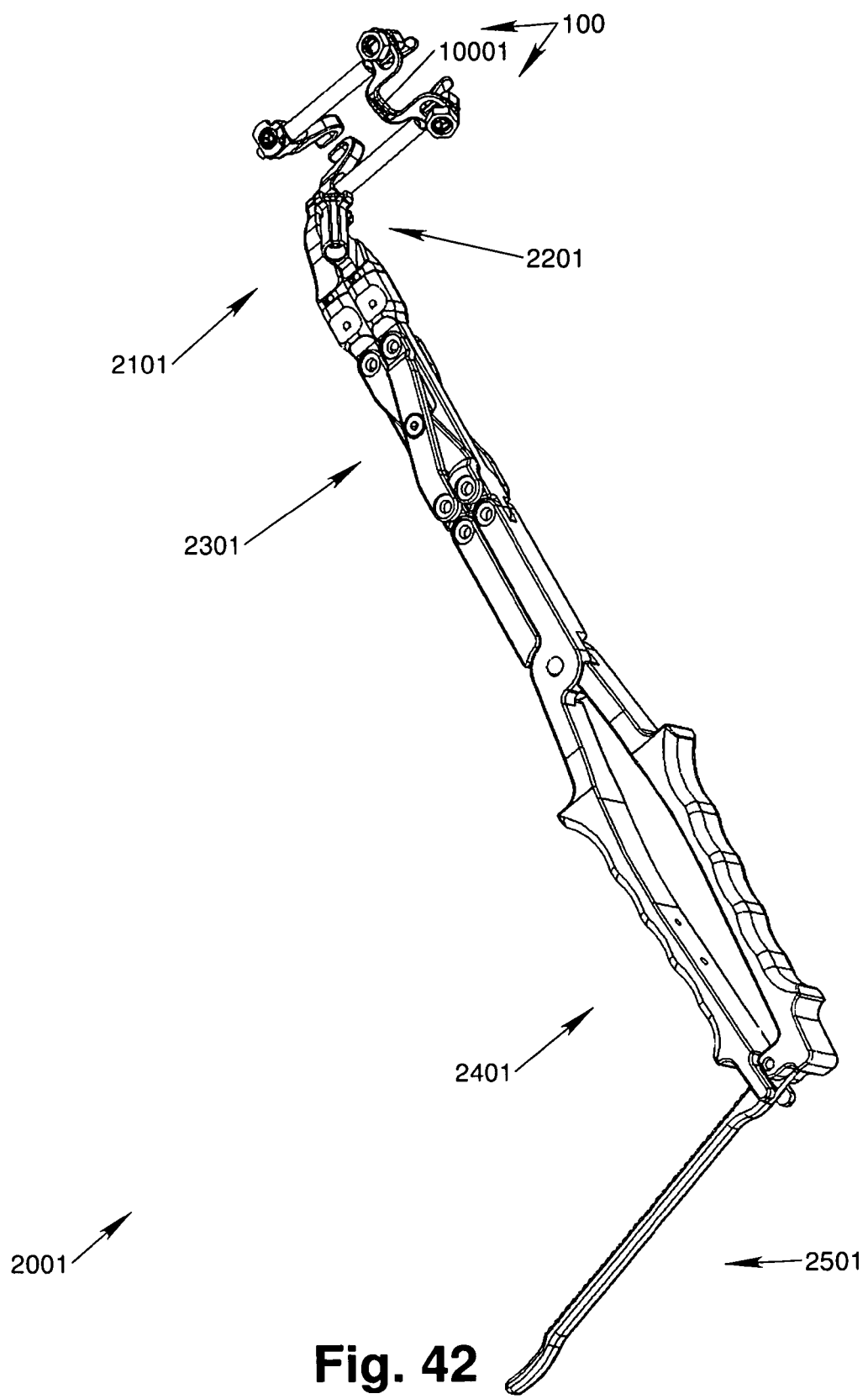

The nut driver 2701 and attached fastener, is then placed in contact with a fastener projection, such as a bolt, on the spinal implant 100, 200, 300, 400, 500. A counter-torque handler 2751 is then placed over the nut driver 2701 to prevent dislocation of the spinal implant during attachment of the fastener, as shown in FIG. 41.

The nut driver 2701 is rotated and the counter-torque handler 2751 is held in place to prevent inadvertent dislocation of the spinal implant 100, 200, 300, 400, 500 similar to the process done for the screw driver 2601. The nut driver 2701 is rotated to secure the connector to the spinal implant 100, 200, 300, 400, 500 to fix the connector 10001 in place. The process of attaching the fastener is repeated for both spinal implants 100, 200, 300, 400, 500.

Figure 43:
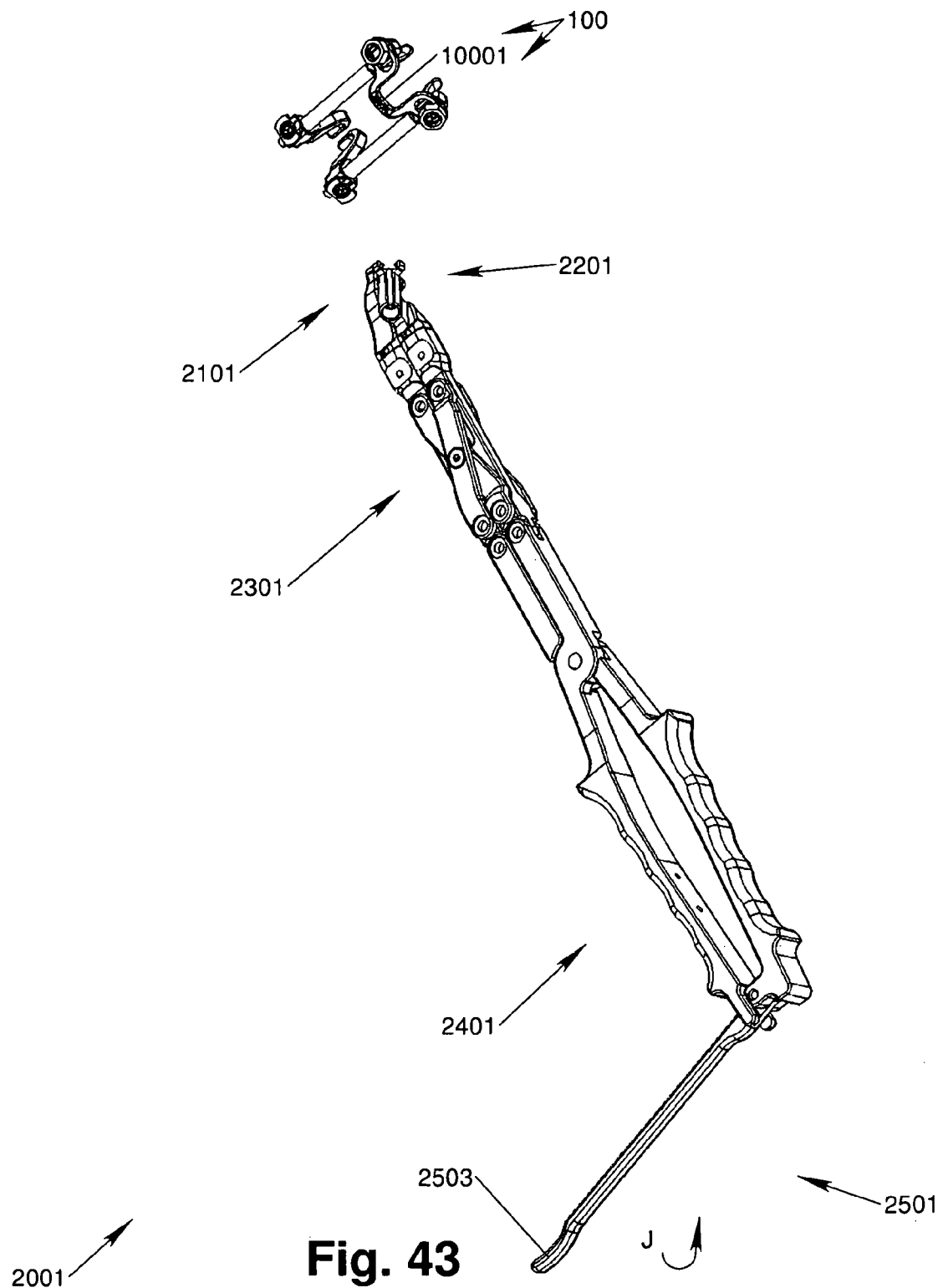

Finally, the inserter apparatus 2001 is removed from the patient and detached from the implant 100, 200, 300, 400, 500 as shown in FIG. 43. The inserter apparatus 2001 is detached from the implant by first rotating the ratchet bar 2501 in direction J as shown in FIG. 43. Care should be taken to grasp the ratchet bar 2501 from the proximal end 2503 to prevent inadvertent tearing of surgical gloves due to the sharp edges of the teeth on rack 2505 of the ratchet bar 2501 mechanism. A smooth and concave grasping point is provided on the proximal end 2503 to prevent the inadvertent tearing of gloves. The inserter apparatus 2001 handles 2401 can then be moved away from one another which will cause the second gripping portion 2201 to disengage from the implant. The inserter apparatus 2001 can then be tilted at a 45 degree angle from the implant 100, 200, 300, 400, 500 to then disengage the elongate rod member from the first gripping portion 2101. The inserter apparatus 2001 will then be removed from the incision and the patient closed.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A spinal implant assembly for engaging adjacent vertebrae with the spinal implant assembly comprising:
   a generally U-shaped body having a base portion with opposite ends, spaced side arm portions each having a distal, free end with the spaced side arm portions extending from the respective ends of the base portion;
   a distal opening at the distal free ends of the spaced side arm portions such that the generally U-shaped body is open at the distal ends;
   a stop portion of the base portion extending between the side arm portions;
   a pair of vertebral engaging arms configured and sized to be received between the side arm portions for extending through the distal opening;
   an arcuate seat of each of the vertebral engaging arms for engaging one of the adjacent vertebrae; and
   a pivot mechanism for pivotably connecting the vertebral engaging arms and the body portion, the vertebral engaging arms engaged with the stop portion in an operable configuration thereof with the arcuate seats facing in generally opposite directions away from each other, and the vertebral engaging arms pivoted away from the stop portion toward each other with the vertebral engaging arms extending through the distal opening adjacent each other in an inoperable configuration thereof.

2. The spinal implant assembly of claim 1 wherein the vertebral engaging arms include engagement ends having the arcuate seats and intermediate portions, the intermediate portions configured to have a width less than a width of the engagement ends to minimize space between the vertebral engagement arms in the inoperable configuration.

3. The spinal implant assembly of claim 1 wherein one of the vertebral engaging arms includes a narrow proximal end and the other vertebral engaging arm includes a slotted proximal end configured to receive the narrow proximal end therein, the proximal ends configured to be received between the side arm portions.

4. The spinal implant assembly of claim 1 wherein the body portion includes a throughbore and locking mechanism for engaging the vertebral engaging arms and blocking movement thereof while in the operable configuration.

5. The spinal implant assembly of claim 4 wherein the throughbore is threaded and the locking mechanism is a threaded set screw.

6. A spinal implant assembly for engaging adjacent vertebrae with the spinal implant assembly comprising:
   a body having an opening;
   a first vertebral engaging arm including a first engagement end and a slotted proximal end defined by a pair of spaced arms, the pair of spaced arms configured to be received in the body opening;
   a second vertebral engaging arm having a second engagement end and a narrow proximal end, the narrow proximal end configured to be received between the pair of spaced arms when positioned in the body opening;
   a pivot mechanism for pivotably connecting the first and second vertebral engaging arms and the body portion with the first and second vertebral engaging arms received in the body opening, the first and second vertebral engaging arms being pivotable between inoperable and operable configurations; and
   a step on one of the vertebral engaging arms configured and arranged to be spaced from the other vertebral engaging arm with the arms in the operable configuration and to contact the other vertebral engaging arm when the arms are pivoted to the inoperable configuration in which the first and second engagement ends are adjacent one another.

7. The spinal implant assembly of claim 6 wherein the second engagement end of the second vertebral engaging arm has a distal end width and the narrow proximal end has a narrow width, the narrow width being smaller than the distal end width.

8. The spinal implant assembly of claim 7 wherein the step is positioned on the second vertebral engaging arm delineating a boundary between the distal end width and the narrow width, the step configured to contact a portion of the first engagement end when the first and second vertebral engaging arms are in the inoperable configuration.

9. The spinal implant assembly of claim 6 further comprising an insertion throughbore on at least one of the first and second vertebral engaging arms.

10. The spinal implant assembly of claim 6 further comprising a locking mechanism on the body configured to prevent movement of at least one of the first and second vertebral engaging arms.

* * * * *